(12) United States Patent
Dolan

(10) Patent No.: US 11,010,449 B1
(45) Date of Patent: *May 18, 2021

(54) MULTI-DIMENSIONAL DATA ANALYSIS AND DATABASE GENERATION

(71) Applicant: VFD Consulting, Inc., Las Vegas, NV (US)

(72) Inventor: Vera Dolan, Las Vegas, NV (US)

(73) Assignee: VFD CONSULTING, INC., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/900,694

(22) Filed: Jun. 12, 2020

Related U.S. Application Data

(63) Continuation-in-part of application No. 16/701,042, filed on Dec. 2, 2019, now Pat. No. 10,825,102, which is a continuation of application No. PCT/US2018/065170, filed on Dec. 12, 2018.

(60) Provisional application No. 62/626,530, filed on Feb. 5, 2018, provisional application No. 62/597,617, filed on Dec. 12, 2017.

(51) Int. Cl.
  *G06F 7/00* (2006.01)
  *G06F 17/30* (2006.01)
  *G06F 17/15* (2006.01)

(52) U.S. Cl.
  CPC .................. *G06F 17/153* (2013.01)

(58) Field of Classification Search
  CPC ....... G06F 17/153; G06F 17/16; G06N 20/00; G06K 9/6268
  USPC .......................................................... 707/723
  See application file for complete search history.

(56) References Cited

U.S. PATENT DOCUMENTS

| 7,644,361 | B2 | 1/2010 | Wu et al. | |
|---|---|---|---|---|
| 7,657,540 | B1* | 2/2010 | Bayliss | G06F 16/283 707/999.1 |
| 2003/0158749 | A1 | 8/2003 | Olchanski et al. | |
| 2004/0258295 | A1* | 12/2004 | Tiemeyer | G06T 7/0004 382/145 |
| 2008/0009684 | A1 | 1/2008 | Corsetti et al. | |
| 2008/0163824 | A1 | 7/2008 | Moser et al. | |
| 2013/0337836 | A1 | 12/2013 | Johnson | |
| 2014/0149028 | A1 | 5/2014 | Chapman et al. | |

(Continued)

FOREIGN PATENT DOCUMENTS

| JP | 2013508859 A | 3/2013 |
|---|---|---|
| WO | WO-2013097905 A1 | 7/2013 |

(Continued)

OTHER PUBLICATIONS

Appold, Determining Laboratory Reference Intervals: CLSI Guideline Makes the Task Manageable. Lab Medicine 40(2): 75-76 (2009).
Ceriotti, Prerequisites for Use of Common Reference Intervals. Clin Biochem Rev 28: 115-121 (2007).

(Continued)

*Primary Examiner* — Binh V Ho

(74) *Attorney, Agent, or Firm* — Wilson Sonsini Goodrich & Rosati

(57) ABSTRACT

Described herein are systems and methods for multi-dimensional analysis of complex data sets to generate multifactorial overlap intervals used in lookup tables to classify input data. Also disclosed are systems and methods for provisioning searchable databases comprising the multifactorial overlap intervals through a distributed network for remote access.

19 Claims, 20 Drawing Sheets

(56) References Cited

U.S. PATENT DOCUMENTS

| | | | |
|---|---|---|---|
| 2014/0195269 A1 | 7/2014 | Sircar et al. | |
| 2014/0236491 A1* | 8/2014 | Katayev | G16H 50/70 702/19 |
| 2016/0267397 A1 | 9/2016 | Carlsson | |
| 2018/0025035 A1 | 1/2018 | Xia et al. | |
| 2018/0165554 A1 | 6/2018 | Zhang et al. | |
| 2018/0285685 A1 | 10/2018 | Singh et al. | |
| 2018/0322130 A1 | 11/2018 | Spisic et al. | |
| 2019/0005115 A1 | 1/2019 | Warrier et al. | |
| 2019/0027253 A1* | 1/2019 | Hoover | G06Q 50/26 |
| 2019/0180381 A1 | 6/2019 | Dolan | |
| 2019/0357853 A1* | 11/2019 | Shi | G16H 50/50 |
| 2020/0027027 A1* | 1/2020 | Reeves | G06F 17/16 |
| 2020/0105411 A1* | 4/2020 | Peterson | G16H 40/67 |
| 2020/0118685 A1* | 4/2020 | Lee | G16H 50/30 |
| 2020/0152334 A1* | 5/2020 | Singh | G16H 50/70 |

FOREIGN PATENT DOCUMENTS

| | | |
|---|---|---|
| WO | WO-2017127822 A1 | 7/2017 |
| WO | WO-2018053528 A1 | 3/2018 |

OTHER PUBLICATIONS

Clinical and Laboratory Standards Institute, Defining, Establishing, and Verifying Reference Intervals in the Clinical Laboratory; Approved Guideline—Third Edition. CLSI Document EP28-A3c. 76 pages (2010).

Katayev et al. Establishing reference intervals for clinical laboratory test results: is there a better way? Am J Clin Pathol 133:180-186 (2010).

Miller et al., Reference Intervals: Strengths, Weaknesses, and Challenges. Clinical Chemistry 62(7): 916-923 (2016).

Ozarda, Reference Intervals: current status, recent developments and future considerations. Biochemia Medica 26(1): 5-16 (2015).

PCT/US2018/065170 International Preliminary Report on Patentability dated Jun. 16, 2020.

PCT/US2018/065170 International Search Report and Written Opinion dated Apr. 23, 2019.

Tate, Transference and Validation for Reference Intervals. Clinical Chemistry 61(8): 1012-1015 (2015).

U.S. Appl. No. 16/701,042 Final Office Action dated Apr. 30, 2020.

U.S. Appl. No. 16/701,042 Non-Final Office Action dated Jan. 23, 2020.

U.S. Appl. No. 16/217,624 First Action Interview dated Apr. 16, 2019.

* cited by examiner

MULTI-DIMENSIONAL DATA ANALYSIS AND DATABASE GENERATION

CROSS-REFERENCE

This application is a continuation-in-part of U.S. application Ser. No. 16/701,042, filed Dec. 2, 2019, which is a continuation of International Application No. PCT/US2018/065170, filed Dec. 12, 2018, which claims the benefit of U.S. Provisional Patent Application No. 62/626,530, filed Feb. 5, 2018, and U.S. Provisional Patent Application No. 62/597,617, filed Dec. 12, 2017, each of which is incorporated herein by reference in its entirety.

BACKGROUND

Data analysis using traditional modeling techniques can be subject to erroneous assumptions that result in inaccurate models. The output of such models may be based on assumed statistical data distributions that fail to objectively account for relevant information.

SUMMARY

Disclosed herein is a computer-implemented system for generating a searchable database comprising a multi-dimensional lookup table for input classification, the system comprising: (a) a digital processing device comprising a processor, a memory, and an operating system configured to perform executable instructions; and (b) a computer program including instructions executable by the digital processing device, the computer program comprising: (i) a data processing module comprising an extraction algorithm configured to extract data from a population of data records; (ii) a data ingestion module configured to import the data, the data comprising first parameter data, second parameter data, and outcome data from the population of data records; (iii) a grouping module configured to group the first parameter data into a first plurality of data groups and the second parameter data into a second plurality of data groups; (iv) a joining module configured to join the first plurality of data groups with the second plurality of data groups generating a plurality of joint parameters; (v) a comparison module configured to compare the outcome data with the plurality of joint parameters thereby generating joint outcome data; (vi) a distribution module configured to determine a distribution of the plurality of joint parameters; (vii) an overlap module comprising a machine learning algorithm configured to determine one or more areas of overlaps between the distribution of the plurality of joint parameters and the joint outcome data; (viii) an interval generating module configured to generate one or more overlap intervals based on the one or more areas of overlap; and (ix) a table generating module configured to generate a multi-dimensional lookup table comprising the one or more overlap intervals, wherein the multi-dimensional lookup table is embedded within a searchable database accessed through a portal, wherein the portal is configured to receive input parameter values and generate an output comprising a classification of the input parameter values based on a comparison of the input parameter values with the one or more overlap intervals of the multi-dimensional lookup table. In some embodiments, the overlap module comprises a machine learning algorithm trained to automatically detect whether the overlap is present between the distribution of the plurality of joint parameters and the joint outcome data. In some embodiments, the computer program further comprises a communication module for interfacing with a distributed network of computing devices and providing the portal through the distributed network of computing devices. In some embodiments, the searchable database is periodically or dynamically updated with updated overlap intervals. In some embodiments, the distributed network of computing devices comprises desktop computers, tablets, mobile phones, or any combination thereof. In some embodiments, the input parameter values comprise sensor data obtained from the distributed network of computing devices. In some embodiments, the portal comprises a user interface configured to enable user upload of the input parameter values. In some embodiments, the computer program further comprises a data extraction module configured to extract the parameter data and outcome data for the population of data records from the data that is ingested. In some embodiments, the computer program further comprises a parameter selection module configured to allow the lookup table creator to select the first parameter, the second parameter, or both the first parameter and the second parameter. In some embodiments, the computer program further comprises a feature selection module configured to allow the lookup table creator to select the shared feature(s). In some embodiments, the computer program further comprises a visualization module configured to generate a 3D visualization of the distribution of the plurality of joint parameters and a 3D visualization of the joint or outcome data. In some embodiments, the computer program further comprises a module configured to send instructions to an output device to print or create a physical representation of the 3D visualization of the distribution of the plurality of joint parameters and/or the 3D visualization of the joint or outcome data. In some embodiments, the physical representation is a paper printout, a poster, or a 3D printed map or model. In some embodiments, the computer program further comprises a module configured to send instructions to an output device to print or create a physical representation of the multi-dimensional lookup table. In some embodiments, the physical representation is a paper printout, a poster, or a 3D printed map or model.

A reference interval for health or risk parameter assessment and evaluation of an individual ("reference interval") typically defines whether or not a measured health or risk parameter is normal or abnormal, is or is not prognostic, and/or is or is not diagnostic. A reference interval typically comprises one or more ranges of values where the respective upper and lower limits of said range(s) provides upper and lower limits of what is considered a normal value and/or a prognostic value and/or a diagnostic value for the specified health or risk parameter.

The traditional reference interval is typically based on the statistical fitting of a "bell curve" or other statistical function onto a distribution of any single health or risk parameter, such as a laboratory test or physical measurement, within small observational studies of populations. Currently used reference intervals typically are not individualized based on, for example, age and/or sex. That is, the current process for generating a traditional reference interval is the fitting of a standard statistical function to a data set comprising a single health or risk parameter, where the statistical function typically defines a normal distribution. The boundaries of the normal distribution of the data are deemed to be the boundaries of the reference interval for the data.

The traditional reference intervals for total cholesterol are 0 mg/dL at the low end and 199 mg/dL at the high end, with normal total cholesterol considered less than or equal to 199 mg/dL and abnormally high total cholesterol being 200 mg/dL or higher. Physical measurements such as body mass index and blood pressure are also typically reported where the reference intervals for normal may or may not be reported but are generally accepted and established as standard of care. For further example, a traditional reference interval for potassium levels in blood is 3.5-5.0 mEq/L, and, therefore, a potassium level of 4.0 mEq/L falls within the interval and is considered normal. Values of 3.2 mEq/L or 5.5 mEq/L of potassium levels in blood fall outside of the reference interval and are considered abnormal. The reference interval for potassium is notable in that individuals with potassium levels that fall outside of the traditional reference interval for potassium levels in blood are typically treated, because both hyperkalemia and hypokalemia are life threatening conditions that often require rapid medical attention and treatment. Hyperkalemia may also be at least partially diagnostic of renal failure, which is both a cause of hyperkalemia and life threatening in itself. Yet, as important as the reference intervals are for determining a life threatening condition in an individual, traditional reference intervals are not generated in an accurate manner.

This traditional method for generating reference intervals is inaccurate for at least two reasons: The population data samples used to generate the traditional reference intervals are typically relatively small, and fitting a statistical function to data consisting of a single health or risk parameter disregards the important interplay of other health or risk parameters with the fitted data thereby leading to absence of context for the data where the context may further define whether a particular parameter value is normal or abnormal.

At present, traditional reference intervals are generated using relatively small population sample sizes. Because the distribution of the data in these small sample sizes determines the reference intervals (i.e. determined by a normal distribution), the relatively small size of these population samples does not accurately reflect the larger and more varied populations for which the reference intervals are used. That is, the accuracy of the correspondence of the reference intervals increases with an increase in the size of the population sample used to determine the limits of the reference interval.

"There are many problems associated with the calculation of RI."[Katayev, et. al. Am J Clin Pathol 2010; 133:180-186] It has been recommended that a reference interval be established by selecting a statistically sufficient group (e.g., a minimum of 120) of healthy reference subjects. However, it is noted in the latest edition of the Clinical and Laboratory Standards Institute—approved guideline, "Defining, establishing, and verifying reference intervals in the clinical laboratory," that "Health is a relative condition lacking a universal definition. Defining what is considered healthy becomes the initial problem in any study." With traditional reference intervals generated using relatively small population sample sizes (e.g., 120), there are always a level of uncertainty and mistakes with a given selection protocol not only because of the definition of health that was selected but also because of the very real possibility that some of the selected subjects may, in fact, have subclinical disease." Id.

In addition, the traditional method for generating reference intervals does not adequately take into account multiple individual factors that would contextualize a data value that otherwise falls either within or outside of a traditional reference interval. That is, the same value that is deemed normal and healthy in one individual based on the traditional reference interval may be in fact an indication of poor health in another individual when, for example, other health factors and parameters are considered. Reference intervals are most accurate when they are based on multidimensional and multifactorial individual data.

Additionally, "test data very often exhibit a multimodal or an asymmetric distribution. This may reflect a large prevalence of subclinical disease within the selected population or subgroup-related differences in normal ranges. The latter requires partitioning of test data by sex, age, race, and other factors" of the test subjects, while traditional reference intervals are generated without such required partitioning of test data. Id.

The systems and methods disclosed herein represent a paradigm shift in generating the reference intervals from the traditional methods. Described herein are systems and methods for determining reference intervals such as, for example, reference intervals to be used by a healthcare provider to assess and evaluate a parameter of an individual. A parameter of an individual maybe linked to demographic data such as, for example, an individual's age. A parameter of an individual may comprise, for example, subjective data such as, for example, an individual's reported pain levels. A parameter of an individual may comprise objective data such as, for example, measured heart rate values or measured levels of biochemical analytes in blood or urine.

The reference intervals generated by the systems and methods described herein are based on large collections of data such as those from large populations. For example, the data sets used to calculate and establish a reference interval generated by the systems and methods described herein, in some embodiments, include 100,000 individuals or more. This is in contrast to the traditional method that relies on relatively small studies of around 120 individuals to provide data used to generate reference intervals.

The reference intervals generated by the systems and methods described herein are based on objective analysis and evidence-based models of individual data which compare the relationships of two or more health or risk parameters relative to one another. In this way, rather than basing off of an assumed model of a normal distribution of a single health or risk parameter, as in traditional reference intervals, the reference intervals generated by the instant systems and methods are based on an objective analysis of a plurality of health or risk parameters that are contextualized with one another. For example, a first health or risk parameter may be a total cholesterol level (as measured from blood samples) and a second health or risk parameter may be an HDL level (as measured from blood samples). In the instant systems and methods described herein, these two health or risk parameters are measured together in each subject in the data set and then the total cholesterol and HDL values for each individual are paired so that, for example, the total cholesterol value is contextualized by the HDL value. In this particular example, a total cholesterol value that would be deemed unhealthy by the traditional reference intervals would be considered with respect to HDL in the instant reference intervals, and that the same total cholesterol together with an elevated HDL would be deemed normal or healthy.

The reference intervals generated by the systems and methods described herein, at least in some embodiments, cross-reference a plurality of health or risk parameters with a mortality or adverse outcome rate measure associated with the plurality of parameters. For example, in a set of data points where total cholesterol and HDL values are paired, the paired data is further paired with the mortality rates for the respective pairs of cholesterol and HDL values. In these embodiments, the range of values over which the mortality risk levels are the lowest help determine the reference intervals.

Described herein is a computer implemented method for generation of a database with reference intervals comprising: receiving a first plurality of health or risk parameter values, a second plurality of health or risk parameter values, a population percentage, and a mortality or adverse outcome rate, wherein each of the first and the second health or risk parameter value is measured in a population; mapping, graphically in three dimensions, the first and the second health or risk parameter values with a population percentage thereby generating a population percentage map; mapping, graphically in three dimensions, the first and the second health or risk parameter values with the mortality or adverse outcome rate, thereby generating a mortality or adverse outcome rate map; overlaying the population percentage map onto the mortality or adverse outcome rate map thereby generating an overlap map; generating the reference interval values based on the overlap map; and populating the database with the reference interval values. In some embodiments, the method comprises segregating the first plurality of individual values into a first plurality of value groups and segregating the second plurality of individual values into a second plurality of value groups. In some embodiments, wherein upper value limits and lower value limits of each of the first plurality of value groups and each of the second plurality of value groups are determined after generation of the overlap map. In some embodiments, the method comprises associating, respectively, each of the first plurality of value groups with each of the second plurality of value groups thereby generating a plurality of associated groups. In some embodiments, the method comprises associating, respectively, each of the associated groups with each of the third plurality of individual parameter values. In some embodiments, the method comprises determining a population percentage of each of the associated groups. In some embodiments, each of the third plurality of individual parameter values comprise a mortality or adverse outcome rate respectively associated with each of the associated groups. In some embodiments, the method comprises mapping, graphically in three dimensions, the first and the second individual health or risk parameter values with the population percentage thereby generating a population percentage map. In some embodiments, the method comprises overlaying the mortality or adverse outcome rate value map onto the population percentage map generating an overlap map. In some embodiments, the method comprises determining an area of overlapping values in the overlap map where the total population percentage is largest and the mortality rate or adverse outcome rate is lowest. In some embodiments, the reference interval comprises upper values and lower values of the area of overlapping values in the overlap map where the total population percentage is largest and the mortality rate or adverse outcome rate is lowest.

Described herein is a system comprising: a computing device comprising a processor; and a non-transitory computer-readable storage media encoded with a computer program including instructions executable by the processor that cause the processor to: receive a first plurality of individual health or risk parameter values, a second plurality of individual health or risk parameter values, a population percentage, and a mortality or adverse outcome rate, wherein each of the first, the second, and the third individual health or risk parameter value is measured in a population of individuals; map, graphically in three dimensions, the first and the second health or risk parameter values with the population percentage thereby generating a population percentage map; map, graphically in three dimensions, the first and the second health or risk parameter values with the mortality or adverse outcome rate thereby generating a mortality or adverse outcome rate map; overlay, the population percentage map onto the mortality or adverse outcome rate map thereby generating an overlap map; generate a reference interval values based on the overlap map; and populating a database with the reference interval values, the reference interval taking a form of a lookup table. In some embodiments, the computer program causes the processor to segregate the first plurality of individual health or risk parameter values into a first plurality of health or risk parameter value groups and segregating the second plurality of individual health or risk parameter values into a second plurality of health or risk parameter value groups. In some embodiments, wherein upper value limits and lower value limits of each of the first plurality of value groups and each of the second plurality of value groups after generation of the overlap map. In some embodiments, the computer program causes the processor to associate, respectively, each of the first plurality of health or risk parameter value groups with each of the second plurality of health or risk parameter value groups thereby generating a plurality of associated groups. In some embodiments, the computer program causes the processor to associate, respectively, each of the associated groups with each of the third plurality of health or risk parameter values. In some embodiments, the computer program causes the processor to associate determine a population percentage of each of the associated groups. In some embodiments, each of the third plurality of individual parameter values comprise a mortality or adverse outcome rate respectively associated with each of the associated groups. In some embodiments, the computer program causes the processor to map, graphically in three dimensions, the first and the second individual health or risk parameter values with the population percentage thereby generating a population percentage map. In some embodiments, the computer program causes the processor to overlay the health or risk parameter value map onto the population percentage map generating an overlap map. In some embodiments, the computer program causes the processor to determine an area of overlapping health or risk parameter values in the overlap map where the total population percentage is largest and the mortality or adverse outcome rate is lowest. In some embodiments, the reference interval comprises upper values and lower values of the area of overlapping health or risk parameter values in the overlap map where the total population percentage is largest and the mortality or adverse outcome rate is lowest.

In another aspect, disclosed herein is a computer-implemented system for analyzing a population of individuals or other living organisms comprising a majority of healthy individuals/organisms, including their health or risk outcomes, in order to generate one or more reference intervals of joint first and second risk parameters, the one or more reference intervals useful for identifying a healthy or an unhealthy status of an individual or other living organism based on the first and second risk parameters, the system comprising: a digital processing device comprising a processor, a memory, and an operating system configured to perform executable instructions; and a computer program including instructions executable by the digital processing device to generate the one or more reference intervals, the computer program comprising: a data ingestion module configured to import data, the data comprising long-term health or other risk parameter data comprising first risk parameter data, second risk parameter data, and mortality or adverse outcome data from the population of individuals or living organisms having at least one shared demographic or other risk parameter feature, the population comprising a majority of healthy individuals/organisms and a minority of unhealthy individuals/organisms; a grouping module configured to group the first risk parameter data into a first plurality of data groups and the second risk parameter data into a second plurality of data groups; a joining module configured to join the first plurality of data groups with the second plurality of data groups generating a plurality of joint risk parameters; a comparison module configured to compare the mortality or adverse outcome data with the plurality of joint risk parameters thereby generating joint mortality or adverse outcome data; a distribution module configured to determine a distribution of the plurality of joint risk parameters; an overlap module configured to determine whether an overlap is present between the distribution of the plurality of joint risk parameters and the joint mortality or adverse outcome data; and an interval generating module configured to generate the one or more reference intervals based on the overlap, wherein when the overlap is present, the distribution of the plurality of joint risk parameters is relatively high and a mortality risk represented by the joint mortality or adverse outcome data is relatively low, and wherein the one or more reference intervals are used by a health care provider or other end user to identify the healthy or the unhealthy status of the individual and/or living organism. In some cases, the computer program comprises at least a first application and a second application. In some cases, the data ingestion module, the grouping module, the joining module, the comparison module, the distribution module, the overlap module, and the interval generating module are implemented in the first application, the second application, or both the first application and the second application. In some cases, the majority of healthy individuals and/or living organism comprises at least 60%, at least 70%, at least 80%, or at least 90% of the population. In some cases, the population of individuals and/or living organisms has at least 2, 3, 4 or 5 shared demographic features. In some cases, the shared demographic features comprise one or more of sex, age, race, and region of residence. In some cases, the one or more reference intervals comprises a lookup table. In some cases, the computer program further comprises a data extraction module configured to extract the health parameter data and mortality or adverse outcome data for the population from the data that is ingested. In some cases, the computer program further comprises a risk parameter selection module configured to allow the lookup table creator to select the first risk parameter, the second risk parameter, or both the first risk parameter and the second risk parameter. In some cases, the computer program further comprises a demographic selection module configured to allow the lookup table creator to select the shared demographic feature(s). In some cases, the computer program further comprises a visualization module configured to generate a 3D visualization of the distribution of the plurality of joint risk parameters and a 3D visualization of the joint mortality or adverse outcome data.

In another aspect, disclosed herein is non-transitory computer-readable storage media encoded with a computer program including instructions executable by a processor to analyze a population of individuals comprising a majority of healthy individuals, including their health or risk outcomes, in order to generate one or more reference intervals of joint first and second risk parameters, the one or more reference intervals useful for identifying a healthy or an unhealthy status of an individual based on the first and second risk parameters, the computer program comprising:
a data ingestion module configured to import data, the data comprising long-term health parameter data comprising first risk parameter data, second risk parameter data, and mortality or adverse outcome data from the population of individuals having at least one shared demographic feature, the population comprising a majority of healthy individuals and a minority of unhealthy individuals; a grouping module configured to group the first risk parameter data into a first plurality of data groups and the second risk parameter data into a second plurality of data groups; a joining module configured to join the first plurality of data groups with the second plurality of data groups generating a plurality of joint risk parameters; a comparison module configured to compare the mortality or adverse outcome data with the plurality of joint risk parameters thereby generating joint mortality or adverse outcome data; a distribution module configured to determine a distribution of the plurality of joint risk parameters; an overlap module configured to determine whether an overlap is present between the distribution of the plurality of joint risk parameters and the joint mortality or adverse outcome data; an interval generating module configured to generate the one or more reference intervals based on the overlap, wherein when the overlap is present, the distribution of the plurality of joint risk parameters is relatively high and an mortality risk represented by the joint mortality or adverse outcome data is relatively low, and wherein the one or more reference intervals are used by a health care provider or other end user to identify the healthy or the unhealthy status of the individual. In some cases, the computer program comprises at least a first application and a second application. In some cases, the data ingestion module, the grouping module, the joining module, the comparison module, the distribution module, the overlap module, and the interval generating module are implemented in the first application, the second application, or both the first application and the second application. In some cases, the majority of healthy individuals comprises at least 60%, at least 70%, at least 80%, or at least 90% of the population. In some cases, the population of individuals has at least 2, 3, 4 or 5 shared demographic features. In some cases, the shared demographic features comprise one or more of sex, age, race, and region of residence. In some cases, the one or more reference intervals comprises a lookup table. In some cases, the computer program further comprises a data extraction module configured to extract the health parameter data and mortality or adverse outcome data for the population from the data that is ingested. In some cases, the computer program further comprises a risk parameter selection module configured to allow the lookup table creator to select the first risk parameter, the second risk parameter, or both the first risk parameter and the second risk parameter. In some cases, the computer program further comprises a demographic selection module configured to allow the lookup table creator to select the shared demographic feature (s). In some cases, the computer program further comprises a visualization module configured to generate a 3D visualization of the distribution of the plurality of joint risk parameters and a 3D visualization of the joint mortality or adverse outcome data.

In yet another aspect, disclosed herein is a computer-implemented system for analyzing a population of individuals in order to generate one or more reference intervals of joint first and second risk parameters, the one or more reference intervals useful for identifying a status of an individual based on the first and second risk parameters, the system comprising: a digital processing device comprising a processor, a memory, and an operating system configured to perform executable instructions; and a computer program including instructions executable by the digital processing device to generate the one or more reference intervals, the computer program comprising: a data ingestion module configured to import data, the data comprising long-term parameter data comprising first risk parameter data, second risk parameter data, and outcome data from a population of individuals having at least one shared demographic feature, the population comprising individuals having the status and individuals not having the status; a grouping module configured to group the first risk parameter data into a first plurality of data groups and the second risk parameter data into a second plurality of data groups; a joining module configured to join the first plurality of data groups with the second plurality of data groups generating the plurality of joint risk parameters; a comparison module configured to compare the outcome data with the plurality of joint risk parameters thereby generating joined outcome data; an interval generating module configured to generate the reference interval, and wherein the one or more reference intervals are used to determine the status of the individual, and a table generating module configured to generate a two dimensional lookup table comprising the one or more reference intervals, wherein the lookup table is used to determine the status of the individual. In some cases, the computer program comprises at least a first application and a second application. In some cases, the data ingestion module, the grouping module, the joining module, the comparison module, and the interval generating module are implemented in the first application, the second application, or both the first application and the second application. In some cases, the individuals not having the status comprise at least 60%, at least 70%, at least 80%, or at least 90% of the population. In some cases, the population of individuals has at least 2, 3, 4 or 5 shared demographic features. In some cases, the shared demographic features comprise one or more of sex, age, race, and region of residence. In some cases, the outcome data comprises one or more of mortality or adverse outcome data, risk data, and diagnostic data. In some cases, the one or more reference intervals comprises a lookup table. In some cases, the computer program further comprises a data extraction module configured to extract the parameter data and outcome data for the population from the data that is ingested. In some cases, the computer program further comprises a risk parameter selection module configured to allow the lookup table creator to select the first risk parameter, the second risk parameter, or both the first risk parameter and the second risk parameter. In some cases, the computer program further comprises a demographic selection module configured to allow the lookup table creator to select the shared demographic feature(s). In some cases, the computer program further comprises a distribution module configured to determine a distribution of the plurality of joint risk parameters. In some cases, the computer program further comprises a visualization module configured to generate a 3D visualization of the distribution of the plurality of joint risk parameters and a 3D visualization of the joined outcome data. In some cases, the computer program further comprises an overlap module configured to determine a region of overlap between the 3D visualization of the distribution of the plurality of joint risk parameters and the 3D visualization of the joined outcome data. In some cases, the region of overlap comprises a value or a range of values wherein both the distribution of the plurality of joint risk parameters is relatively high and an outcome risk represented by the joined outcome data is relatively low. In some cases, the one or more reference intervals is based on the region of overlap.

In yet another aspect, disclosed herein is non-transitory computer-readable storage media encoded with a computer program including instructions executable by a processor to analyze a population of individuals in order to generate one or more reference intervals of joint first and second risk parameters, the one or more reference intervals useful for identifying a status of an individual based on the first and second risk parameters, the computer program comprising: a data ingestion module configured to import data, the data comprising long-term parameter data comprising first risk parameter data, second risk parameter data, and outcome data from a population of individuals having at least one shared demographic feature, the population comprising individuals having the status and individuals not having the status; a grouping module configured to group the first risk parameter data into a first plurality of data groups and the second risk parameter data into a second plurality of data groups; a joining module configured to join the first plurality of data groups with the second plurality of data groups generating the plurality of joint risk parameters; a comparison module configured to compare the outcome data with the plurality of joint risk parameters thereby generating joined outcome data; an interval generating module configured to generate the reference interval, and wherein the one or more reference intervals are used to determine the status of the individual; and a table generating module configured to generate a two dimensional lookup table comprising the one or more reference intervals, wherein the lookup table is used to determine the status of the individual. In some cases, the computer program comprises at least a first application and a second application. In some cases, the data ingestion module, the grouping module, the joining module, the comparison module, and the interval generating module are implemented in the first application, the second application, or both the first application and the second application. In some cases, the individuals not having the status comprise at least 60%, at least 70%, at least 80%, or at least 90% of the population. In some cases, the population of individuals has at least 2, 3, 4 or 5 shared demographic features. In some cases, the shared demographic features comprise one or more of sex, age, race, and region of residence. In some cases, the outcome data comprises one or more of mortality or adverse outcome data, risk data, and diagnostic data. In some cases, the one or more reference intervals comprise a lookup table. In some cases, the computer program further comprises a data extraction module configured to extract the parameter data and outcome data for the population from the data that is ingested. In some cases, the computer program further comprises a risk parameter selection module configured to allow the lookup table creator to select the first risk parameter, the second risk parameter, or both the first risk parameter and the second risk parameter. In some cases, the computer program further comprises a demographic selection module configured to allow the lookup table creator to select the shared demographic feature(s). In some cases, the computer program further comprises a distribution module configured to determine a distribution of the plurality of joint risk parameters. In some cases, the computer program further comprises a visualization module configured to generate a 3D visualization of the distribution of the plurality of joint risk parameters and a 3D visualization of the joined outcome data. In some cases, the computer program further comprises an overlap module configured to determine a region of overlap between the 3D visualization of the distribution of the plurality of joint risk parameters and the 3D visualization of the joined outcome data. In some cases, the region of overlap comprises a value or a range of values wherein both the distribution of the plurality of joint risk parameters is relatively high and an outcome risk represented by the joined outcome data is relatively low. In some cases, the one or more reference intervals is based on the region of overlap.

In another aspect, disclosed herein is a method for treating an individual based on a two-dimensional lookup table comprising one or more reference intervals of joint first and second data parameters, the method comprising: (a) selecting the individual for laboratory testing and evaluation using the two-dimensional lookup table comprising the one or more reference intervals, wherein a first health parameter value and a second health parameter value determined from the laboratory testing are compared to the one or more reference intervals to determine a health status indicating a risk of disease incidence or mortality of the individual; and (b) receiving results of the laboratory testing and evaluation of the patient sample using the two-dimensional lookup table comprising the one or more reference intervals, wherein said results comprise the health status indicating the risk of disease incidence or mortality of the individual; and (c) providing treatment to the individual based at least on said results comprising the health status indicating the risk of disease incidence or mortality of the individual, wherein the one or more reference intervals in the two-dimensional lookup table were generated by: (i) importing data, the data comprising health parameter data comprising first risk parameter data, second risk parameter data, and disease incidence or mortality data from a population having at least one shared feature; (ii) grouping the first risk parameter data into a first plurality of data groups and the second risk parameter data into a second plurality of data groups; (iii) joining the first plurality of data groups with the second plurality of data groups generating a plurality of joint risk parameters; (iv) comparing the disease incidence or mortality data with the plurality of joint risk parameters thereby generating joint disease incidence or mortality data; (v) determining a distribution of the plurality of joint risk parameters; (vi) determining whether an overlap is present between the distribution of the plurality of risk joint parameters and the joint disease incidence or mortality data; (vii) generating the one or more reference intervals based on the overlap, wherein when the overlap is present, the distribution of the plurality of joint risk parameters is relatively high and a disease incidence or mortality risk represented by the joint risk outcome data is relatively low; and (viii) generating the two dimensional lookup table comprising the one or more reference intervals, wherein said two-dimensional lookup table is configured to allow determination of the health status of the individual based on lab test results corresponding to the first and second risk parameters. In some embodiments, the plurality of reference intervals were generated by allowing a lookup table creator to select the first parameter, the second parameter, or both the first parameter and the second parameter. In some embodiments, the plurality of reference intervals were generated by allowing a lookup table creator to select the at least one shared feature. In some embodiments, the plurality of reference intervals were generated by generating a 3D visualization of the distribution of the plurality of joint risk parameters and a 3D visualization of the joint mortality or adverse outcome data.

In another aspect, disclosed herein is a method for treating an individual based on a lookup table comprising reference intervals, comprising: (i) selecting the individual for laboratory testing and evaluation using the lookup table comprising the reference intervals, wherein a first health parameter value and a second health parameter value determined from the laboratory testing are compared to the reference intervals to determine a health status indicating a risk of disease incidence or mortality of the individual; (ii) receiving results of the laboratory testing and evaluation of the patient sample using the lookup table comprising the reference intervals, wherein said results comprise the health status indicating the risk of disease incidence or mortality of the individual; and (iii) providing treatment to the individual based at least on said results comprising the health status indicating the risk of disease incidence or mortality of the individual, wherein the reference intervals in the lookup table were generated by: (i) receiving a first plurality of health or risk parameter values, a second plurality of health or risk parameter values, a population percentage, and a disease incidence or mortality rate, wherein the first plurality of health or risk parameter values, the second plurality of health or risk parameter values, or both are measured in a population; (ii) mapping, graphically in three dimensions, the first and the second health or risk parameter values with the population percentage thereby generating a population percentage map; (iii) mapping, graphically in three dimensions, the first and the second health or risk parameter values with the disease incidence or mortality rate, thereby generating an outcome rate map; (iv) comparing the population percentage map with the outcome rate map, thereby determining one or more areas of overlap; (v) generating the lookup table comprising the reference intervals based on the one or more areas of overlap; and (vi) populating the database with the reference intervals, wherein said lookup table is configured to allow determination of the health status of the individual based on lab test results corresponding to the first and second health or risk parameters. In some embodiments, the reference intervals were generated by further segregating the first plurality of health or risk parameter values into a first plurality of value groups and segregating the second plurality of health or risk parameter values into a second plurality of value groups. In some embodiments, the reference intervals were generated by further determining an upper value limit and a lower value limit of each of the first plurality of value groups and each of the second plurality of value groups after determining the one or more areas of overlap. In some embodiments, the reference intervals were generated by further associating, respectively, each of the first plurality of value groups with each of the second plurality of value groups thereby generating a plurality of associated groups. In some embodiments, the reference intervals were generated by further determining an area of overlapping values in the one or more areas of overlap where total population percentage is largest and the outcome rate is lowest. In some embodiments, the reference intervals comprise upper values and lower values of the area of overlapping values in the one or more areas of overlap where total population percentage is largest and the outcome rate is lowest.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
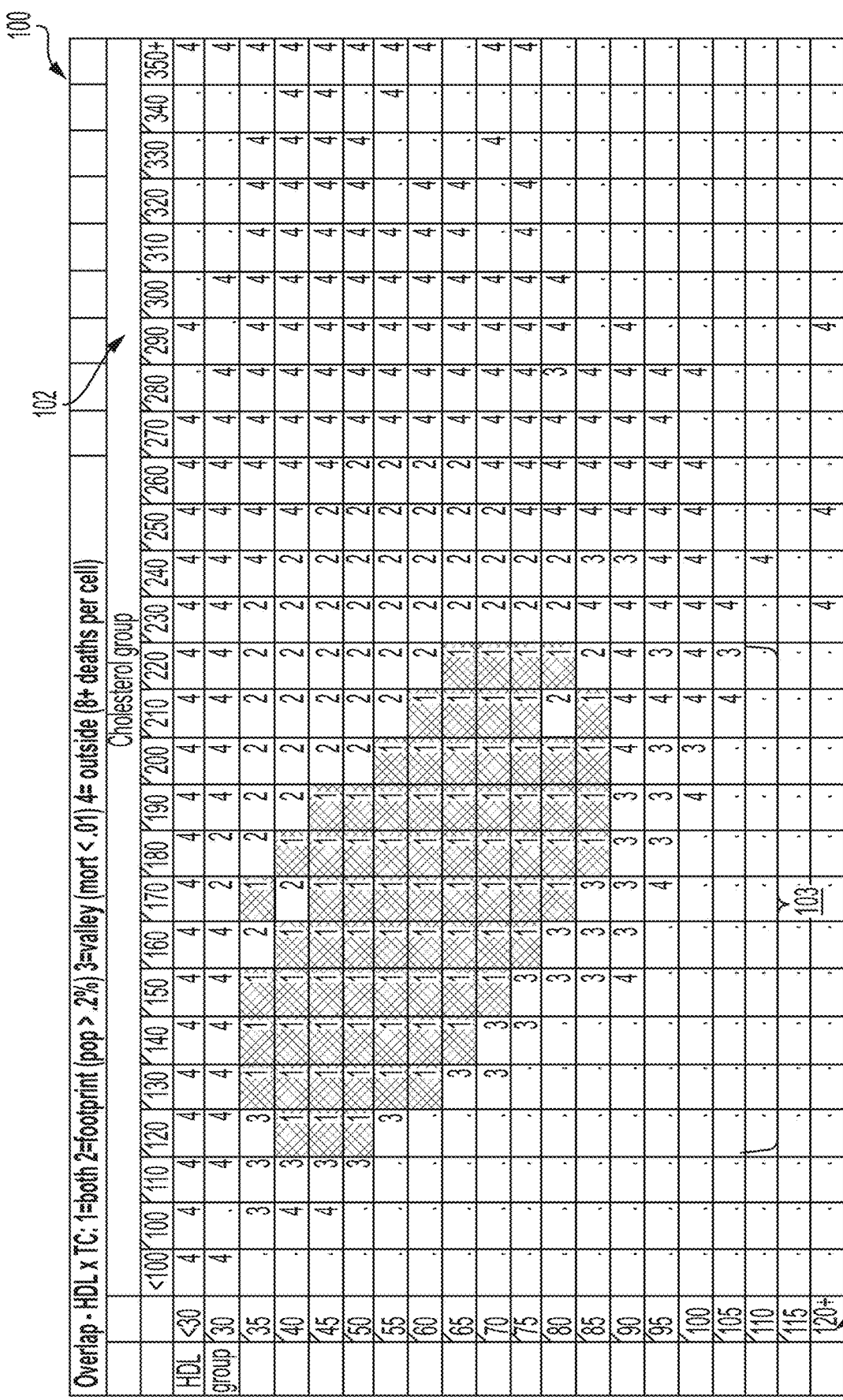
FIG. 1 shows an exemplary database as described herein.

Described herein are systems and methods for generating a reference interval as well as generating a database containing one or more reference intervals. A system as described herein, in some embodiments, comprises a computer based system and may further include one or more digital processing devices along with one or more computer programs.

Reference Intervals

A reference interval comprises a range of values wherein the upper and lower values of the reference interval provide a range of useful values to an individual to determine the status of that individual. In the healthcare field, reference intervals are typically used to assess and determine, for example, the overall health of an individual, a diagnosis, and/or a prognosis. If a metric, parameter, or laboratory test value is found to fall outside of the range of values defined by the relevant reference interval, the value, typically, is deemed abnormal. In certain cases, if a metric, parameter, or laboratory test value is found to fall within the range of values defined by the relevant reference interval, the value is deemed normal. If a metric, parameter, or laboratory test value is found to fall outside the range of values defined by the relevant reference intervals, the value can be deemed diagnostic and/or prognostic of a certain health condition. In certain cases, if a metric, parameter, or laboratory test value is found to fall within the range of values defined by the relevant reference intervals, the value is deemed diagnostic and/or prognostic of a certain condition.

A "reference value" is a reference interval comprising a single value such as, for example, a value that is expressed as a "positive" or a "negative" such as, for example, a fecal occult blood test. It should be understood as used herein that the term "reference interval" in certain embodiments refers to a "reference value."

A reference interval used by a healthcare provider or other end user may comprise one or more health or risk parameter values. A health or risk parameter value can be, for example, a sensed, measured, or observed value associated with an individual's health condition or status. The individual may be human, a mammal, or any other living organism. In some embodiments, the data used herein to generate a reference interval includes at least a first plurality of health or risk parameter values, a second plurality of health or risk parameter values, or a combination thereof. In some embodiments, the first plurality of health or risk parameter values is different from the second plurality of health or risk parameter values. In some embodiments, the first or the second plurality of health or risk parameter values are sensed or measured, for example, using a lab test, while the other of the first or the second plurality of health or risk parameter values are demographic data, for example, age, sex, or race of the individuals. In some embodiments, both the first and the second plurality of health or risk parameter values are sensed, measured, for example, using different lab tests.

Laboratory tests can be performed on a sample, for example, a biological sample of a subject. The biological sample may be a tissue or fluid of the subject, such as whole blood, plasma, serum, urine, saliva, mucosal excretions, sputum, stool and tears. The biological sample may be a tumor sample or heterogeneous tissue sample. The biological sample may have or be suspected of having disease tissue. The tissue may be processed to obtain the biological sample. The biological sample may be a cellular sample. The biological sample may be a cell-free (or cell free) sample, such as cell-free DNA or RNA. The biological sample may comprise cancer cells, non-cancer cells, immune cells, non-immune cells, or any combination thereof. The biological sample may be a tissue sample. The biological sample may be a liquid sample. The liquid sample can be a cancer or non-cancer sample. Non-limiting examples of liquid biological samples include synovial fluid, whole blood, blood plasma, lymph, bone marrow, cerebrospinal fluid, serum, seminal fluid, urine, and amniotic fluid. Health or risk parameter values can be specimen-derived values obtained using lab tests performed on a biological sample of the subject that correspond to one or more biomarkers informative of disease or health status.

In some embodiments, both the first and the second plurality of health or risk parameter values are not sensed, measured, for example, using a lab test but are different demographic data, for example, age and sex of the individuals. Non-limiting examples of types of health or risk parameter values comprise subjective data and/or objective data. Health or risk parameter values can be linked to or include demographic data of the individual. Non-limiting examples of demographic data includes but are not limited to age, sex, race, education, country of origin, and area or location of residence. Non-limiting examples of objective data include but are not limited to height, weight, body mass index, waist size, heart rate, blood pressure, saturated oxygen level, central venous pressure, arterial blood pressure, urine specimen derived values, blood specimen derived values, spinal fluid specimen derived values, stool derived values, bile fluid derived values, gastrointestinal content derived values, genetic alleles, diagnosis, genomic status, and vital status. Non-limiting examples of different specimen derived values include ABO Grouping (Blood Typing), Adrenocorticotropic Hormone level, Aldosterone level, Alpha 1 Antitrypsin level Alpha Fetoprotein level, Aluminum level, Amylase level, Antinuclear Antibody (ANA) Screen, Apolipoprotein A1 (Apo A1) level, Arsenic level, B12 level, Beta Carotene level, Beta HCG level, Bone-Specific Alkaline Phosphatase level, B-type natriuretic peptide level, Calcitonin, serum level, Calcium, Ionized level, Cancer Antigen 125 level, Cancer Antigen 15-3 level, Cancer antigen 27.29 level, Candida Antibodies level, Carbohydrate Antigen 19.9 level, Carcinoembryonic Antigen level, Carnitine level, Catecholamines level, Celiac Disease Antibody Screen, Ceruloplasmin level, Chemistry Panel & Complete Blood Count (CBC), Chromium, plasma level, Chromogranin A level, Complement C3 level, Complement C4 level, Copper level, CoQ10 (Coenzyme Q10) level, Cortisol level, Cortisol, 24 Hour level, Cortisol AM/PM level, Coxsackie Group B Antibodies, C-Peptide level, C-Reactive Protein level, Creatine Kinase level, C-Telopeptide, serum level, Cystatin C level, Cytokine Panel level, Cytomegalovirus (CMV) Antibodies, IgG, Cytomegalovirus (CMV) Antibodies, IgM, D-Dimer level, Dehydroepiandrosterone Sulfate level, Dihydrotestosterone level, Epstein Barr Virus, ESR, Estradiol level, Total Estrogen level, Estrone level, F2-Isoprostane level, Factor VIII Activity, Ferritin level, Fibrinogen level, Folate level, Fructosamine level, Galectin-3 level, Gamma Glutamyl Transferase level, Glutathione level, Gluten level, Helocobacter Pylori, IgG, Hemoglobin A1C level, Hepatitis B surface Antibody, Hepatitis C Virus Antibody, Homocysteine level, Human Herpes Virus Antibodies, Insulin-Like Growth Factor Binding Protein 3 (IGFBP-3), Intact N-Terminal Propeptide of Type 1 Procollagen (P1NP), Interleukin 6 (IL6), Interleukin 8 (IL-8), Interleukin 1beta (IL-1beta), Iodine level, Ionized Calcium level, Iron & Total Iron-Binding Capacity (TIBC), Lactate Dehydrogenase (LD) Isoenzymes, Leptin level, Lipase level, Lipoprotein (a) level, Lithium level, Magnesium level, Mercury level, Myeloperoxidase level, Osteocalcin level, Parathyroid Hormone level, Reticulocyte Count, Serotonin level, Sex Hormone Binding Globulin level, Transferrin level, Troponin I level, Tumor Necrosis Factor—Alpha level, Vitamin A level, Vitamin B1 level, Vitamin B12 level, Vitamin B6 level, Vitamin C level, Vitamin D level, Vitamin K1 level, Zinc level, Adrenocorticotropic Hormone level, Alkaline Phosphatase level, Aluminum level, Ammonia level, Antidiuretic Hormone level, Antinuclear Antibody, Arsenic level, B Type Naturetic Peptide level, Total Estrogen level, Progesterone level, Testosterone level, Prostate Specific Antigen level, C-Reactive Protein (High Sensitivity—Cardiac) level, Cadmium level, Calcium, Ionized (Serum) Test, Candida Antigen/Antibody Profile, Ceruloplasmin levels, Chlamydia Pneunomonia level, Complete Metabolic Panel, Copper level, Cortisol level, C-Peptide level, Dehydroepiandrosterone level, Dihydrotestosterone level, Epstein-Barr Virus level, Erythrocyte Sedimentation Rate, Estradiol level, Estriol level, Estrone level, Ferritin level, Folate level, Follicle-Stimulating Hormone level, Luteinizing Hormone level, Glucose-6-Phosphate Dehydrogenase level, Glutathione level, Growth Hormone level, Hemoglobin A1c level, Homocysteine level, IgA Immunoglobin level, IgE Immunoglobin level, Insulin level, Insulin Growth Factor (IGF-1), Iron level, Lactic Acid Dehydrogenase level, Lead level, Leptin level, Lipid level, Magnesium level, Manganese, Methylmalonic Acid level, Microalbumin level, Parathyroid Hormone level, Prolactin level, Prothrombin Time (PT), Partial Thromboplastin (PTT) Prothrombin Time INR, Reverse Triiodothyronine level, Selenium level, Sex Hormone-Binding Globulin level, T-3 Uptake, Testosterone Free and Total, Thyroglobulin, Thyroid Antibody level, Thyroid Stimulating Hormone level, Thyroxine (T4), Thyroxine Binding Globulin level, Tumor Necrosis Factor-Alpha, Uric Acid level, Total Cholesterol, HDL Cholesterol level, LDL Cholesterol level, Urine Specific Gravity (SG), Urine pH, Urine Protein level, Urine Glucose level, Urine Ketones, Urine Blood (hemoglobin) and Myoglobin, Urine Leukocyte Esterase, Urine Nitrite, Urine Bilirubin, Urobilinogen, and Fecal Occult Blood. Non-limiting examples of subjective data include skin color, degree of wound healing, reflex response, degree of consciousness, pain levels, and radiographic findings.

A reference interval as described herein may have different upper and/or lower limits for different populations of individuals. For example, groups having different demographics may have different reference intervals for one or more health or risk parameters. For example, in some embodiments, a reference interval for a potassium level in a Caucasian male between the ages of 50-69 differs from a reference interval for a potassium level in a non-Caucasian female between the ages of 20-39.

Typically, as described herein, a reference interval is generated for two or more health or risk parameter values that are contextualized relative to one another. In some embodiments, a reference interval is generated by contextualizing one or more health or risk parameter values with a mortality or adverse outcome rate associated with those specific parameters. In some embodiments, a reference interval is generated by contextualizing one or more health or risk parameter values with a mortality or adverse outcome rate associated with those specific parameters, and a population distribution associated with those specific parameters. In some embodiments, a reference interval is generated by contextualizing one or more health or risk parameter values with a population distribution associated with those specific parameters.

FIG. 1 shows an exemplary database 100. In database 100, total cholesterol values 102 are referenced with respect to HDL cholesterol values 101. In this way, each cell represents a small range of values of total cholesterol 102 and an associated HDL level range 101. A mortality rate is then associated with each cell of the database 100. For example, a total cholesterol of 150-159 and an HDL cholesterol level of 40-44 has a "1" in its cell as "1" represents a relatively low mortality level. Using database 100, a range of low mortality rate values 103 is presented. Individuals having a combined total cholesterol level value 102 and HDL cholesterol level value 101 that falls within the low mortality level range 103, are deemed normal. Individuals outside of the low mortality level range 103 are abnormal. In some embodiments, a measure of increased mortality is presented by providing numbers above "1" in cells associated with increased mortality. As shown in database 100, values of "2," "3," and "4" represent areas of increased mortality risk relative to combined total cholesterol 102 and HDL cholesterol levels 101 having a relatively low mortality risk 103.

Systems and Methods for Generating Reference Intervals

A system or method as described herein is typically used to generate one or more reference intervals which may then be used by a healthcare provider, other professional in the healthcare field or other end user to determine whether an individual value falls within or outside of a reference interval. In addition, in some embodiments, a system or method as described herein generates a database as containing or comprising one or more reference intervals in the form of lookup tables. In some embodiments, a database provides a relative risk of mortality or other adverse health outcome associated with one or more health or risk parameter values that fall either within or outside of a reference interval in the form of lookup tables.

Some embodiments of the systems described herein are computer based systems. These embodiments include a CPU including a processor and memory which may be in the form of a non-transitory computer readable storage medium. These system embodiments further include software that is typically stored in memory (such as in the form of a non-transitory computer readable storage medium) where the software is configured to cause the processor to carry out a function. Software embodiments incorporated into the systems described herein contain one or more modules.

The software embodiments described herein are configured to cause a processor to: receive population parameter data, generate a graphic map of the population parameter data (preferably in three dimensions), in some embodiments compare the graphic map to a second graphic map, determine a reference interval, and in some embodiments generate a database containing the reference interval.

Figure 2A:
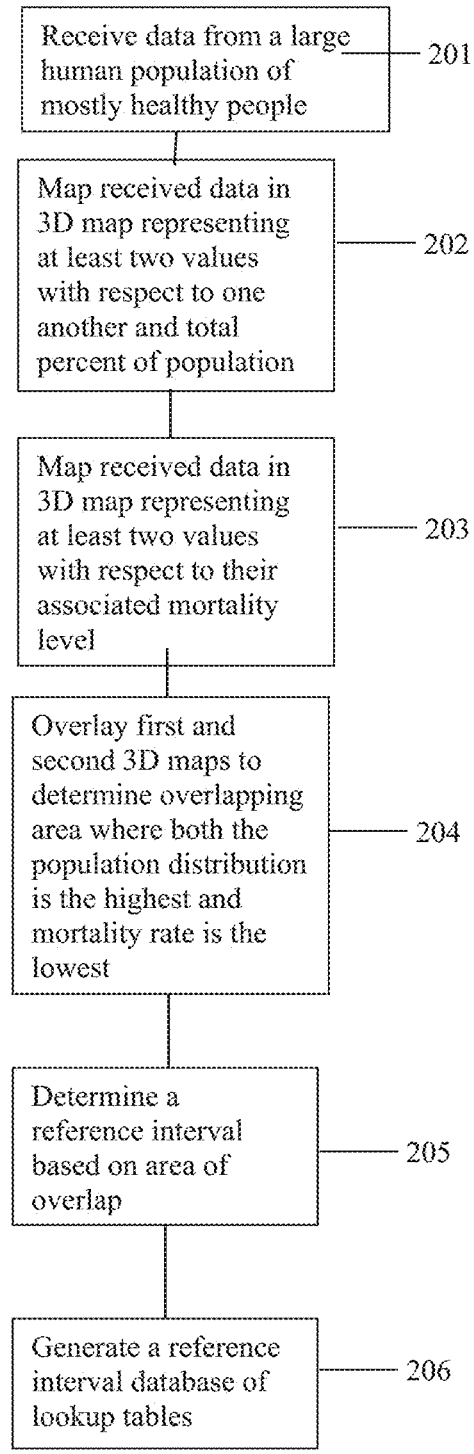
FIG. 2A shows an exemplary method as described herein.

FIG. 2A shows an exemplary method comprising the following exemplary steps: In a step 201, a device or system receives data from a large population of individuals. A large population suitable for use with the systems and methods described herein comprises, for example, a cohort study such as, for example, a study including 100,000 or more individuals. Data received comprises one or more population parameters (as described here). In a step 202, two or more received health or risk parameters are mapped preferably in a 3D graphic map with respect to their associated population distribution. The generated map is configured to represent two or more health or risk parameters with respect to each other so that, for example, one or more health or risk parameter values are contextualized relative to one or more other health or risk parameters. In a step 203, two or more health or risk parameters are mapped preferably in a 3D graphic map with respect to their associated mortality or other adverse health outcome level. In a step 204, the first and second 3D maps are compared as by, for example, overlaying one graphic map onto another to determine the presence of an overlapping area where both the population distribution is the highest and mortality or adverse outcome rate is the lowest. In a step 205, a reference interval is determined based on the upper and lower limits of a range in which both the population distribution of two compared health or risk parameters is the highest and the mortality or adverse outcome rate for the population is the lowest. In a step 206, a database is generated with the reference interval that was generated.

Figure 2B:
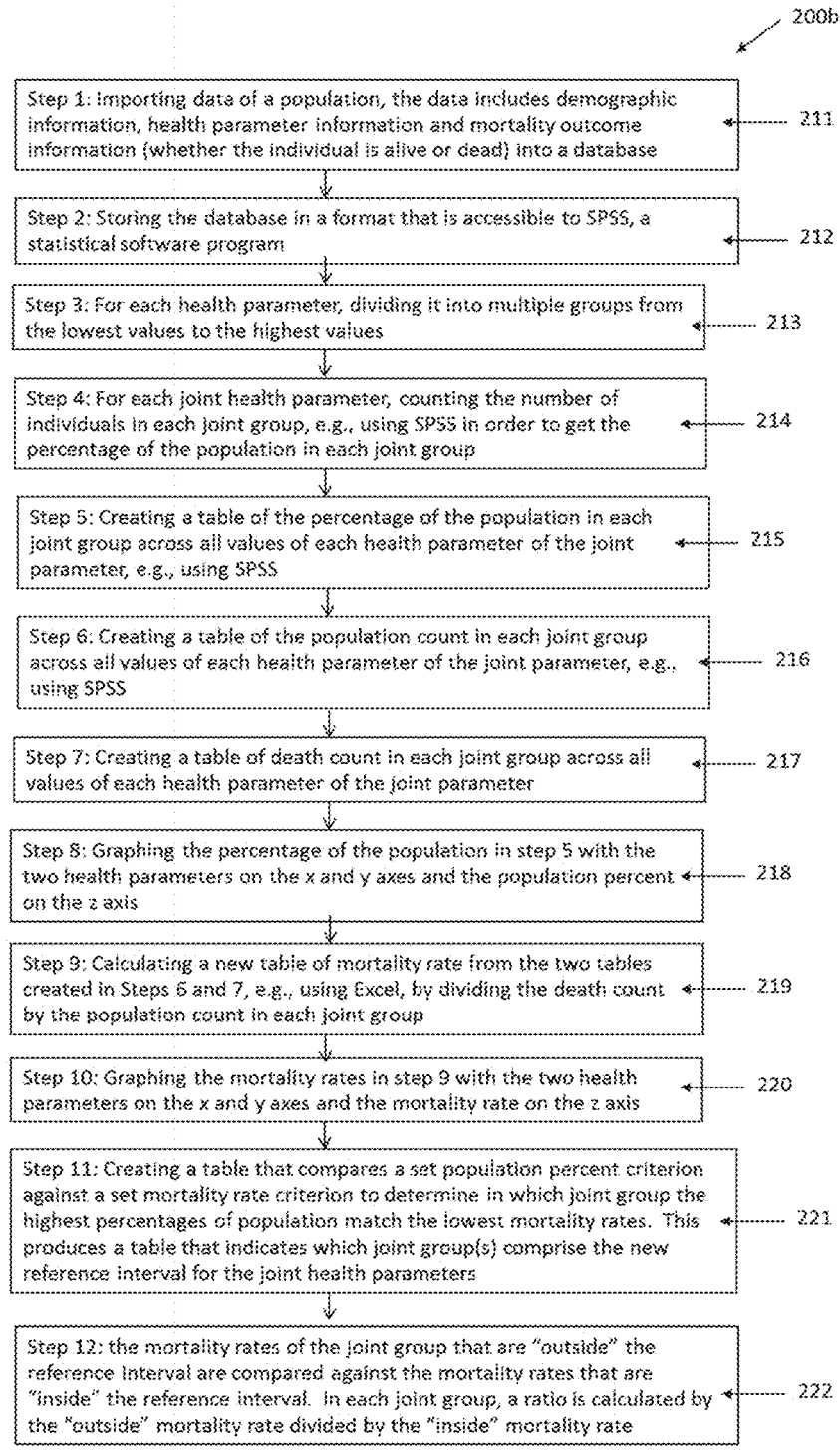
FIG. 2B shows a flow chart of steps in an exemplary embodiment of the systems and methods as described herein.

FIG. 2B shows exemplary steps of the systems and methods herein for analyzing a population of individuals comprising a majority of healthy individuals, including their health or risk outcomes, in order to generate one or more reference intervals of joint risk parameters includes. In this particular embodiment 200b, a population of people with demographic information, health parameter information and mortality outcome information (whether the individual is alive or dead) is recorded in an electronic database, 211. Then, such database is stored in a format that is accessible to a specified software program 212, such as Statistical Package for the Social Sciences (SPSS), a statistical software program. In step 3, 213, each health parameter is taken and divided into small groups from the very lowest values to the highest values, e.g., using SPSS. Non-limiting examples of health parameters include total cholesterol, HDL cholesterol and the cholesterol/HDL ratio. Examples of values that comprise small groups for total cholesterol are 0 to 5, 6 to 10, 11 to 15, etc. This same process is used for other health parameters. For each health parameter, the number of individuals in each small group is counted 214, for example, using SPSS, in order to get the percent of the study population in each small group. For example, two parameters can be processed at a time and count the number of individuals in the joint small groups to get the percent of the study population in each joint small group. An example of a joint small group using two parameters is total cholesterol 10 to 15 and HDL 0 to 5. In step 5, 215, the output from step 4, e.g., using SPSS, is used to create a table of the percentages of the study population in each joint small group across all values of the two health parameters. Such table can be created and/or saved in Excel. In step 6, 216, SPSS or other software can be used to create a table of the population count in each joint small group across all values of the two health parameters; such table can be saved into an Excel spreadsheet. Afterwards, SPSS or other software can be used to create a table of the death count in each joint small group across all values of the two health parameters 217, such table can be saved into an Excel spreadsheet. In step 8, 218, the study population percentages in the Excel table as described in Step 5 are graphed. They produce 3D graphs with the two health parameters on the x and y axes and the population percent on the z axis. In step 9, 219, a new table is calculated from the two tables created in steps 6 and 7, e.g., in Excel. The death count is divided by the population count in each joint small group cell to produce the mortality rate. In step 10, 220, the mortality rates in the Excel table as described in step 9 are graphed using Excel. They produce 3D graphs with the two health parameters on the x and y axes and the mortality rate on the z axis. In step 11, 221, from the results of the comparison of the graphs produced in step 8 and step 10, SPSS can be programmed to create a table that compares a set population percent criterion against a set mortality rate criterion to determine in which joint small group cells the highest percentages of population match the lowest mortality rates. This produces a table that indicates which joint small group cells comprise the new reference interval for the two joint health parameters. This is the beginning of the setup of the reference interval lookup table. In the last step 12, step 222, from the results of the new reference interval mortality rates, e.g., in Excel, the mortality rates of the joint small group cells that are "outside" the reference interval are compared against the mortality rates that are "inside" the reference interval. In each joint small group cell in the table, a ratio is calculated by the "outside" mortality rate divided by the "inside" mortality rate. This produces a complete lookup table that not only indicates which joint small groups comprise the reference interval, but indicates the extra mortality risk within each joint small group that is not inside the reference interval. As an example in FIG. 1, the small groups of female in the age range from 20-59 that are marked as 1 (e.g., mortality rate <0.01 and population >0.2%), 1 and 2 (e.g., population >0.2%), or 1, 2, and 3 (e.g., mortality rate <0.01) can be considered as "inside" the reference interval, while the groups marked as 4 can be considered as "outside" the reference interval with 8 or more deaths per cell.

Data Ingestion

Described herein are systems and methods includes a data ingestion module that ingest or import data in order to generate a reference interval based on information derived from the imported data.

In some cases, the data is healthcare-related data of a population of individuals. In some cases, the data is general data that is not related to health care. Each individual can be human, a mammal, or other living organism. In some cases, the data, e.g., each data point of the individual, is linked to demographic characteristics of the individual. Non-limiting examples of demographic data include age, sex, race, education, country of origin, area or location of residence, or the like. In some cases, the data includes outcomes such as vital status of the individual. Outcomes for health care-related data can include morbidity data, detection of one or more diseases, or presence of any health-care related event. For non-health care-related data, outcome data can be vital status or presence of any specified event such as a car crash, or a driving under influence (DUI). In some cases, the data comprises long-term parameter data. Such long-term data may facilitate elimination of influences by factors that occur in short term(s). In some cases, the data comprises short-term parameter data relating to acute health conditions of immediate concern. Such short-term data may facilitate reference intervals that call attention to urgent patient issues.

The parameter data can comprise first parameter data, second parameter data, and outcome data from a population of individuals having at least one shared feature (e.g. demographic feature). In some cases, the data comes from a predominantly healthy population. In some cases, the population comprises a majority of healthy individuals and a minority of unhealthy individuals. In some embodiments, the majority is greater than 50%, 55%, 60%, 65%, 70%, 75%, 80%, 85%, 90%, 95%, 98% or any other number in the range from 50% to 99.9% of the total population. In some embodiments, the minority is less than 50%, 45%, 40%, 35%, 30%, 25%, 20%, 15%, 10%, 5%, 2% or any other number in the range from 0.1% to 50% of the population. In some cases, the data is purchased, leased and/or freely accessed and downloaded from publically and/or privately available databases, optionally automatically. In some cases, the data is extracted or ingested from sources containing such data, for example, medical records (e.g., electrical/paper). Such data ingestion/extraction may include assistance from computer software/applications such as pattern recognition, image recognition, and optical character recognition (OCR). In some cases, extracting data utilizes a machine learning system, a pattern recognition algorithm, an artificial intelligence algorithm, a deep learning algorithm, or the like.

In some cases, data ingestion herein, by the data ingestion module comprises one or more different processing of the data. Non-limiting examples of extracting data includes: reading content, search content, organizing content, filtering content, removing content, and formatting content.

In some cases, data ingestion herein, for example, by the data ingestion module herein includes formatting the data in one or more consistent manners so that data obtained from different sources and very likely in different formats can be saved into uniform formats for further grouping, joining, comparison, or mapping.

In some cases, the systems and methods includes a data extraction module configured to extract the mortality or other health/risk outcome data for the population from the data that is ingested.

Data Grouping

Described herein are systems and methods that include a grouping module that groups each risk parameter data into one of multiple data groups. In some cases, the grouping is performed automatically with the ingestion data as its input. Other inputs can include: information of the population, prior knowledge regarding the risk parameter, or the like. In some embodiments, such multiple data groups are non-overlapping and provide complete coverage of the data range of the corresponding risk parameter. In other words, the data group covers the smallest data value to the highest possible data value of the corresponding risk parameter. In some cases, each group covers an identical data range. In some cases, one or more groups cover a different data range from the majority of groups. For example, the HDL data can be grouped into multiple groups as shown in Table 1, and the TC/HDL ratio data can be grouped into a different number of groups.

In some embodiments, such grouping is automatically performed. In some cases, the number of groups and the data range of each group are determined based on at least part of one or more selected from: the ingested data, information derived from the ingested data (e.g. profile of the ingested data, mean, median, maximal and minimal value of the ingested data), the size of the population or the number of total data points, the characteristics of the population, such as the demographic property of the population. For example, the number of groups can be fewer for a relatively smaller population.

In some embodiments, a parameter herein may include any number of groups that is greater than 2. In some embodiments, a parameter herein may include any number of groups in the range of 4 to 100. In some embodiments, a parameter herein may include any number of groups in the range of 8 to 50.

Data Joining and Distribution

Described herein are systems and methods that include a joining module configured to join multiple data groups of a risk parameter with data groups of another one or more risk parameters to generate a plurality of joint risk parameters. For example, 10 HDL groups and 15 total cholesterol level groups can be joined into 150 different joint risk parameters. Additional risk parameters may be joined with the joint risk parameter either simultaneously or sequentially. In some cases, the data of the joint risk parameters includes a distribution that is three-dimensional or of higher dimensions. In some cases, each data point may include a value for each and every joint risk parameters, where the value may or may not be identical for two of the joint risk parameters. When all the data points are considered together, the distribution may include an additional dimension that is the number of individuals, the percentage of the total population, or any other related metrics.

A data distribution module herein may be used to determine at least part of the distribution of data of the multiple joint risk parameters. Such determination may include automatic detection of features/characteristics of the distribution. For example, a mathematical evidence-based model that fits the distribution with specified criteria, a global peak, a valley, a local maximum, a local minimum, a slope, a gradient of a slope, or any other features.

The data distribution module herein may include generating a mathematical evidence-based model that fits the distribution with specified criteria based on the actual data. The mathematical evidence-based model can include one or more variables and/or one or more equations. The data distribution model can be configured to most accurately and closely model the data using one or more of: a linear, a non-linear, a statistical, a regression model, or the like.

Data Comparison

In some cases, a data comparison module herein is configured to compare the mortality or adverse outcome data with the plurality of joined risk parameters to generate joint mortality or adverse outcome data. In some cases, the mortality or adverse outcome data includes a total number of deaths in the total population or in one or more groups of risk parameters and/or a mortality rate (e.g. number of deaths/ population). In some embodiments, the joint mortality or adverse outcome data is within one or more groups of the total number of data groups. Such total number of data groups determined by the first number of groups of the first risk parameter and the second number of groups of the second risk parameter. As a non-limiting example, 10 groups of first risk parameter and 15 groups of second risk parameter can be joined into a total number of data groups for the mortality or adverse outcome data that is in the range of 1 to 150. Exemplary joint mortality or adverse outcome data is shown in Tables 4A-4B and 6.

Data Overlap

In some cases, an overlap module herein is configured to determine whether an overlap is present between the distribution of the plurality of joint risk parameters and the joint mortality or adverse outcome data. In some embodiments, an overlap or a partial overlap is where the distribution of the plurality of joint risk parameters is relatively high (e.g., number of individuals or percentage of population is high) and a mortality risk (e.g., death) represented by the joint mortality or adverse outcome data is relatively low. In some embodiments, an overlap or a partial overlap is where the distribution of the plurality of joint risk parameters is relatively high and a mortality risk (e.g., death) represented by the joined morbidity data (e.g., presence of specified disease(s)) is relatively low. In some embodiments, such determination does include visual determination. In some embodiments, such determination includes at least part of visual determination. A visualization module can be configured to generate a 3D visualization of the distribution of the plurality of joint risk parameters, for example, in FIGS. 3-6, and 11-14, and a 3D visualization of the joint mortality or adverse outcome data, for example, in FIGS. 7-10 and 15-18.

In some cases, the data overlap module herein is configured to compare one or more population percentage criteria with one or more mortality rate criteria to determine in which joint group(s) the highest percentage of population (e.g. above a specified threshold) match the lowest mortality rates (e.g. below a threshold). In some embodiments, the data comparison module generates a lookup table, e.g. two dimensional, with each cell of the lookup table indicating whether the joint group corresponding to that cell comprises the reference interval or not.

In some cases, determination of the overlap is automatic or semi-automatic. In some cases, the determination of the overlap based on the information obtained from the determined distribution and mortality or adverse health outcomes of the joint risk parameters.

Reference Interval Generation

In some cases, an interval generating module herein is configured to generate one or more reference intervals based on the determined overlap of distribution and mortality/adverse health outcomes. The generated reference interval(s) can be used by a health care provider or other end user to identify the healthy or the unhealthy status of the individual. In some embodiments, the individual is included in the total population that generates the joint risk parameter data and/or the reference interval(s). In some embodiments, the individual is not included in the total population that is used to generate the reference interval(s).

In some cases, a table generating module is configured to generate a two dimensional lookup table, as shown in FIG. 1, comprising the one or more reference intervals, wherein the lookup table is used to determine the status of the individual. In some embodiments, the lookup table includes values that are indicative of the presence of health or unhealthy status in each of the multiple joined groups. Although the illustrative examples shown are of two dimensional lookup tables, the methods disclosed herein enable generation of multi-dimensional lookup tables (e.g., having at least 3, 4, 5, 6, 7, 8, 9, etc., dimensions). The methods relating to the first and second health or risk parameter values can be expanded to include steps for evaluating additional parameter values (third, fourth, fifth, etc., parameter values). Multi-dimensional lookup tables can be generated and stored in a searchable database allowing for multiple health or disease status parameter values to be entered in order to query for an output indicative of health or disease status (e.g., inside or outside of the "normal" or "healthy" multi-dimensional reference range).

In some cases, the overlap module, the table generating module, or any other module herein includes an artificial intelligence algorithm, a machine learning algorithm, a pattern recognition algorithm, a deep learning algorithm or the like that is trained on prior data (with or without supervision). In some cases, the overlap module is trained to automatically identify/predict overlap in new data different from the ingested data used to generate the reference interval. In all cases, human oversight of the overlap analysis and comparison is necessary and required.

Data Mapping

Described herein are systems and methods that generate and/or utilize direct analysis, evidence-based models or maps of data in order to generate a reference interval. A map comprises one or more individual health or risk parameter values that are collected from a human population of individuals. The mapped data, in some embodiments, is arranged graphically in three dimensions. In some embodiments, the data points used by the systems and methods described herein are received from a large human population study such as, for example, a large cohort follow-up study. In some embodiments, a large human population comprises 100 or more individuals. In some embodiments, a large human population comprises 500 or more individuals. In some embodiments, a large human population comprises 1000 or more individuals. In some embodiments, a large human population comprises 5,000 or more individuals. In some embodiments, a large human population comprises 10,000 or more individuals. In some embodiments, a large human population comprises 25,000 or more individuals. In some embodiments, a large human population comprises 50,000 or more individuals. It should be understood as well that in some embodiments, any collection of human population data points is suitable for use with the systems and methods described herein including cohort studies, double blind prospective studies, retrospective studies, as well as collections of data from, for example, public studies, census collections, and human population parameter databases used for government, health care, insurance, actuarial, or other similar purposes.

Figure 3:
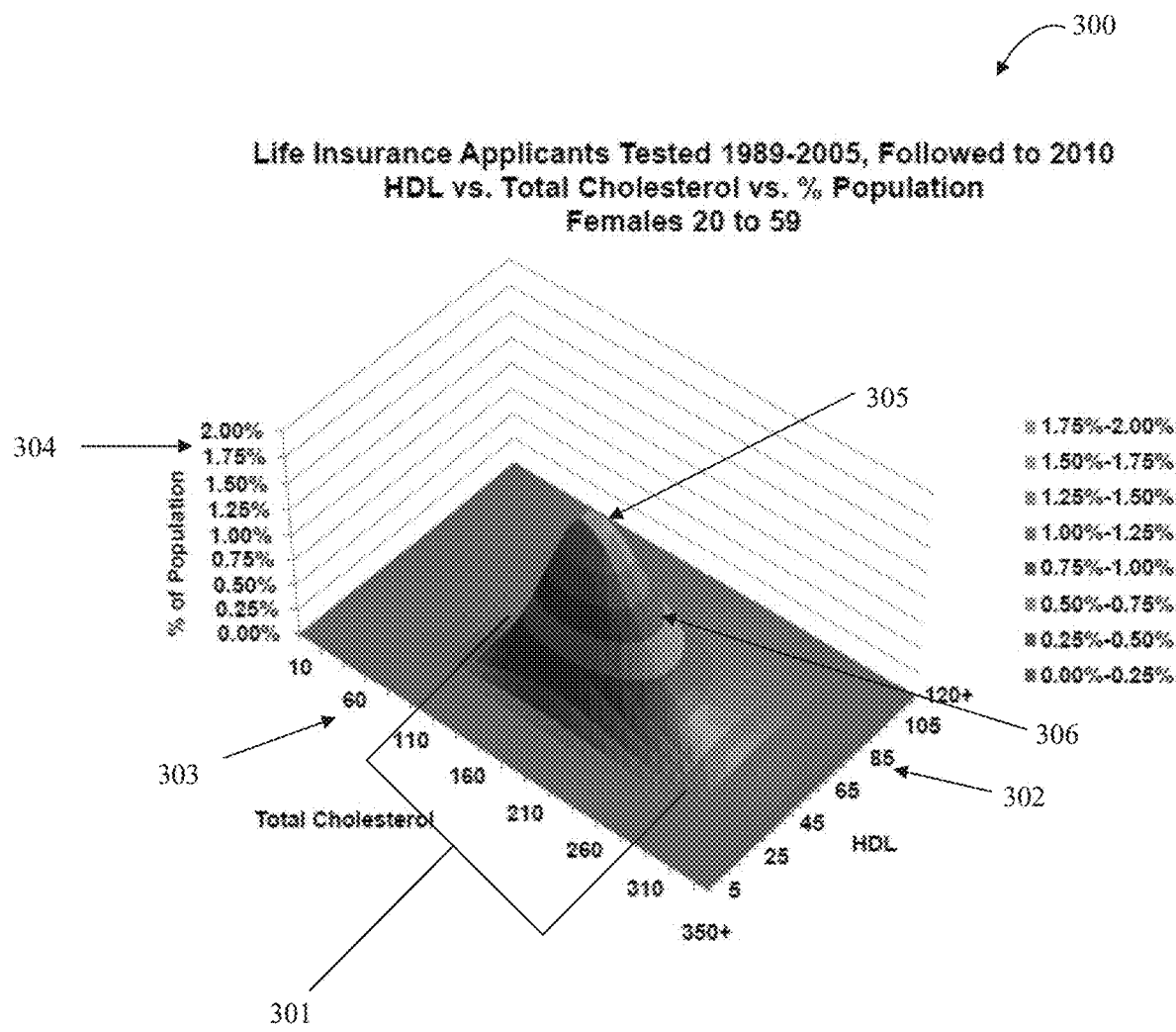
FIG. 3 shows an exemplary 3D graphic map as would be generated by the systems and methods described herein that represents three health or risk parameters taken from a population of individuals.

FIG. 3 shows an exemplary 3D graphic map 300, as would be generated by the systems and methods described herein, that represents three health or risk parameters taken from a population of individuals. In the 3D graphic map 300 shown, the health or risk parameters were taken from a large population study of 100,000 or more individuals. The data mapped in the 3D graphic map 300 comprises data collected from females between the ages of 20-59. Specifically, the data comprises the HDL and total cholesterol values for each individual. As shown in FIG. 3, HDL values are represented on a first axis 302 where the individual HDL values are divided into groups of 5 value units. For example, one HDL group contains HDL values from 25-29 units of HDL so that any individual with an HDL of, for example, 26 is placed in this group. Similarly, total cholesterol values are represented on a first axis 303 where the individual total cholesterol values are divided into groups of 10 value units. For example, one cholesterol group ranges from 60-69 units of total cholesterol so that any individual with a total cholesterol of, for example, 61 is placed in this group. A percentage of the population is represented on a third axis 304. These three health or risk parameter data points—HDL, total cholesterol, and percent of population are mapped in a 3D graphic map 300, wherein each individual's HDL and total cholesterol values are placed in their respective groups in the x-y plane and the percentage of the population that these groups represent is graphed on the z-axis. Mapping the values in the way creates a three dimensional representation of two joint health or risk parameter values (i.e. HDL level joined with Total cholesterol) along with the percentage of the population that the joint values represent. For example, individuals with an HDL of 45 and a Total cholesterol of 270 would be at or between 0% and 0.25% of the total population from which data was taken. A region 301 of the 3D graphic map 300 represents an area of the map 300 having the widest distribution of population values. A region 305 represents 1.5%-1.75% of the population shown on the graphic map 300 and has the least amount of distribution. A region 306 represents 0.75%-1.00% of the population shown on the graphic map 300 and has an intermediate amount of distribution as compared to regions 301 and 305.

In some embodiments, the upper and lower bounds of a reference interval are either equal to or determined by the outer bounds of the region 301 of the graphic map 300. The outer bounds of the area 300, in some embodiments, are determined by a computer program that computes the percentages of population within area 301. In some embodiments, the beginning and end points of the area where the calculated percentages of population are highest either are or determine the reference interval for HDL (or any other population parameter value represented by axis 302). In some embodiments, the beginning and end points of the area where the calculated percentages of population are highest either are or determine the reference interval for total cholesterol (or any other health or risk parameter value represented by axis 303). In some embodiments, the beginning and end points of the area where the calculated percentages of population are highest either are or determine the reference interval jointly for HDL (or any other population parameter value represented by axis 302) and total cholesterol (or any other health or risk parameter value represented by axis 303).

Figure 4:
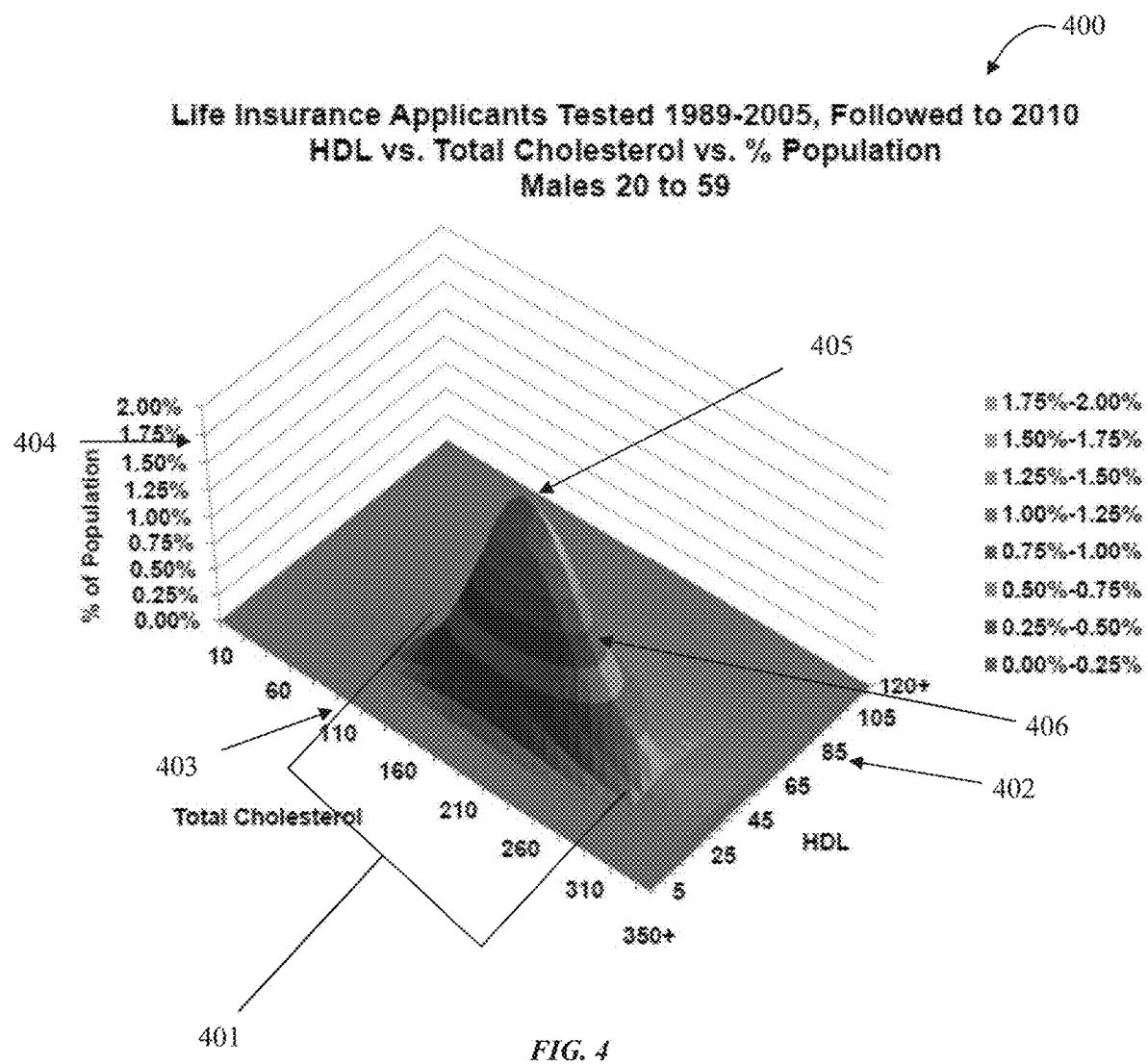
FIG. 4 shows an exemplary 3D graphic map as would be generated by the systems and methods described herein that represents three health or risk parameters taken from a population of individuals.

FIG. 4 shows an exemplary 3D graphic map 400, as would be generated by the systems and methods described herein, that represents three health or risk parameters taken from a population of individuals. In the 3D graphic map 400 shown, the health or risk parameters were taken from a large population study of 100,000 or more individuals. The data mapped in the 3D graphic map 400 comprises data collected from males between the ages of 20-59. Specifically, the data comprises the HDL and total cholesterol values for each individual. As shown in FIG. 4, HDL values are represented on a first axis 402 where the individual HDL values are divided into groups of 5 value units. For example, one HDL group contains HDL values from 25-29 units of HDL so that any individual with an HDL of, for example, 26 is placed in this group. Similarly, total cholesterol values are represented on a first axis 403 where the range of total cholesterol values are divided into groups of 10 value units. For example, one cholesterol group ranges from 60-69 units of total cholesterol so that any individual with a total cholesterol of, for example, 61 is placed in this group. A percentage of the population is represented on a third axis 404. The health or risk parameter data points are mapped in 3D graphic map 400, wherein each individual's HDL and total cholesterol values are placed in their respective groups in the x-y plane and the percentage of the population that these groups represent is graphed on the z-axis. Mapping the values in the way creates a three dimensional representation of two joint health or risk parameter values (i.e. HDL level joined with Total cholesterol) along with the percentage of the population that the joint values represent. For example, individuals with an HDL of 45 and a Total cholesterol of 270 would be at between 0% and 0.25% of the total population from which data was taken. A region 401 of the 3D graphic map 400 represents an area of the map 400 having the widest distribution of health or risk parameter values. It is notable that the 3D graphic map 300 (as shown in FIG. 3) differs in its range of greatest distribution 301 as compared with the area of greatest distribution 401 in 3D graphic map 400. This difference in the appearance of between graphic map 300 and graphic map 400 is presumed to be a result of a difference in sex between the populations (or sub-populations) represented respectively in each of the graphic maps 300 and 400. That there is a difference between graphic map 300 and graphic map 400, which are both for the same age range, highlights the value of separating data for generating reference intervals by sex. In some cases, a reference interval is determined based on at least a portion of a graphic map where a population distribution is greatest (i.e. ranges 301 and 401). Therefore, a difference in population distributions in 3D graphic maps of different age groups may represent a difference in a reference interval between one sex and another. Said yet another way, it is expected, based on the differences between graphic map 300 and graphic map 400 that a different reference interval would define a normal HDL value in a male between the age of 20-59 than a female between the age of 20-59. A region 405 represents 1.5%-1.75% of the population shown on the graphic map 400 and has the least amount of distribution. A region 406 represents 0.75%-1.00% of the population shown on the graphic map 400 and has an intermediate amount of distribution as compared to regions 401 and 405.

In some embodiments, the upper and lower bounds of a reference interval are either equal to or determined by the outer bounds of the region 401 of the graphic map 400. The outer bounds of the area 400, in some embodiments, are determined by a computer program that computes the percentages of population within area 401. In some embodiments, the beginning and end points of area where the calculated percentages of population are highest either are or determine the reference interval for HDL (or any other health or risk parameter value represented by axis 402). In some embodiments, the beginning and end points of the area where the calculated percentages of population are highest either are or determine the reference interval for total cholesterol (or any other health or risk parameter value represented by axis 403). In some embodiments, the beginning and end points of the area where the calculated percentages of population are highest either are or determine the reference interval jointly for HDL (or any other health or risk parameter value represented by axis 402) and total cholesterol (or any other health or risk parameter value represented by axis 403).

Figure 5:
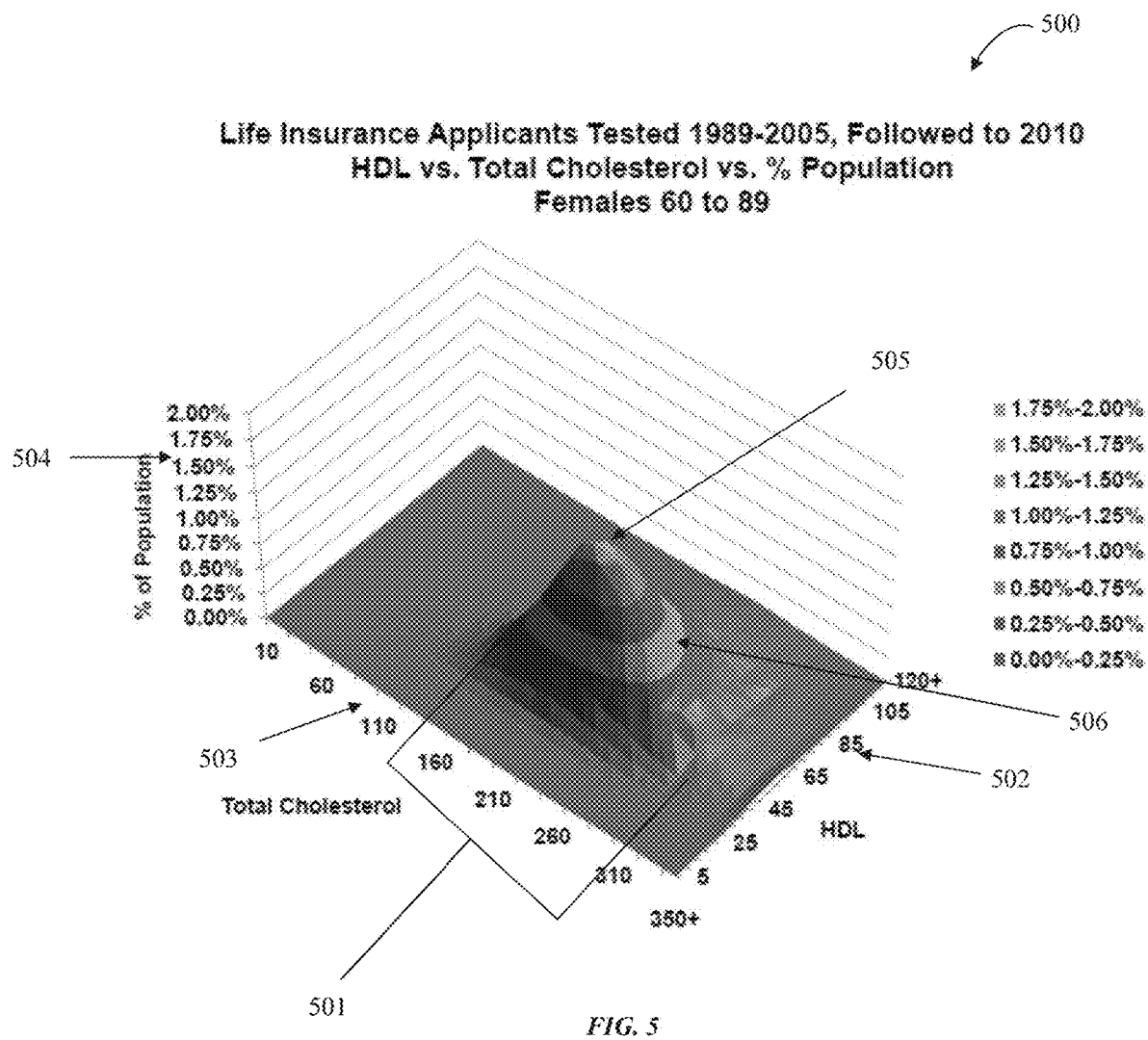
FIG. 5 shows an exemplary 3D graphic map as would be generated by the systems and methods described herein that represents three health or risk parameters taken from a population of individuals.

FIG. 5 shows an exemplary 3D graphic map 500, as would be generated by the systems and methods described herein, that represents three health or risk parameters taken from a population of individuals. In the 3D graphic map 500 shown, the health or risk parameters were taken from a large population study of 100,000 or more individuals. The data mapped in the 3D graphic map 500 comprises data collected from males between the ages of 20-59. Specifically, the data comprises the HDL and total cholesterol values for each individual. As shown in FIG. 5, HDL values are represented on a first axis 502 where the individual HDL values are divided into groups of 5 value units. For example, one HDL group contains HDL values from 25-29 units of HDL, so that any individual with an HDL of, for example, 26 is placed in this group. Similarly, total cholesterol values are represented on a first axis 503 where the individual total cholesterol values are divided into groups of 10 value units. For example, one cholesterol group ranges from 60-69 units of total cholesterol so that any individual with a total cholesterol of, for example, 61 is placed in this group. A percentage of the population is represented on a third axis 504. The health or risk parameter data points are mapped in 3D graphic map 500, wherein each individual's HDL and total cholesterol values are placed in their respective groups in the x-y plane and the percentage of the population that these groups represent is graphed on the z-axis. Mapping the values in the way creates a three dimensional representation of two joint health or risk parameter values (i.e. HDL level joined with total cholesterol) along with the percentage of the population that the joint values represent. For example, individuals with an HDL of 45 and a total cholesterol of 270 would be at between 0% and 0.25% of the total population from which data was taken. A region 501 of the 3D graphic map 500 represents an area of the map 500 having the widest distribution of individual health or risk parameter values. It is notable that the 3D graphic map 300 (as shown in FIG. 3) differs in its range of greatest distribution as compared with the 3D graphic map 500. This difference in the appearance of between graphic map 300 and graphic map 500 is presumed to be a result of a difference in ages between the populations (or sub-populations) represented respectively in each of the graphic map 300 and 500. That there is a difference between graphic map 300 and graphic map 500, which are both for the same sex, highlights the value of separating data for generating reference intervals by age. In some cases, a reference interval is determined based on portion of a graphic map where a population distribution is greatest in either 301 or 501. Therefore, a difference in population distributions in 3D graphic maps of different age groups may represent a difference in a reference interval between one age group and another. Said yet another way, it is expected, based on the differences between graphic map 300 and graphic map 500 that a different reference interval would define a normal HDL value in a female between the age of 20-59 than a female between the age of 60-89. A region 505 represents 1.5%-1.75% of the population shown on the graphic map 500 and has the least amount of distribution. A region 506 represents 0.75%-1.00% of the population shown on the graphic map 500 and has an intermediate amount of distribution as compared to regions 501 and 505.

In some embodiments, the upper and lower bounds of a reference interval are either equal to or determined by the outer bounds of the region 501 of the graphic map 500. The outer bounds of the area 500, in some embodiments, are determined by a computer program that computes the percentages of population within area 501. In some embodiments, the beginning and end points of the area where the calculated percentages of population are highest either are or determine the reference interval for HDL (or any other population parameter value represented by axis 502). In some embodiments, the beginning and end points of area where the calculated percentages of population are highest in 503 either are or determine the reference interval for total cholesterol (or any other population parameter value represented by axis 503). In some embodiments, the beginning and end points of area where the calculated percentages of population are highest in 503 either are or determine the reference interval jointly for HDL (or any other population parameter value represented by axis 502) and total cholesterol (or any other population parameter value represented by axis 503).

Figure 6:
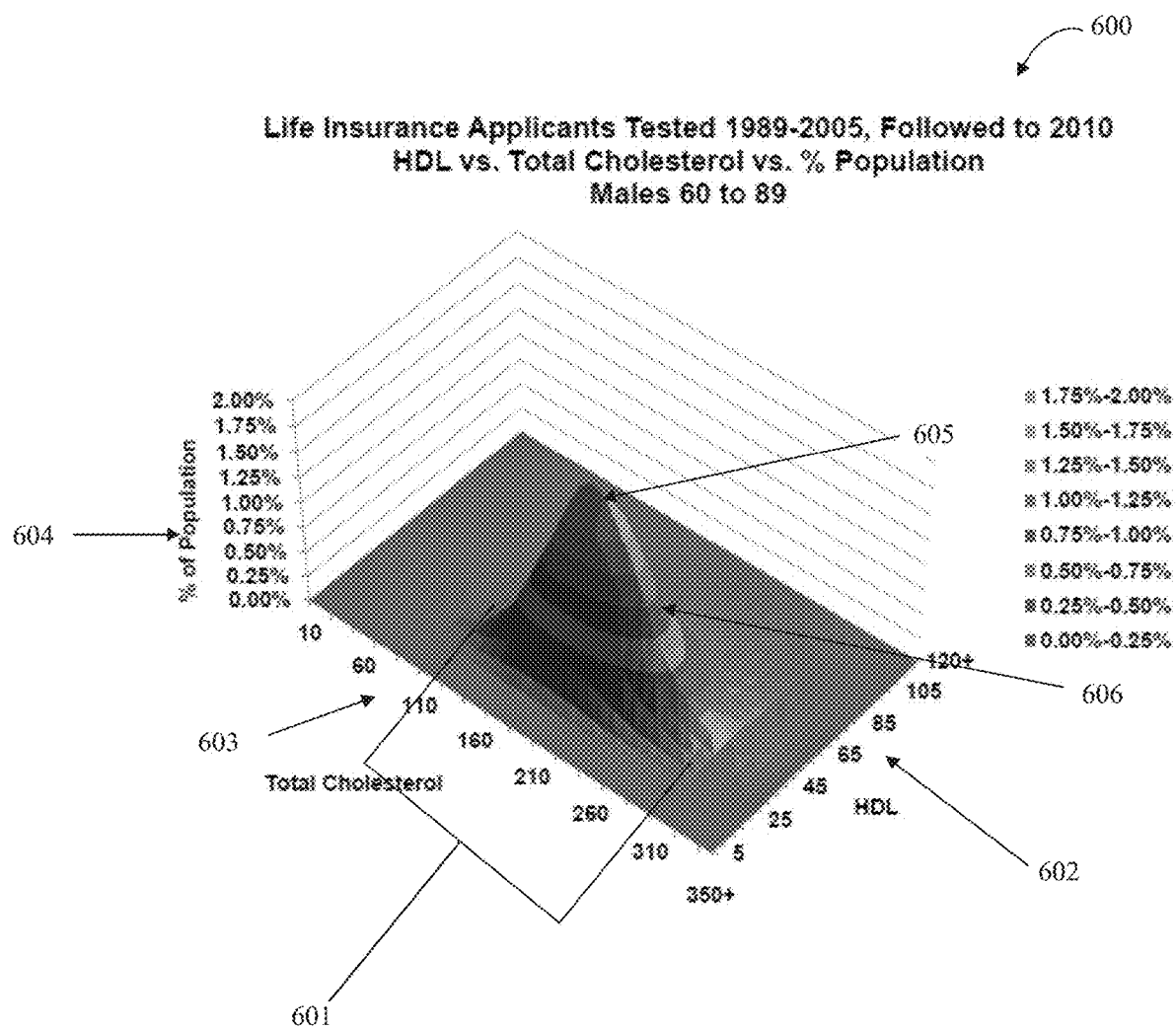
FIG. 6 shows an exemplary 3D graphic map as would be generated by the systems and methods described herein that represents three health or risk parameters taken from a population of individuals.

FIG. 6 shows an exemplary 3D graphic map 600, as would be generated by the systems and methods described herein, that represents three health or risk parameters taken from a population of individuals. In the 3D graphic map 600 shown, the health or risk parameters were taken from a large population study of 100,000 or more individuals. The data mapped in the 3D graphic map 600 comprises data collected from males between the ages of 60-89. Specifically, the data comprises the HDL and total cholesterol values for each individual. As shown in FIG. 6, HDL values are represented on a first axis 602 where the individual HDL values are divided into groups of 5 value units. For example, one HDL group contains HDL values from 25-29 units of HDL, so that any individual with an HDL of, for example, 26 is placed in this group. Similarly, total cholesterol values are represented on a first axis 603 where the individual total cholesterol values are divided into groups of 10 value units. For example, one cholesterol group ranges from 60-69 units of total cholesterol so that any individual with a total cholesterol of, for example, 61 is placed in this group. A percentage of the population is represented on a third axis 604. The health or risk parameter data points are mapped in 3D graphic map 600, wherein each individual's HDL and total cholesterol values are placed in their respective groups in the x-y plane and the percentage of the population that these groups represent is graphed on the z-axis. Mapping the values in the way creates a three dimensional representation of two joint health or risk parameter values (i.e. HDL level joined with total cholesterol) along with the percentage of the population that the joint values represent. For example, individuals with an HDL of 45 and a total cholesterol of 270 would be at between 0% and 0.25% of the total population from which data was taken. A region 601 of the 3D graphic map 600 represents an area of the map 600 having the widest distribution of individual values. It is notable that the 3D graphic map 400 (as shown in FIG. 4) differs in its range of greatest distribution as compared with the 3D graphic map 600. This difference in the appearance of between graphic map 400 and graphic map 600 is presumed to be a result of a difference in ages between the populations (or sub-populations) represented respectively in each of the graphic map 400 and 600. That there is a difference between graphic map 400 and graphic map 600, which are both for the same sex, highlights the value of separating data for generating reference intervals by age. In some cases, a reference interval is determined based on portion of a graphic map where a population distribution is greatest (i.e. regions 401 and 601). Therefore, a difference in population distributions in 3D graphic maps of different age groups may represent a difference in a reference interval between one age group and another. Said yet another way, it is expected, based on the differences between graphic map 400 and graphic map 600 that a different reference interval would define a normal HDL value in a male between the age of 20-59 and a male between the age of 60-89. A region 605 represents 1.5%-1.75% of the population shown on the graphic map 600 and has the least amount of distribution. A region 606 represents 0.75%-1.00% of the population shown on the graphic map 600 and has an intermediate amount of distribution as compared to regions 601 and 605.

In some embodiments, the upper and lower bounds of a reference interval are either equal to or determined by the outer bounds of the region 601 of the graphic map 600. The outer bounds of the area 600, in some embodiments, are determined by a computer program that computes the percentages of population within area 601. In some embodiments, the beginning and end points of the area where the calculated percentages of population are highest in either are or determine the reference interval for HDL (or any other population parameter value represented by axis 602). In some embodiments, the beginning and end points of the area where the calculated percentages of population are highest in either are or determine the reference interval for total cholesterol (or any other health or risk parameter represented on the axis 603). In some embodiments, the beginning and end points of the area where the calculated percentages of population are highest in either are or determine the reference interval jointly for HDL (or any other population parameter value represented by axis 602) and total cholesterol (or any other health or risk parameter represented on the axis 603).

Figure 7:
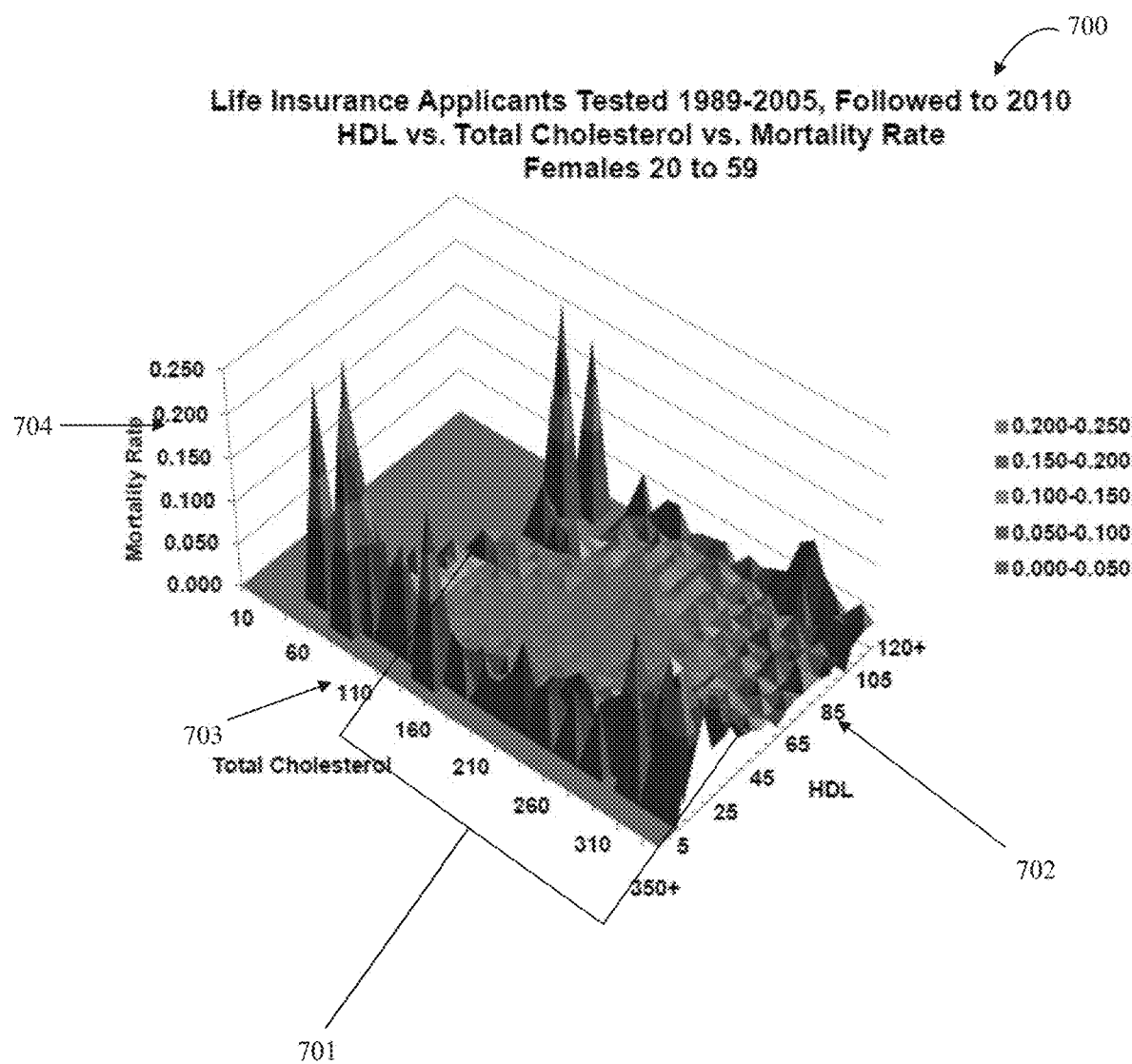
FIG. 7 shows an exemplary 3D graphic map as would be generated by the systems and methods described herein that represents three health or risk parameters taken from a population of individuals.

FIG. 7 shows an exemplary 3D graphic map 700, as would be generated by the systems and methods described herein, that represents three health or risk parameters taken from a population of individuals. The graphic map 700 represents the same HDL and total cholesterol values as the graphic map 300, where in the graphic map 700, HDL is on an axis 702 and total cholesterol is on axis 703. In the graphic map 700 the axis 704 represents the mortality rate (or other adverse health outcome risk) associated with the joint HDL and total cholesterol values. Area 701 of the graphic map 700 represents an area where the mortality rate (or other adverse health outcome risk) is the lowest and it resembles a valley among the peaks that surround it. When compared with the graphic map 300 of FIG. 3, the areas 301 and 701 have overlap, where it appears as the area 701 matches the area of the highest population distribution or "footprint" of the area 301.

In some embodiments, the upper and lower bounds of a reference interval are either equal to or determined by the outer bounds of the region 701 of the graphic map 700. The outer bounds of the area 700, in some embodiments, are determined by a computer program that computes the mortality rates in area 701. In some embodiments, the beginning and end points of the area where the calculated percentages of mortality/adverse health outcome rates are lowest either are or determine the reference interval for HDL (or any other health or risk parameter value represented by axis 702). In some embodiments, the beginning and end points of area where the calculated percentages of mortality/adverse health outcomes are lowest in 701 either are or determine the reference interval for total cholesterol (or any other health or risk parameter value represented by axis 703). In some embodiments, the beginning and end points of area where the calculated percentages of mortality/adverse health outcomes are lowest in 701 either are or determine the reference interval jointly for HDL (or any other health or risk parameter value represented by axis 702) and total cholesterol (or any other health or risk parameter value represented by axis 703).

In some embodiments of the systems and methods described herein a computer program is configured to analyze and/or compare an area of widest distribution of health or risk parameter values 301 in a first graphic map 300 and a valley 701 in a second graphic map 700. In some embodiments, a valley 701 in a second graphic map is overlaid onto the area of widest distribution of health or risk parameter values 301 in the first graphic map 300, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 301 of graphic map 300 and the valley 701 of graphic map 700. The outer bounds of the area of overlap, in some embodiments, is determined by a computer program that compares the areas with the highest percentages of population in 301 against the areas with the lowest mortality/adverse health outcome rates in 701. In some embodiments, the beginning and end points of the area with the lowest mortality/adverse health outcomes in 701 are or determine the reference interval for HDL (or any other health or risk parameter value represented by axis 702). In some embodiments, the beginning and end points of the area with the lowest mortality/adverse health outcomes in 701 either are or determine the reference interval for total cholesterol (or any other health or risk parameter value represented by axis 703). In some embodiments, the beginning and end points of the area with the lowest mortality/adverse health outcomes in 701 either are or determine the reference interval jointly for HDL (or any other health or risk parameter value represented by axis 702) and total cholesterol (or any other health or risk parameter value represented by axis 703).

Figure 8:
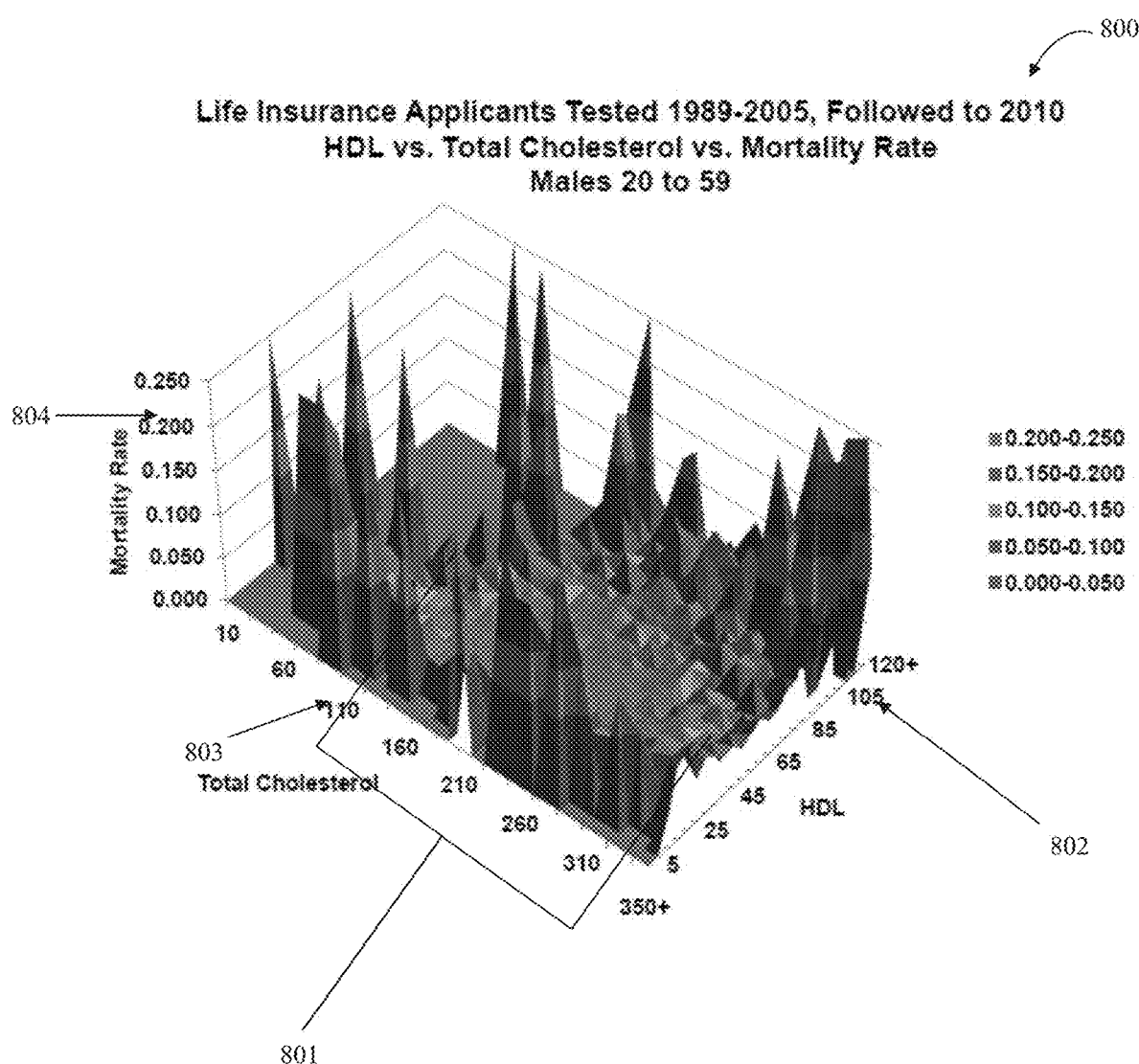
FIG. 8 shows an exemplary 3D graphic map as would be generated by the systems and methods described herein that represents three health or risk parameters taken from a population of individuals.

FIG. 8 shows an exemplary 3D graphic map 800, as would be generated by the systems and methods described herein, that represents three health or risk parameters taken from a population of individuals. The graphic map 800 represents the same HDL and total cholesterol values as the graphic map 300, where in the graphic map 800, HDL is on an axis 802 and total cholesterol is on axis 803. In the graphic map 800 the axis 804 represents the mortality rate (or other adverse health outcome risk) associated with the joint HDL and total cholesterol values. Area 801 of the graphic map 800 represents an area where the mortality rate (or other adverse health outcome risk) is the lowest and it resembles a valley among the peaks that surround it. When compared with the graphic map 400 of FIG. 4, the areas 401 and 801 have overlap, where it appears as the area in 801 that matches the area of the highest population distribution or "footprint" in 401.

In some embodiments, the upper and lower bounds of a reference interval are either equal to or determined by the outer bounds of the region 801 of the graphic map 800. The outer bounds of the area 800, in some embodiments, are determined by a computer program that compares the areas with the highest percentages of population in 401 against the areas with the lowest mortality/adverse health outcome rate in 801. In some embodiments, the beginning and end points of the area with the lowest mortality/adverse health outcomes in 801 either are or determine the reference interval for HDL (or any other health or risk parameter value represented by axis 802). In some embodiments, the beginning and end points of the area with the lowest mortality/adverse health outcomes in 801 either are or determine the reference interval for total cholesterol (or any other health or risk parameter value represented by axis 803). In some embodiments, the beginning and end points of the area with the lowest mortality/adverse health outcomes in 801 either are or determine the reference interval jointly for HDL (or any other health or risk parameter value represented by axis 802) and total cholesterol (or any other health or risk parameter value represented by axis 803).

In some embodiments of the systems and methods described herein a computer program is configured to analyze and/or compare an area of widest distribution of health or risk parameter values 401 in a first graphic map 400 and a valley 801 in a second graphic map 800. In some embodiments, a valley 801 in a second graphic map is overlaid onto the area of widest distribution of health or risk parameter values 401 in the first graphic map 400, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 401 of graphic map 400 and the valley 801 of graphic map 800. The outer bounds of the area of overlap, in some embodiments, is determined by a computer program that compares the areas with the highest percentages of population in 401 against the areas with the lowest mortality/adverse health outcome rates in 801. In some embodiments, the beginning and end points of the area with the lowest mortality/adverse health outcomes in 801 either are or determine the reference interval for HDL (or any other health or risk parameter value represented by axis 802). In some embodiments, the beginning and end points of area with the lowest mortality/adverse health outcomes in 801 either are or determine the reference interval for total cholesterol (or any other health or risk parameter value represented by axis 803). In some embodiments, the beginning and end points of area with the lowest mortality/adverse health outcomes in 801 either are or determine the reference interval jointly for HDL (or any other health or risk parameter value represented by axis 802) and total cholesterol (or any other health or risk parameter value represented by axis 803).

Figure 9:
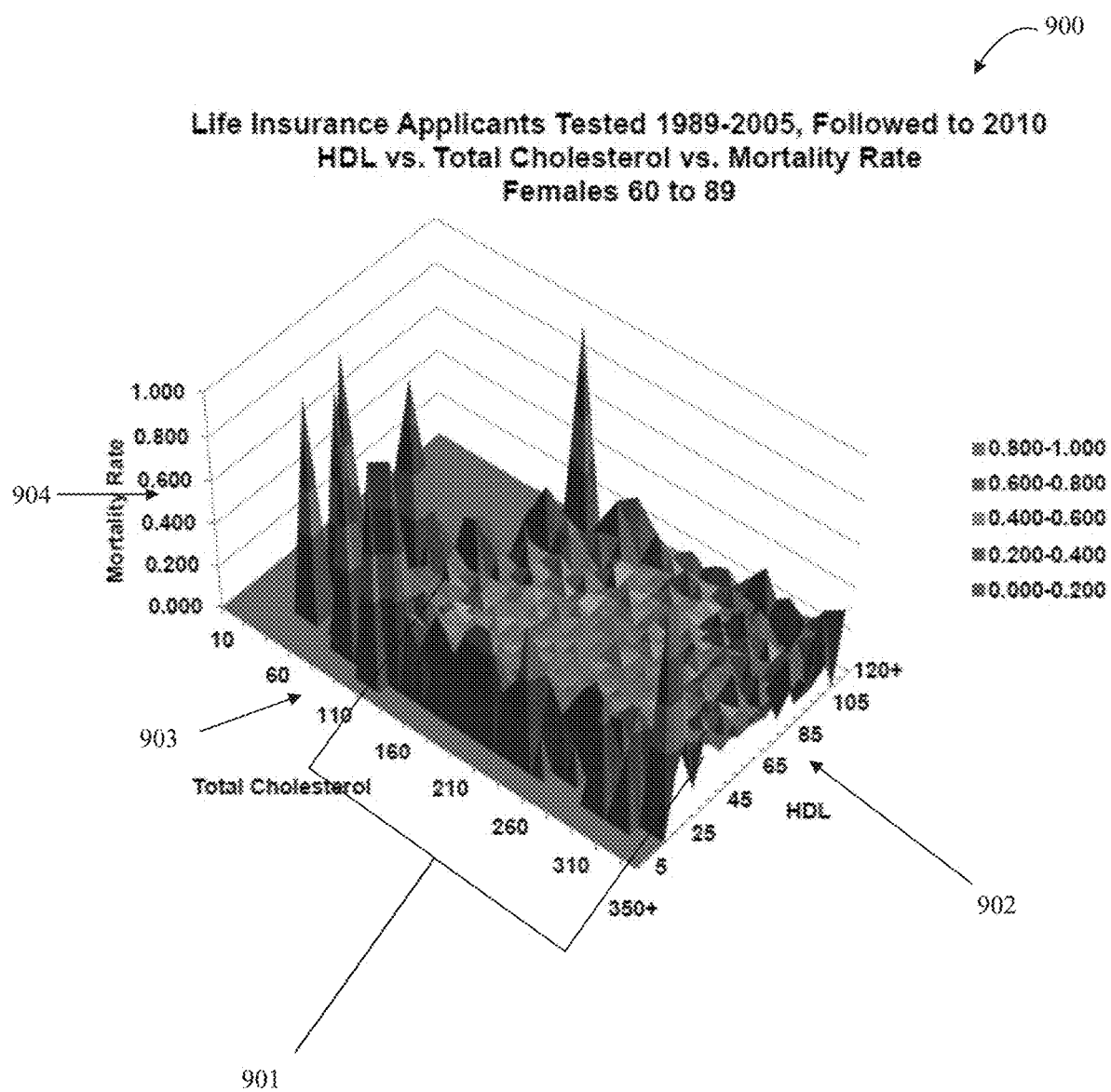
FIG. 9 shows an exemplary 3D graphic map as would be generated by the systems and methods described herein that represents three health or risk parameters taken from a population of individuals.

FIG. 9 shows an exemplary 3D graphic map 900, as would be generated by the systems and methods described herein, that represents three health or risk parameters taken from a population of individuals. The graphic map 900 represents the same HDL and total cholesterol values as the graphic map 500, where in the graphic map 900, HDL is on an axis 902 and total cholesterol is on axis 903. In the graphic map 900 the axis 904 represents the mortality rate (or other adverse health outcome risk) associated with the joint HDL and total cholesterol values. Area 901 of the graphic map 900 represents an area where the mortality rate (or other adverse health outcome risk) is the lowest and it resembles a valley among the peaks that surround it. When compared with the graphic map 500 of FIG. 5, the areas 501 and 901 have overlap, where it appears in 901 that matches the area of the highest population distribution or "footprint" in 501.

In some embodiments, the upper and lower bounds of a reference interval are either equal to or determined by the outer bounds of the region 901 of the graphic map 900. The outer bounds of the area 900, in some embodiments, are determined by a computer program that compares the areas with the highest percentages of population in 501 against the areas with the lowest mortality/adverse health outcome rate in 901. In some embodiments, the beginning and end points of the area with the lowest mortality/adverse health outcomes in 901 either are or determine the reference interval for HDL (or any other health or risk parameter value represented by axis 902). In some embodiments, the beginning and end points of the area with the lowest mortality/adverse health outcomes in 901 either are or determine the reference interval for total cholesterol (or any other health or risk parameter value represented by axis 903). In some embodiments, the beginning and end points of the area with the lowest mortality/adverse health outcomes in 901 either are or determine the reference interval jointly for HDL (or any other health or risk parameter value represented by axis 902) and total cholesterol (or any other health or risk parameter value represented by axis 903).

In some embodiments of the systems and methods described herein a computer program is configured to analyze and/or compare an area of widest distribution of health or risk parameter values 501 in a first graphic map 500 and a valley 901 in a second graphic map 900. In some embodiments, a valley 901 in a second graphic map is overlaid onto the area of widest distribution of health or risk parameter values 501 in the first graphic map 500, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 501 of graphic map 500 and the valley 901 of graphic map 900. The outer bounds of the area of overlap, in some embodiments, is determined by a computer program that compares the areas with the highest percentages of population in 501 against the areas with the lowest mortality/adverse health outcome rate in 901. In some embodiments, the beginning and end points of the area with the lowest mortality/adverse health outcomes in 901 either are or determine the reference interval for HDL (or any other health or risk parameter value represented by axis 902). In some embodiments, the beginning and end points of the area with the lowest mortality/adverse health outcomes in 901 either are or determine the reference interval for total cholesterol (or any other health or risk parameter value represented by axis 903). In some embodiments, the beginning and end points of the area with the lowest mortality/adverse health outcomes in 901 either are or determine the reference interval jointly for HDL (or any other health or risk parameter value represented by axis 902) and total cholesterol (or any other health or risk parameter value represented by axis 903).

Figure 10:
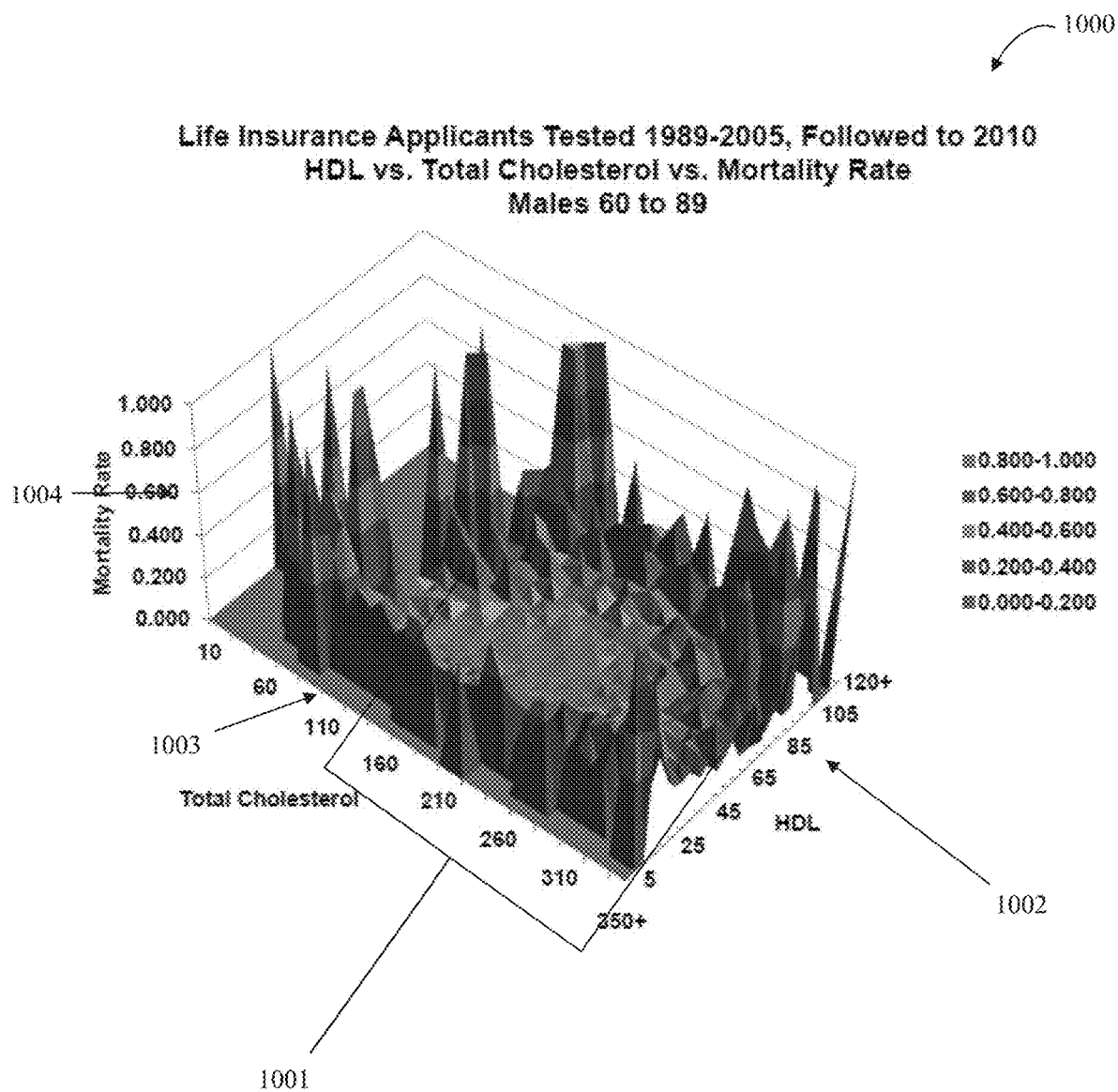
FIG. 10 shows an exemplary 3D graphic map as would be generated by the systems and methods described herein that represents three health or risk parameters taken from a population of individuals.

FIG. 10 shows an exemplary 3D graphic map 1000, as would be generated by the systems and methods described herein, that represents three health or risk parameters taken from a population of individuals. The graphic map 1000 represents the same HDL and total cholesterol values as the graphic map 300, where in the graphic map 1000, HDL is on an axis 1002 and total cholesterol is on axis 1003. In the graphic map 1000 the axis 1004 represents the mortality rate (or other adverse health outcome risk) associated with the joint HDL and total cholesterol values. Area 1001 of the graphic map 1000 represents an area where the mortality rate (or other adverse health outcome risk) is the lowest and it resembles a valley among the peaks that surround it. When compared with the graphic map 600 of FIG. 6, the areas 601 and 1001 have overlap, in that 1001 matches the area of the highest population distribution or "footprint" in 601.

In some embodiments, the upper and lower bounds of a reference interval are either equal to or determined by the outer bounds of the region 1001 of the graphic map 1000. In some embodiments, the beginning and end points of the area with the lowest mortality/adverse health outcomes in 1001 either are or determine the reference interval for HDL (or any other health or risk parameter value represented by axis 1002). In some embodiments, the beginning and end points area with the lowest mortality/adverse health outcomes in 1001 either are or determine the reference interval for total cholesterol (or any other health or risk parameter value represented by axis 1003). In some embodiments, the beginning and end points area with the lowest mortality/adverse health outcomes in 1001 either are or determine the reference interval jointly for HDL (or any other health or risk parameter value represented by axis 1002) and total cholesterol (or any other health or risk parameter value represented by axis 1003).

In some embodiments of the systems and methods described herein a computer program is configured to analyze and/or compare an area of widest distribution of health or risk parameter values 601 in a first graphic map 600 and a valley 1001 in a second graphic map 1000. In some embodiments, a valley 1001 in a second graphic map is overlaid onto the area of widest distribution of health or risk parameter values 601 in the first graphic map 600, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 601 of graphic map 600 and the valley 1001 of graphic map 1000. The outer bounds of the area of overlap, in some embodiments, is determined by a computer program that compares the areas with the highest percentages of population in 601 against the areas with the lowest mortality/adverse health outcome rate in 1001. In some embodiments, the beginning and end points of the area with the lowest mortality/adverse health outcomes in 1002 either are or determine the reference interval for HDL (or any other health or risk parameter value represented by axis 1002). In some embodiments, the beginning and end points of the area with the lowest mortality/adverse health outcomes in 1003 either are or determine the reference interval for total cholesterol (or any other health or risk parameter value represented by axis 1003). In some embodiments, the beginning and end points of the area with the lowest mortality/adverse health outcomes in 1003 either are or determine the reference interval jointly for HDL (or any other health or risk parameter value represented by axis 1002) and total cholesterol (or any other health or risk parameter value represented by axis 1003).

Figure 11:
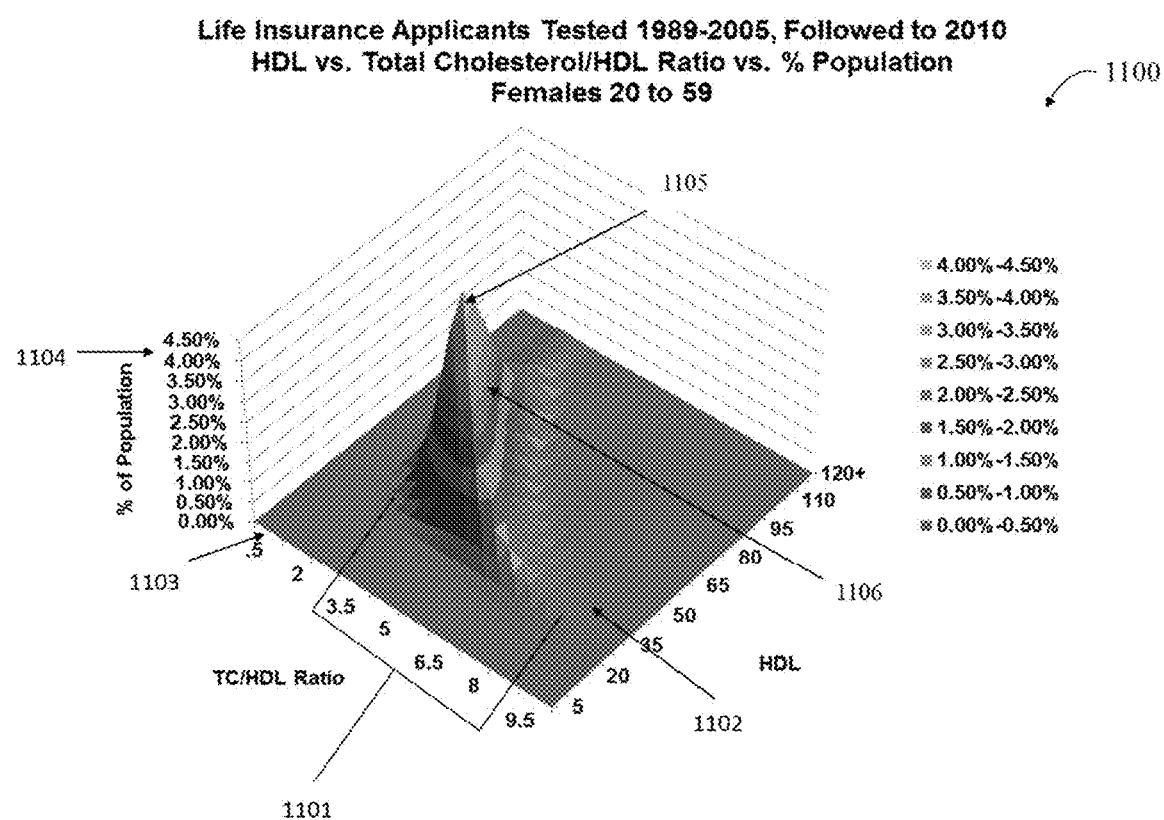
FIG. 11 shows an exemplary 3D graphic map as would be generated by the systems and methods described herein that represents three health or risk parameters taken from a population of individuals.

FIG. 11 shows an exemplary 3D graphic map 1100, as would be generated by the systems and methods described herein, that represents three health or risk parameters taken from a population of individuals. In the 3D graphic map, the health or risk parameters were taken from a large population study of 100,000 or more individuals. The data mapped in the 3D graphic map comprises data collected from females between the ages of 20-59. Specifically, the data comprises the HDL and total cholesterol/HDL ratios for each individual. As shown in FIG. 11, HDL values are represented on a first axis 1102 where the individual HDL values are divided into groups of 5 value units. For example, one HDL group contains HDL values from 25-29 units of HDL so that any individual with an HDL of, for example, 26 is placed in this group. Similarly, total cholesterol/HDL ratio is represented on a first axis 1103 where the individual total cholesterol/HDL ratios are divided into groups of 0.5 value units. For example, one ratio group ranges from 9.5-10 units of total cholesterol/HDL so that any individual with a total cholesterol/HDL ratio, for example, 9.9 is placed in this group. A percentage of the population is represented on a third axis 1104. These three health or risk parameter data points—HDL, total cholesterol/HDL ratio, and percent of population—are mapped in a 3D graphic map 1100, wherein each individual's HDL and total cholesterol/HDL ratio values are placed in their respective groups in the x-y plane and the percentage of the population that these groups represent is graphed on the z-axis. Mapping the values in the way creates a three dimensional representation of two joint health or risk parameter values (i.e. HDL level joined with total cholesterol/HDL ratio) along with the percentage of the population that the joint values represent. For example, individuals with an HDL of 45 and a total cholesterol (TC)/HDL ratio of 4 would be at 1.64% of the total population from which data was taken. A region 1101 of the 3D graphic map represents an area of the map having the widest distribution of HDL and TC/HDL values. A region 1105 represents 4.00%-4.50% of the population shown on the graphic map and has the least amount of distribution. A region 1106 represents 2.00%-2.50% of the population shown on the graphic map and has an intermediate amount of distribution.

In some embodiments, the upper and lower bounds of a reference interval are either equal to or determined by the outer bounds of the region 1101 of the graphic map 1000. The outer bounds of the area, in some embodiments, are determined by a computer program that computes the percentages of population within area 1101. In some embodiments, the beginning and end points of the area where the calculated percentages of population are highest either are or determine the reference interval for HDL (or any other population parameter value represented by axis 1102). In some embodiments, the beginning and end points of the area where the calculated percentages of population are highest either are or determine the reference interval for total cholesterol/HDL ratio (or any other health or risk parameter value represented by axis 1103). In some embodiments, the beginning and end points of the area where the calculated percentages of population are highest either are or determine the reference interval jointly for HDL (or any other population parameter value represented by axis 1102) and total cholesterol/HDL ratio (or any other health or risk parameter value represented by axis 1103).

Figure 12:
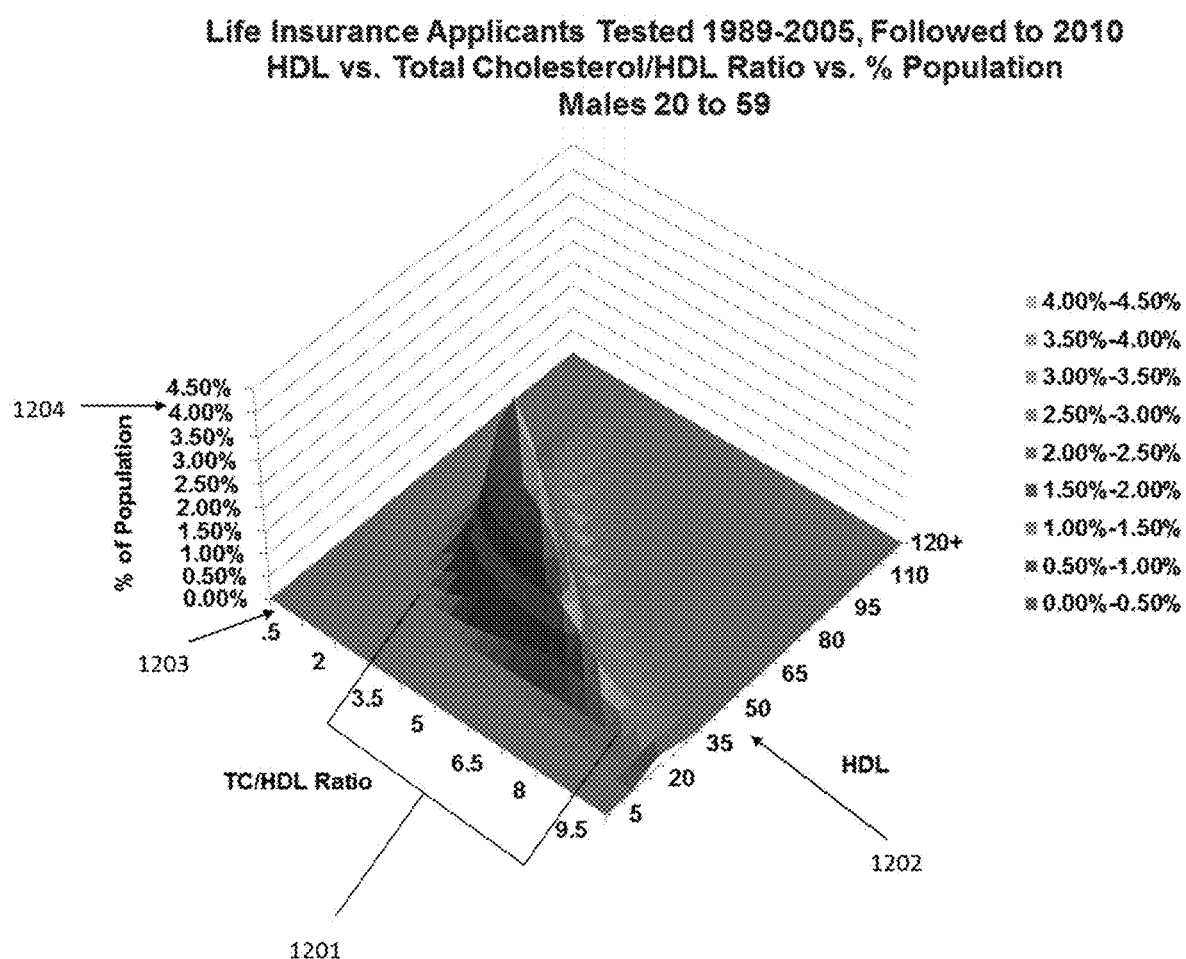
FIG. 12 shows an exemplary 3D graphic map as would be generated by the systems and methods described herein that represents three health or risk parameters taken from a population of individuals.

FIG. 12 shows an exemplary 3D graphic map 1200, as would be generated by the systems and methods described herein, that represents three health or risk parameters taken from a population of individuals. In the 3D graphic map, the health or risk parameters were taken from a large population study of 100,000 or more individuals. The data mapped in the 3D graphic map comprises data collected from males between the ages of 20-59. Specifically, the data comprises the HDL and total cholesterol (TC)/HDL ratios for each individual. As shown in FIG. 12, HDL values are represented on a first axis 1202 where the individual HDL values are divided into groups of 5 value units. For example, one HDL group contains HDL values from 25-29 units of HDL so that any individual with an HDL of, for example, 26 is placed in this group. Similarly, total cholesterol/HDL ratios are represented on a first axis 1203 where the range of total cholesterol/HDL ratios are divided into groups of 0.5 value units. A percentage of the population is represented on a third axis 1204. The health or risk parameter data points are mapped in 3D graphic map 1200, wherein each individual's HDL and TC/HDL values are placed in their respective groups in the x-y plane and the percentage of the population that these groups represent is graphed on the z-axis. Mapping the values in the way creates a three dimensional representation of two joint health or risk parameter values (i.e. HDL level joined with Total cholesterol/HDL ratio) along with the percentage of the population that the joint values represent. For example, individuals with an HDL of 45 and a TC/HDL ratio of 4.5 would be between 1.50% and 2.00% of the total population from which data was taken. A region 1201 of the 3D graphic map represents an area of the map having the widest distribution of health or risk parameter values, e.g., HDL and/or TC/HDL ratio. It is notable that the 3D graphic map 1100 (as shown in FIG. 11) differs in its range of greatest distribution 1101 as compared with the area of greatest distribution 1201 in 3D graphic map 1200. This difference in the appearance of between graphic map 1100 and graphic map 1200 is presumed to be a result of a difference in sex between the populations (or sub-populations) represented respectively in each of the graphic maps 1100 and 1200. That there is a difference between graphic map 1100 and graphic map 1200, which are both for the same age range, highlights the value of separating data for generating reference intervals by sex. In some cases, a reference interval is determined based on at least a portion of a graphic map where a population distribution is greatest (i.e. ranges 1101 and 1201). Therefore, a difference in population distributions in 3D graphic maps of different age groups may represent a difference in a reference interval between one sex and another. Said yet another way, it is expected, based on the differences between graphic map 1100 and graphic map 1200 that a different reference interval would define a normal HDL value in a male between the age of 20-59 than a female between the age of 20-59.

In some embodiments, the upper and lower bounds of a reference interval are either equal to or determined by the outer bounds of the region 1201 of the graphic map 1200. The outer bounds of the area 1200, in some embodiments, are determined by a computer program that computes the percentages of population within area 1201. In some embodiments, the beginning and end points of area where the calculated percentages of population are highest either are or determine the reference interval for HDL (or any other health or risk parameter value represented by axis 1202). In some embodiments, the beginning and end points of the area where the calculated percentages of population are highest either are or determine the reference interval for total cholesterol/HDL ratio (or any other health or risk parameter value represented by axis 1203). In some embodiments, the beginning and end points of the area where the calculated percentages of population are highest either are or determine the reference interval jointly for HDL (or any other health or risk parameter value represented by axis 1202) and total cholesterol/HDL ratio (or any other health or risk parameter value represented by axis 1203).

Figure 13:
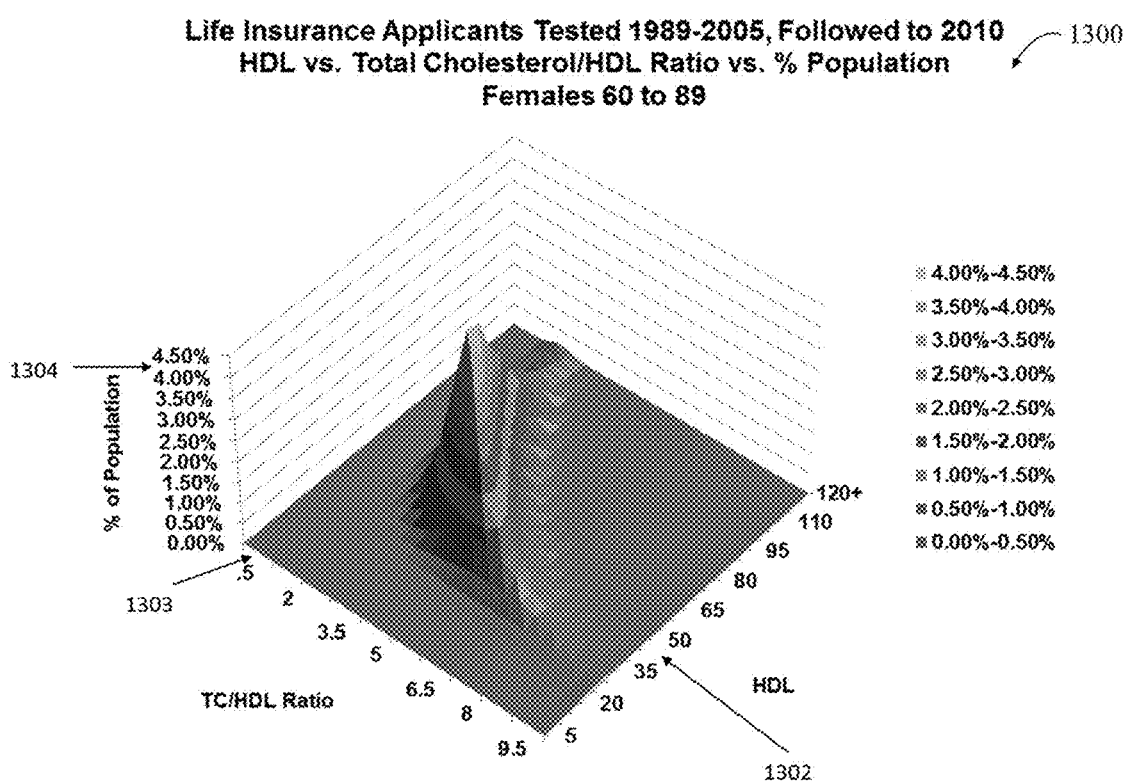
FIG. 13 shows an exemplary 3D graphic map as would be generated by the systems and methods described herein that represents three health or risk parameters taken from a population of individuals.

FIG. 13 shows exemplary 3D graphic map 1300 which is mapped using HDL, TC/HDL, and percent of population data collected from females between the ages of 60-89, along first axis 1302, second axis 1303, and third axis 1304, respectively. A region 1301 of the 3D graphic map represents an area of the map having the widest distribution of HDL and TC/HDL values. A region 1301 of the 3D graphic map 1300 represents an area of the map having the widest distribution of individual health or risk parameter values. It is notable that the 3D graphic map 1100 (as shown in FIG. 11) differs in its range of greatest distribution as compared with the 3D graphic map 1300. This difference in the appearance of between graphic map 1100 and graphic map 1300 is presumed to be a result of a difference in ages between the populations (or sub-populations) represented respectively in each of the graphic map 1100 and 1300. That there is a difference between graphic map 1100 and graphic map 1300, which are both for the same sex, highlights the value of separating data for generating reference intervals by age. In some cases, a reference interval is determined based on portion of a graphic map where a population distribution is greatest in either 1101 or 1301. Therefore, a difference in population distributions in 3D graphic maps of different age groups may represent a difference in a reference interval between one age group and another. Said yet another way, it is expected, based on the differences between graphic map 1100 and graphic map 1300 that a different reference interval would define a normal HDL value in a female between the age of 20-59 than a female between the age of 60-89.

In some embodiments, the upper and lower bounds of a reference interval are either equal to or determined by the outer bounds of the region 1301. The outer bounds of the area, in some embodiments, are determined by a computer program that computes the percentages of population within area 1301. In some embodiments, the beginning and end points of the area where the calculated percentages of population are highest either are or determine the reference interval for HDL (or any other population parameter value represented by axis 1302). In some embodiments, the beginning and end points of area where the calculated percentages of population are highest in 1303 either are or determine the reference interval for total cholesterol/HDL ratio (or any other population parameter value represented by axis 1303). In some embodiments, the beginning and end points of area where the calculated percentages of population are highest in 1303 either are or determine the reference interval jointly for HDL (or any other population parameter value represented by axis 1302) and total cholesterol/HDL ratio (or any other population parameter value represented by axis 1303).

Figure 14:
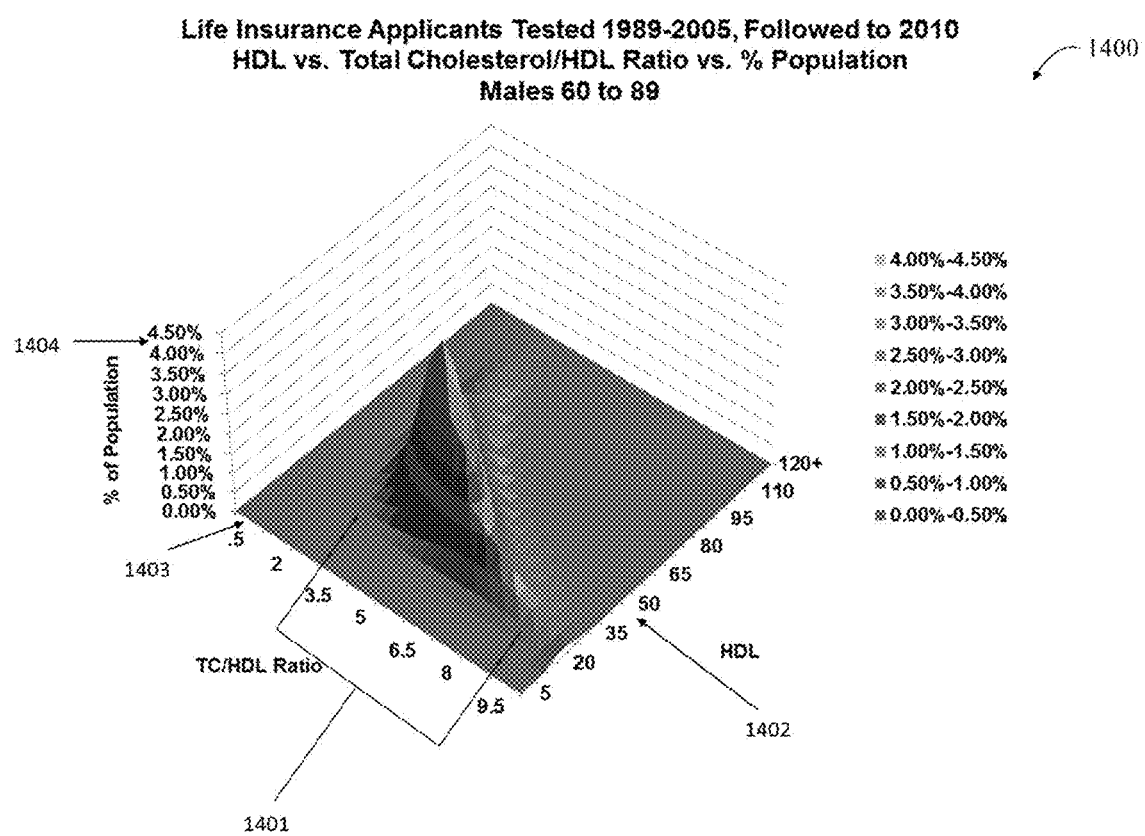
FIG. 14 shows an exemplary 3D graphic map as would be generated by the systems and methods described herein that represents three health or risk parameters taken from a population of individuals.

FIG. 14 shows an exemplary 3D graphic map 1400, as would be generated by the systems and methods described herein, that represents three health or risk parameters taken from a population of individuals. In the 3D graphic map 1400, the health or risk parameters were taken from a large population study of 100,000 or more individuals. The data mapped in the 3D graphic map comprises data collected from males between the ages of 60-89. Specifically, the data comprises the HDL and total cholesterol/HDL ratio for each individual. As shown in FIG. 14, HDL values are represented on a first axis 1402 where the individual HDL values are divided into groups of 5 value units. Similarly, total cholesterol/HDL ratios are represented on a second axis 1403 where the individual total cholesterol/HDL ratios are divided into groups of 0.5 value units. A percentage of the population is represented on a third axis 1404. The health or risk parameter data points are mapped in 3D graphic map 1400, wherein each individual's HDL and TC/HDL ratio values are placed in their respective groups in the x-y plane and the percentage of the population that these groups represent is graphed on the z-axis. Mapping the values in the way creates a three dimensional representation of two joint health or risk parameter values (i.e. HDL level joined with TC/HDL ratio) along with the percentage of the population that the joint values represent. A region 1401 of the 3D graphic map 1400 represents an area of the map 1400 having the widest distribution of individual values. It is notable that the 3D graphic map 1200 (as shown in FIG. 12) differs in its range of greatest distribution as compared with the 3D graphic map 1400. This difference in the appearance of between graphic map 1200 and graphic map 1400 is presumed to be a result of a difference in ages between the populations (or sub-populations) represented respectively in each of the graphic map 400 and 600. That there is a difference between graphic map 1200 and graphic map 1400, which are both for the same sex, highlights the value of separating data for generating reference intervals by age. In some cases, a reference interval is determined based on portion of a graphic map where a population distribution is greatest (i.e. regions 1201 and 1401). Therefore, a difference in population distributions in 3D graphic maps of different age groups may represent a difference in a reference interval between one age group and another. Said yet another way, it is expected, based on the differences between graphic map 1200 and graphic map 1400 that a different reference interval would define a normal HDL value in a male between the age of 20-59 and a male between the age of 60-89.

In some embodiments, the upper and lower bounds of a reference interval are either equal to or determined by the outer bounds of the region 1401 of the graphic map 1400. The outer bounds of the area, in some embodiments, are determined by a computer program that computes the percentages of population within area 1401. In some embodiments, the beginning and end points of the area where the calculated percentages of population are highest in either are or determine the reference interval for HDL (or any other population parameter value represented by axis 1402). In some embodiments, the beginning and end points of the area where the calculated percentages of population are highest in either are or determine the reference interval for total cholesterol/HDL ratio (or any other health or risk parameter represented on the axis 1403). In some embodiments, the beginning and end points of the area where the calculated percentages of population are highest in either are or determine the reference interval jointly for HDL (or any other population parameter value represented by axis 1402) and total cholesterol/HDL ratio (or any other health or risk parameter represented on the axis 1403).

Figure 15:
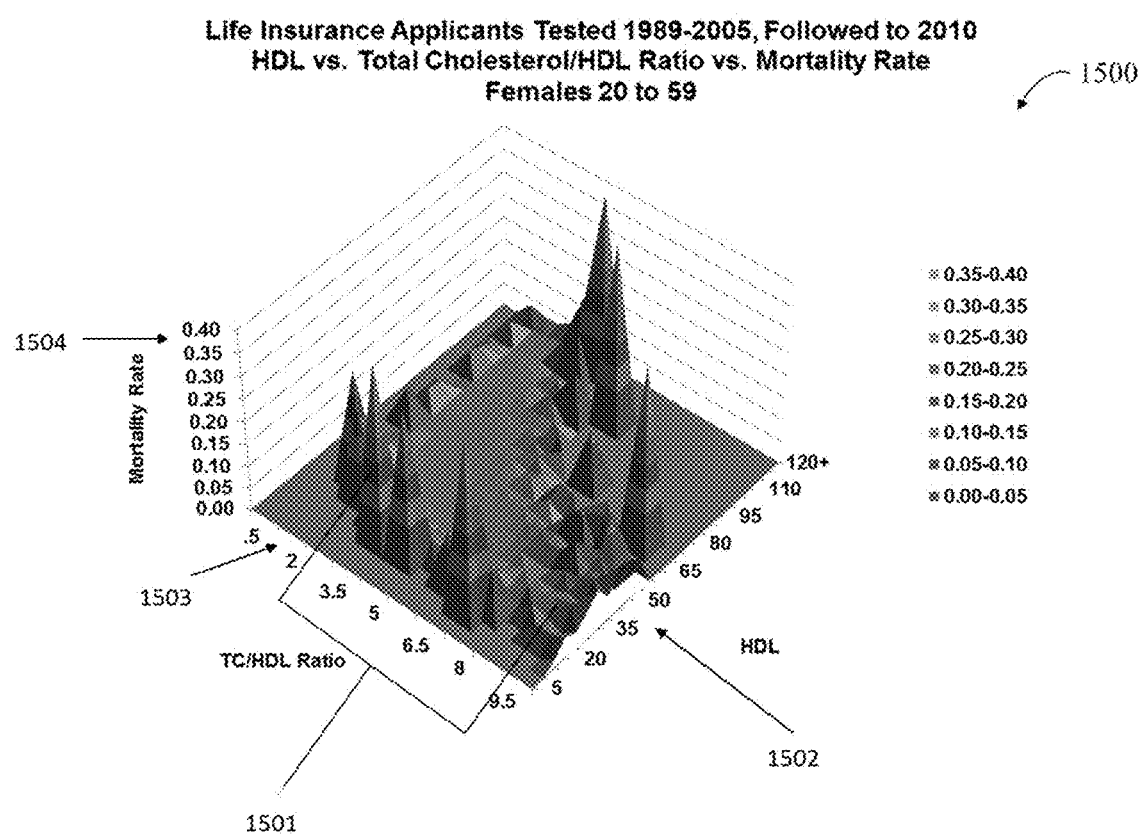
FIG. 15 shows an exemplary 3D graphic map as would be generated by the systems and methods described herein that represents three health or risk parameters taken from a population of individuals.

FIG. 15 shows an exemplary 3D graphic map 1500, as would be generated by the systems and methods described herein, that represents three health or risk parameters taken from a population of individuals. The graphic map 1500 represents the same HDL and total cholesterol/HDL ratio as the graphic map 1100, where in the graphic map 1500, HDL is on an axis 1502 and total cholesterol/HDL ratio is on axis 1503. The axis 1504 represents the mortality rate (or other adverse health outcome risk) associated with the joint HDL and total cholesterol/HDL ratio values. Area 1501 of the graphic map represents an area where the mortality rate (or other adverse health outcome risk) is the lowest and it resembles a valley among the peaks that surround it. When compared with the graphic map 1100 of FIG. 11, the areas 1101 and 1501 have overlap, where it appears as the area 1501 matches the area of the highest population distribution or "footprint" of the area 1501.

In some embodiments, the upper and lower bounds of a reference interval are either equal to or determined by the outer bounds of the region 1501 of the graphic map 1500. The outer bounds of the area, in some embodiments, are determined by a computer program that computes the mortality rates in area 1501. In some embodiments, the beginning and end points of the area where the calculated percentages of mortality/adverse health outcome rates are lowest either are or determine the reference interval for HDL (or any other health or risk parameter value represented by axis 1502). In some embodiments, the beginning and end points of area where the calculated percentages of mortality/adverse health outcomes are lowest in 1501 either are or determine the reference interval for total cholesterol/HDL ratio (or any other health or risk parameter value represented by axis 1503). In some embodiments, the beginning and end points of area where the calculated percentages of mortality/adverse health outcomes are lowest in 1501 either are or determine the reference interval jointly for HDL (or any other health or risk parameter value represented by axis 1502) and total cholesterol/HDL ratio (or any other health or risk parameter value represented by axis 1503).

In some embodiments of the systems and methods described herein a computer program is configured to analyze and/or compare an area of widest distribution of health or risk parameter values 1101 in a first graphic map 1100 and a valley 1501 in a second graphic map 1500. In some embodiments, a valley 1501 in a second graphic map is overlaid onto the area of widest distribution of health or risk parameter values 1101 in the first graphic map 1100, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 1101 of graphic map 1100 and the valley 1501 of graphic map 1500. The outer bounds of the area of overlap, in some embodiments, is determined by a computer program that compares the areas with the highest percentages of population in 1101 against the areas with the lowest mortality/adverse health outcome rate in 1501. In some embodiments, the beginning and end points of the area with the lowest mortality/adverse health outcomes in 1501 are or determine the reference interval for HDL (or any other health or risk parameter value represented by axis 1502). In some embodiments, the beginning and end points of the area with the lowest mortality/adverse health outcomes in 1501 either are or determine the reference interval for total cholesterol/HDL ratio (or any other health or risk parameter value represented by axis 1503). In some embodiments, the beginning and end points of the area with the lowest mortality/adverse health outcomes in 1501 either are or determine the reference interval jointly for HDL (or any other health or risk parameter value represented by axis 1502) and total cholesterol/HDL ratio (or any other health or risk parameter value represented by axis 1503).

Figure 16:
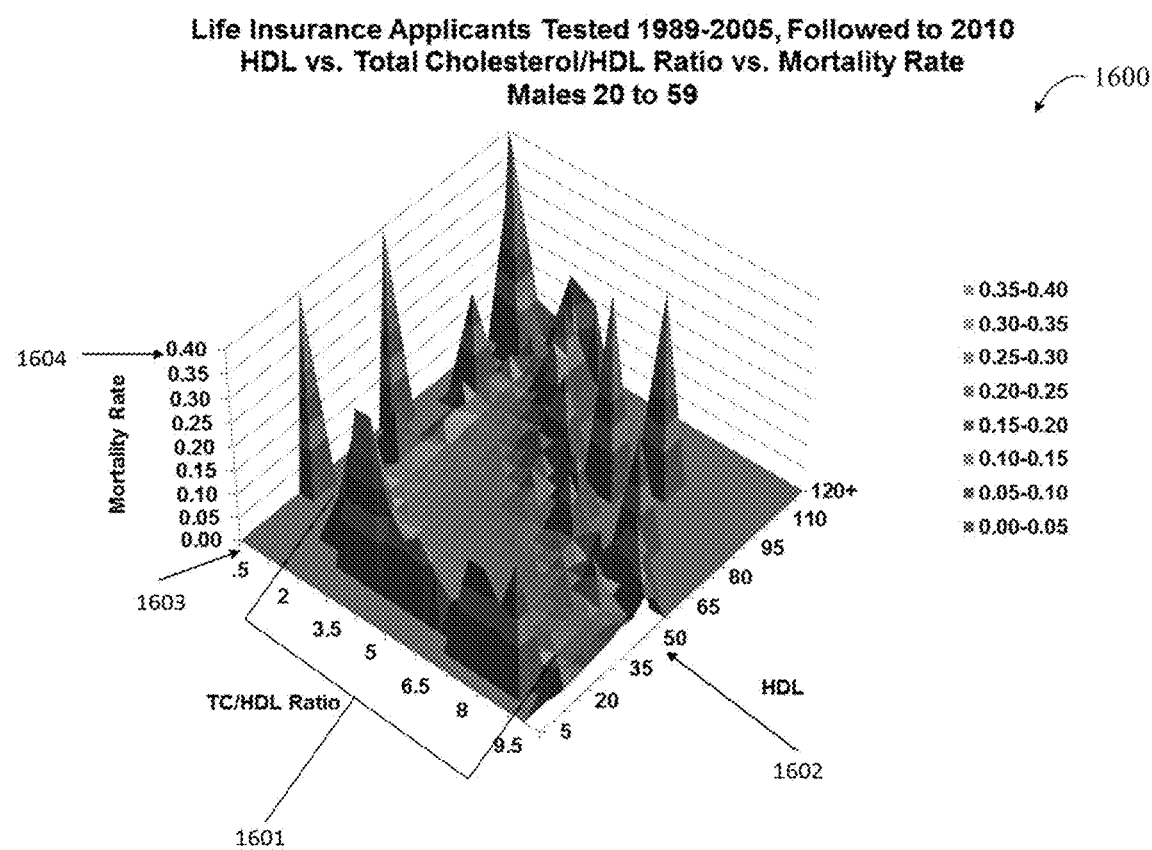
FIG. 16 shows an exemplary 3D graphic map as would be generated by the systems and methods described herein that represents three health or risk parameters taken from a population of individuals.

FIG. 16 shows an exemplary 3D graphic map 1600, as would be generated by the systems and methods described herein, that represents three health or risk parameters taken from a population of individuals. The graphic map 1600 represents the same HDL and total cholesterol/HDL ratio as the graphic map 1200, where in the graphic map 1600, HDL is on an axis 1602 and total cholesterol/HDL ratio is on axis 1603. The axis 1604 represents the mortality rate (or other adverse health outcome risk) associated with the joint HDL and total cholesterol/HDL ratio values. Area 1601 of the graphic map 1600 represents an area where the mortality rate (or other adverse health outcome risk) is the lowest and it resembles a valley among the peaks that surround it. When compared with the graphic map 1200 of FIG. 12, the areas 1201 and 1601 have overlap, where it appears as the area in 1601 matches the area of the highest population distribution or "footprint" in 1201.

In some embodiments, the upper and lower bounds of a reference interval are either equal to or determined by the outer bounds of the region 1601 of the graphic map 1600. The outer bounds of the area, in some embodiments, are determined by a computer program that compares the areas with the highest percentages of population in 1201 against the areas with the lowest mortality/adverse health outcome rate in 1601. In some embodiments, the beginning and end points of the area with the lowest mortality/adverse health outcomes in 1601 either are or determine the reference interval for HDL (or any other health or risk parameter value represented by axis 1602). In some embodiments, the beginning and end points of the area with the lowest mortality/adverse health outcomes in 1601 either are or determine the reference interval for total cholesterol/HDL ratio (or any other health or risk parameter value represented by axis 1603). In some embodiments, the beginning and end points of the area with the lowest mortality/adverse health outcomes in 1601 either are or determine the reference interval jointly for HDL (or any other health or risk parameter value represented by axis 1602) and total cholesterol/HDL ratio (or any other health or risk parameter value represented by axis 1603).

In some embodiments of the systems and methods described herein a computer program is configured to analyze and/or compare an area of widest distribution of health or risk parameter values 1201 in a first graphic map 1200 and a valley 1601 in a second graphic map 1600. In some embodiments, a valley 1601 in a second graphic map is overlaid onto the area of widest distribution of health or risk parameter values 1201 in the first graphic map 1200, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 1201 of graphic map 1200 and the valley 1601 of graphic map 1600. The outer bounds of the area of overlap, in some embodiments, is determined by a computer program that compares the areas with the highest percentages of population in 1201 against the areas with the lowest mortality/adverse health outcome rate in 1601. In some embodiments, the beginning and end points of the area with the lowest mortality/adverse health outcomes in 1601 either are or determine the reference interval for HDL (or any other health or risk parameter value represented by axis 1602). In some embodiments, the beginning and end points of area with the lowest mortality/adverse health outcomes in 1601 either are or determine the reference interval for total cholesterol/HDL ratio (or any other health or risk parameter value represented by axis 1603). In some embodiments, the beginning and end points of area with the lowest mortality/adverse health outcomes in 1601 either are or determine the reference interval jointly for HDL (or any other health or risk parameter value represented by axis 1602) and total cholesterol/HDL ratio (or any other health or risk parameter value represented by axis 1603).

Figure 17:
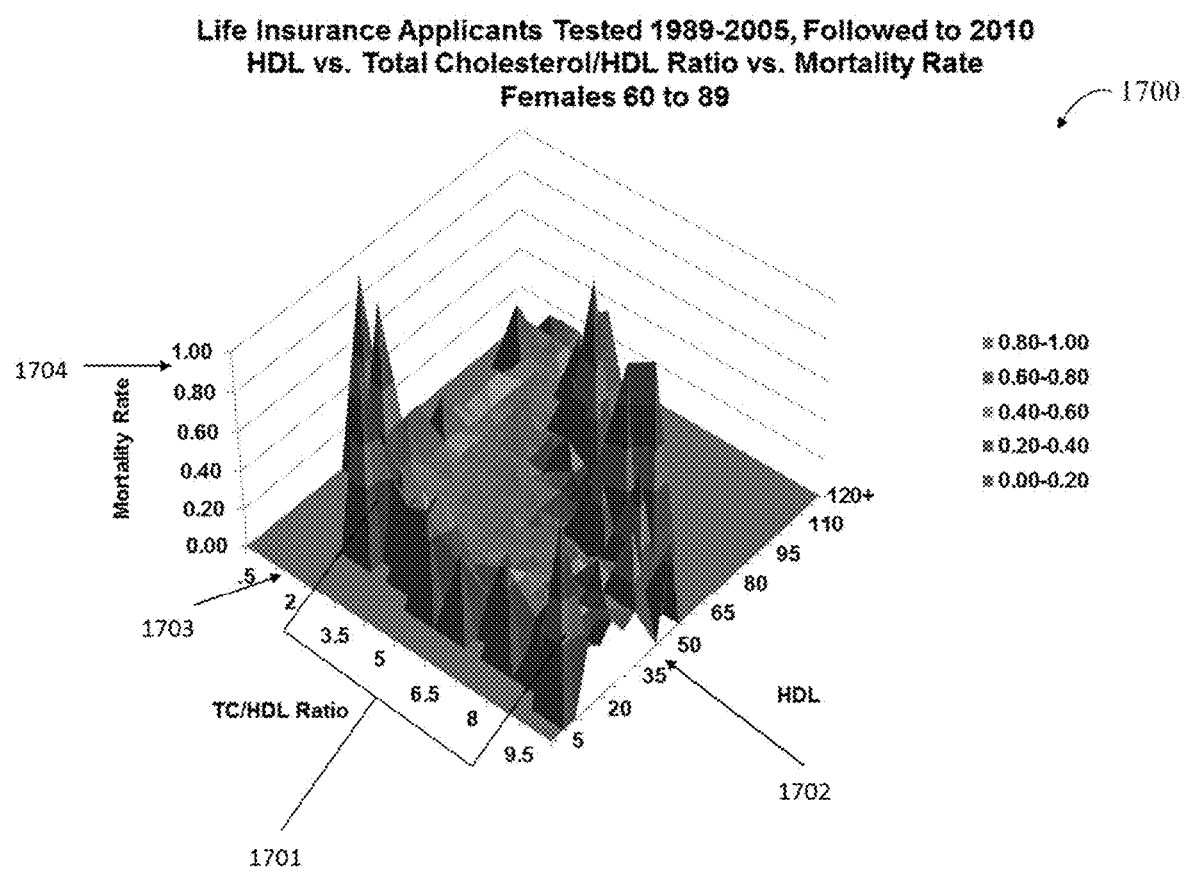
FIG. 17 shows an exemplary 3D graphic map as would be generated by the systems and methods described herein that represents three health or risk parameters taken from a population of individuals.

FIG. 17 shows an exemplary 3D graphic map 1700, as would be generated by the systems and methods described herein, that represents three health or risk parameters taken from a population of individuals. The graphic map 1700 represents the same HDL and total cholesterol/HDL ratio as the graphic map 1300, where in the graphic map 1300, HDL is on an axis 1702 and total cholesterol/HDL ratio is on axis 1703. In the graphic map 1700 the axis 1704 represents the mortality rate (or other adverse health outcome risk) associated with the joint HDL and total cholesterol/HDL ratio values. Area 1701 of the graphic map 1700 represents an area where the mortality rate (or other adverse health outcome risk) is the lowest and it resembles a valley among the peaks that surround it. When compared with the graphic map 1300 of FIG. 13, the areas 1301 and 1701 have overlap, where it appears in 1701 that matches the area of the highest population distribution or "footprint" in 1301.

In some embodiments, the upper and lower bounds of a reference interval are either equal to or determined by the outer bounds of the region 1701 of the graphic map 1700. The outer bounds of the area, in some embodiments, are determined by a computer program that compares the areas with the highest percentages of population in 1301 against the areas with the lowest mortality/adverse health outcome rate in 1701. In some embodiments, the beginning and end points of the area with the lowest mortality/adverse health outcomes in 1701 either are or determine the reference interval for HDL (or any other health or risk parameter value represented by axis 1702). In some embodiments, the beginning and end points of the area with the lowest mortality/adverse health outcomes in 1701 either are or determine the reference interval for total cholesterol/HDL ratio (or any other health or risk parameter value represented by axis 1703). In some embodiments, the beginning and end points of the area with the lowest mortality/adverse health outcomes in 1701 either are or determine the reference interval jointly for HDL (or any other health or risk parameter value represented by axis 1702) and total cholesterol/HDL ratio (or any other health or risk parameter value represented by axis 1703).

In some embodiments of the systems and methods described herein a computer program is configured to analyze and/or compare an area of widest distribution of health or risk parameter values 1301 in a first graphic map 1300 and a valley 1701 in a second graphic map 1700. In some embodiments, a valley 1701 in a second graphic map is overlaid onto the area of widest distribution of health or risk parameter values 1301 in the first graphic map 1300, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 1301 of graphic map 1300 and the valley 1701 of graphic map 1700. The outer bounds of the area of overlap, in some embodiments, is determined by a computer program that compares the areas with the highest percentages of population in 1301 against the areas with the lowest mortality/adverse health outcome rate in 1701. In some embodiments, the beginning and end points of the area with the lowest mortality/adverse health outcomes in 1701 either are or determine the reference interval for HDL (or any other health or risk parameter value represented by axis 1702). In some embodiments, the beginning and end points of the area with the lowest mortality/adverse health outcomes in 1701 either are or determine the reference interval for total cholesterol/HDL ratio (or any other health or risk parameter value represented by axis 1703). In some embodiments, the beginning and end points of the area with the lowest mortality/adverse health outcomes in 1701 either are or determine the reference interval jointly for HDL (or any other health or risk parameter value represented by axis 1702) and total cholesterol/HDL ratio (or any other health or risk parameter value represented by axis 1703).

Figure 18:
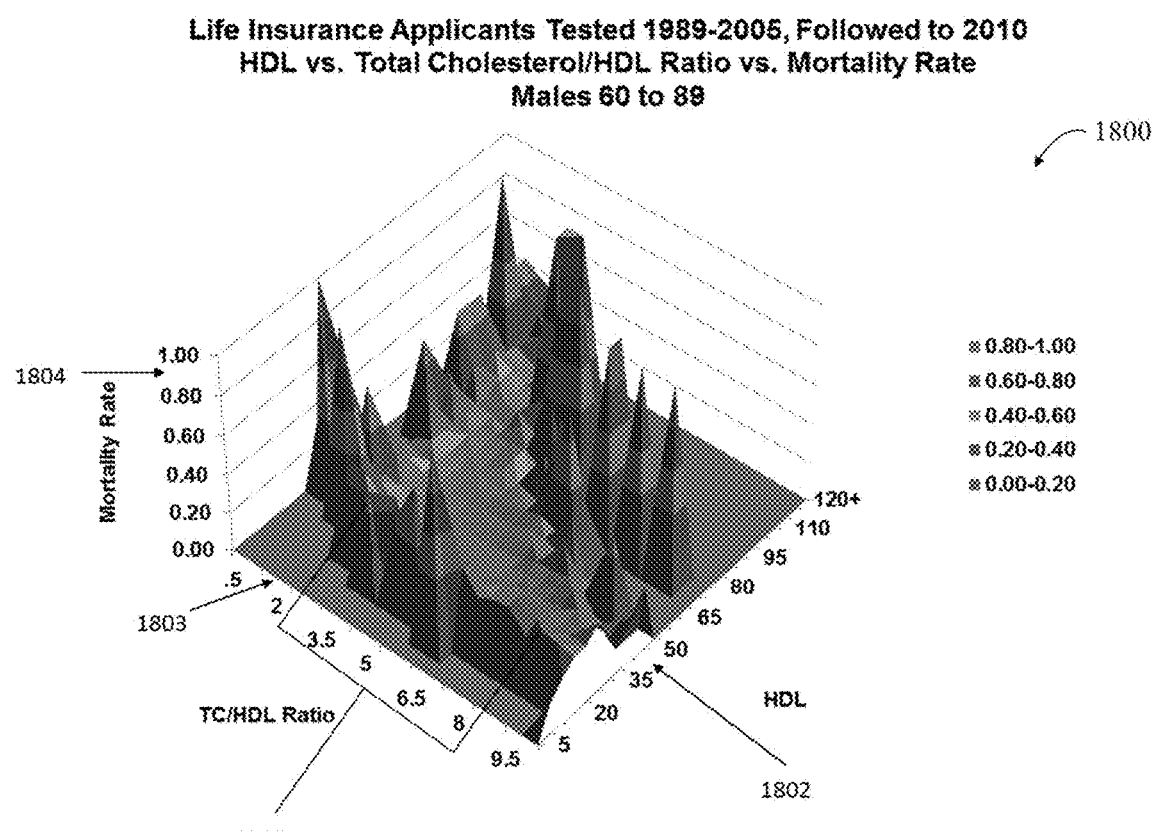
FIG. 18 shows an exemplary 3D graphic map as would be generated by the systems and methods described herein that represents three health or risk parameters taken from a population of individuals.

FIG. 18 shows an exemplary 3D graphic map 1800, as would be generated by the systems and methods described herein, that represents three health or risk parameters taken from a population of individuals. The graphic map 1800 represents the same HDL and total cholesterol/HDL ratio as the graphic map 1100, where in the graphic map 1800, HDL is on an axis 1802 and total cholesterol/HDL ratio is on axis 1803. In the graphic map 1800 the axis 1804 represents the mortality rate (or other adverse health outcome risk) associated with the joint HDL and total cholesterol/HDL ratio values. Area 1801 of the graphic map 1800 represents an area where the mortality rate (or other adverse health outcome risk) is the lowest and it resembles a valley among the peaks that surround it. When compared with the graphic map 1400 of FIG. 14, the areas 1401 and 1801 have overlap, in that 1801 matches the area of the highest population distribution or "footprint" in 1401.

In some embodiments, the upper and lower bounds of a reference interval are either equal to or determined by the outer bounds of the region 1801 of the graphic map 1800. In some embodiments, the beginning and end points of the area with the lowest mortality/adverse health outcomes in 1801 either are or determine the reference interval for HDL (or any other health or risk parameter value represented by axis 1802). In some embodiments, the beginning and end points area with the lowest mortality/adverse health outcomes in 1801 either are or determine the reference interval for total cholesterol/HDL ratio (or any other health or risk parameter value represented by axis 1803). In some embodiments, the beginning and end points area with the lowest mortality/adverse health outcomes in 1801 either are or determine the reference interval jointly for HDL (or any other health or risk parameter value represented by axis 1802) and total cholesterol/HDL ratio (or any other health or risk parameter value represented by axis 1803).

In some embodiments of the systems and methods described herein a computer program is configured to analyze and/or compare an area of widest distribution of health or risk parameter values 1401 in a first graphic map 1400 and a valley 1801 in a second graphic map 1800. In some embodiments, a valley 1801 in a second graphic map is overlaid onto the area of widest distribution of health or risk parameter values 1401 in the first graphic map 1400, and an area of overlap is determined. In some embodiments, the widest bounds of the area of overlap either are or are used to determine the upper and lower bounds of a reference interval. In some embodiments, the upper and lower bounds of a reference interval are either equal to or determined by the outer bounds of the region of overlap of the area of widest distribution of health or risk parameter values 1401 of graphic map 1400 and the valley 1401 of graphic map 1800. The outer bounds of the area of overlap, in some embodiments, is determined by a computer program that compares the areas with the highest percentages of population in 1401 against the areas with the lowest mortality/adverse health outcome rate in 1801. In some embodiments, the beginning and end points of the area with the lowest mortality/adverse health outcomes in 1802 either are or determine the reference interval for HDL (or any other health or risk parameter value represented by axis 1802). In some embodiments, the beginning and end points of the area with the lowest mortality/adverse health outcomes in 1803 either are or determine the reference interval for total cholesterol/HDL ratio (or any other health or risk parameter value represented by axis 1803). In some embodiments, the beginning and end points of the area with the lowest mortality/adverse health outcomes in 1803 either are or determine the reference interval jointly for HDL (or any other health or risk parameter value represented by axis 1802) and total cholesterol/HDL ratio (or any other health or risk parameter value represented by axis 1803).

The systems and methods for generating reference intervals may be used in a wide spectrum of different embodiments, such as non-health care related embodiments. For such embodiments, a reference interval may comprise one or more parameter values that are indicative of existence or absence of a status or occurrence or absence of a particular event, such as a general status or event that is not related to health-care. Such parameter value is, for example, a sensed, measured, or observed value associated with an individual's condition or status. Such parameter value is, for example, a sensed, measured, or observed value associated with the particular event. The individual may be human, a mammal, a living organism, or a non-living object. Such applications can be life insurance, health insurance, fire insurance, hazard insurance, home insurance, auto insurance, travel insurance, flood insurance, business insurance, pet insurance, or any other type of insurances. Non-limiting examples of types of parameter values comprise subjective data, and objective data. Non-limiting examples of objective data include criminal record, education, nationality, residential status, marital status, income range, credit record, health insurance type, health insurance coverage, life insurance type, life insurance coverage, amount of debt, number of speeding tickets, number of accident, possession of a product, possession of a property, or any other objective information of that individual. Non-limiting examples of subjective data include job performance, and satisfactory level about a product, or any other subjective information of or related to the individual. As a non-limiting example, a reference interval may be generated using driving record joined with other parameters to determine for the motor insurance company whether an applicant is likely or unlikely to involve in a car accident in the next 3 years. As another example, a reference interval can be generated for determining whether an individual is likely or unlikely to buy a newly released mobile application.

Although the present disclosure has made reference to the of health or risk parameter values of living organisms, systems and methods provided herein may be employed for use with various types of non-health or risk-related parameters. Such parameters can be any parameters that describe or are associated with the characteristics or property of the population. Similarly, systems and methods provided herein may be employed for use with any population of non-living organisms. For example, a reference interval can be generated for determining whether there will be an earthquake in a geographical region with information of a number of earthquakes. As another example, a reference interval can be used to determine the safety level of a car seat among a population of car seats.

3D Population Maps

In some aspects, disclosed herein is a computer-implemented method for facilitating analysis of a population. Such a population may be a population of living organisms such as humans, mammals, or any other living organisms. Alternatively, or in combination, such a population may include non-living objects, such as rocks, stars, metals, oils, wood, coals, buildings, metals, and/or minerals. For example, the present methods allow for analysis of various phenomena such as, for example, shipping lanes (e.g., having parameters such as travel distance, type of ship, cargo size, etc.), mining (e.g., having parameters such as type of soil/rock, resource properties, depth of the mining shaft, etc.), and crops (e.g., having parameters such as amount of fertilizer/pesticides used per acre, number of acres, time of planting, frequency of watering, etc.). In some cases, the method for facilitating analysis of the population of objects includes receiving a first plurality of parameter values, a second plurality of parameter values, and a population percentage, wherein the first plurality of parameter values, the second plurality of parameter values, or both are measured in the population. The parameter values can be health or risk parameter values. As a non-limiting example, for a population of stars, the first and second set of parameter values can be two of heat, light, size, age, and color. In some embodiments, the method herein includes mapping, graphically in three dimensions, the first and the second parameter values with the population percentage thereby generating a population percentage map or equivalently, a population map for facilitating analysis of the population. Such methods of generating 3D population maps for analysis of a population is novel and includes significant improvement to the field of data analysis and/or visualization. Such methods of generating 3D population maps facilitate data handling and analysis by enabling visually convenient data presentation, especially for a large of populations. Such method of generating 3D population maps for analysis of a population can advantageously reduce the data analysis time, enable visual identification of characteristics of the population related to two different parameters of the population. In some cases, the method of generating 3D population maps does not utilize machine learning for modeling the first or second parameter. In some cases, the method of generating 3D population maps does not involve statistical modeling of the first or second parameter. For example, conventional approaches typically use a bell curve to characterize a single parameter but turns to statistical models to analyze multiple parameters (e.g., multiple linear regression to model the relationship of various parameters to an output/readout). By contrast, various embodiments of the present method create the 3D population map as a "3D bell curve" that allows rapid visualization and analysis of the parameters without requiring statistical modeling. Thus, the present method provides a simplified analytical process that improves the technical field of population analysis. The first and second parameters can be related such that the visualization of both parameters provides further context to facilitate the analysis of the population and can include, for example, HDL and total cholesterol levels. The method can include analysis of the 3D population map to identify a "footprint". For example, a footprint can map to define what is "normal" within the population (e.g., a certain percentage of the population falling within a range of the first and second parameter values such as HDL and cholesterol).

In some cases, the 3D population map is generated on a computer. The process of generating the 3D population map can include sending instructions to an output device to print or create a physical representation of the 3D population map. In some cases, the physical representation of the 3D population map is a paper printout, a poster, or a 3D printed map or model. In some cases, the 3D population map is presented as a digital or virtual representation such as, for example, an image on a computer screen, a 3D image (e.g., using VR goggles or other VR display), a 2D video, or a 3D video. The process of generating a 3D population map can include providing tools for a user to annotate the map such as, for example, delineating boundaries of a footprint or adding comments. In some cases, the tools allow a user to share the 3D population map over web conference.

In some cases, the 3D population map is used to evaluate a subject. For example, a 3D population map visualizing HDL and cholesterol values in a population can be used to assess a patient and determine a health status of the patient. The health status can be a risk or probability of a certain health outcome (e.g., mortality, disease incidence, etc.). In some cases, the 3D population map is used to sort one or more patients into two or more groups. For example, a patient may fall within or outside the "footprint". The groups can include therapeutic interventions with an assessment that recommends a particular therapeutic intervention or treatment for patients falling within a group and no treatment or an alternative treatment in one or more other groups. This allows a healthcare practitioner to make a treatment decision based on the information from the 3D population map (or a corresponding lookup table comprising the reference intervals). In some cases, the 3D population map comprises one or more areas or volumes that represent one or more groups (e.g., high risk cardiovascular event, low risk cardiovascular event, etc.). A patient may be tracked or monitored over time according to such a 3D population map. In some instances, a personalized 3D population map is used that is specific to one or more demographic or other factor of the patient. For example, a 3D population map can be customized or personalized to a particular gender, age group, ethnicity, location (e.g., latitude/longitude, continent, urban/ suburban/rural, etc.) shared by the patient or subject. This allows for more accurate analysis by helping to control for one or more variables.

In some cases, the data set used to generate the 3D population map has a minimum size. The present disclosure recognizes that the 3D population maps are greatly improved through the acquisition of a sufficiently large data set. The data set can have a minimum number of samples or observations. For example, the data set can include at least 1,000 samples, at least 5,000 samples, at least 10,000 samples, at least 20,000 samples, at least 30,000 samples, at least 40,000 samples, at least 50,000 samples, at least 60,000 samples, at least 70,000 samples, at least 80,000 samples, at least 90,000 samples, at least 100,000 samples, at least 200,000 samples, at least 300,000 samples, at least 400,000 samples, or at least 500,000 samples.

Described herein are systems and methods that generate and/or utilize analysis and evidence-based models or maps of data in order to generate a reference interval. A map comprises one or more individual parameter values that are collected from a population of individuals. The mapped data, in some embodiments, is arranged graphically in three dimensions. In some embodiments, the data points used by the systems and methods described herein are received from a large population study such as, for example, a large cohort follow-up study.

In some cases, the methods and systems described herein are used for diagnosing or treating a disease, disorder, or health condition. The disease, disorder, or health condition can be an infectious disease such as a disease caused by a pathogenic microbial agent (e.g., virus, bacteria, fungi, protozoa, multi-cellular organisms) or prions, or a non-infectious disease such as cancer, cardiovascular disease, or genetic disorder (e.g., phenylketonuria). Examples of cardiovascular disease or symptoms thereof include, but are not limited to, stroke, heart failure, hypertensive heart disease, rheumatic heart disease, cardiomyopathy, abnormal heart rhythms, congenital heart disease, aortic aneurysms, peripheral artery disease, and thrombosis. In some instances, the cancer is in remission. Such diseases, disorders, or conditions can be treated, prevented, inhibited, reduced, or otherwise ameliorated using treatments or therapies known in the art. For example, statins may be administered to individuals who fall outside of the "healthy" reference intervals or ranges based on HDL and LDL cholesterol levels assessed using a multi-dimensional lookup table. In some cases, treatment is provided by prescription from a healthcare practitioner. Examples of various cardiovascular disease treatments include cholesterol lowering drugs (e.g., statins), aspirin, beta blockers, calcium channel blockers, ranolazine, nitroglycerin, and angiotensin-converting enzyme (ACE) inhibitors. Other treatments include surgery such as angioplasty and coronary artery bypass surgery. Cancers can be treated depending on the type of cancer. Cancer treatments can include chemotherapy, radiation, immunotherapy, and/or surgery. In some instances, the cancer is a stage I, stage II, stage III, or stage IV cancer. Examples of cancers include, but are not limited to, breast cancer, ovarian cancer, uterine cancer, cervical cancer, prostate cancer, pancreatic cancer, bladder cancer, leukemia, bone cancer, lung cancer, skin cancer, primary liver cancer, kidney cancer, Kaposi's Sarcoma, viral-induced cancers including hepatitis B virus (HBV), hepatitis C virus (HCV), and hepatocellular carcinoma, human papilloma virus (HPV) and cervical cancer, central nervous system (CNS) cancer, peripheral nervous system (PNS) cancers, oral cavity and oropharyngeal cancer, testicular cancer, thymus cancer, rectal cancer, and colon cancer.

A digital processing device includes one or more hardware central processing units (CPUs) or general purpose graphics processing units (GPGPUs) that carry out the device's functions. The digital processing device further comprises an operating system configured to perform executable instructions. The digital processing device is optionally connected to a computer network. The digital processing device is optionally connected to the Internet such that it accesses the World Wide Web. The digital processing device is optionally connected to a cloud computing infrastructure. Suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein.

Typically, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux". In some embodiments, the operating system is provided by cloud computing.

A digital processing device as described herein either includes or is operatively coupled to a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A system or method as described herein can be used to generate one or more reference intervals which may then be used by a non-health care related professional to determine whether an individual value falls within or outside of a reference interval. In addition, in some embodiments, a system or method as described herein generates a database as containing or comprising one or more reference intervals.

In some embodiments, a database herein provides a relative risk of presence/absence of a status (outcome) associated with one or more parameter values that fall either within or outside of a reference interval.

Some embodiments of the systems described herein are computer based systems. These embodiments include a CPU including a processor and memory which may be in the form of a non-transitory computer readable storage medium. These system embodiments further include software that is typically stored in memory (such as in the form of a non-transitory computer readable storage medium) where the software is configured to cause the processor to carry out a function. Software embodiments incorporated into the systems described herein contain one or more modules.

The software embodiments described herein are configured to cause a processor to: receive population parameter data, generate a graphic map of the population parameter data (preferably in three dimensions), in some embodiments compare the graphic map to a second graphic map, determine a reference interval, and in some embodiments generate a database containing the reference interval.

As shown in FIG. 2, an exemplary method for a non-health care related general application can comprise the following exemplary steps: In a step 201, a device or system receives data from a large population of individuals. A large population suitable for use with the systems and methods described herein comprises, for example, a cohort study such as, for example, a study including 100,000 or more individuals. Data received comprises one or more parameters (as described here). In a step 202, two or more received parameters are mapped preferably in a 3D graphic map. The generated map is configured to represent two or more parameters with respect to each other so that, for example, one or more parameter values are contextualized relative to one or more other parameters. In a step 203, two or more parameters are mapped preferably in a 3D graphic map with respect to their associated outcome level. In a step 204, the first and second 3D maps are compared as by, for example overlaying one graphic map onto another to determine the presence of an overlapping area where both the population distribution is the highest and the outcome (e.g. undesired outcome) is the lowest. In a step 205, a reference interval is determined based on the upper and lower limits of a range in which both the population distribution of two compared parameters is the highest and the outcome for the population is the lowest. In a step 206, a database is generated with the reference interval that was generated.

A digital processing device, in some of the embodiments described herein, includes a display to send visual information to a user. Non-limiting examples of displays suitable for use with the systems and methods described herein include a liquid crystal display (LCD), a thin film transistor liquid crystal display (TFT-LCD), an organic light emitting diode (OLED) display, an OLED display, an active-matrix OLED (AMOLED) display, or a plasma display.

A digital processing device, in some of the embodiments described herein includes an input device to receive information from a user. Non-limiting examples of input devices suitable for use with the systems and methods described herein include a keyboard, a mouse, trackball, track pad, or stylus. In some embodiments, the input device is a touch screen or a multi-touch screen.

The systems and methods described herein typically include one or more non-transitory computer readable storage media encoded with a program including instructions executable by the operating system of an optionally networked digital processing device. In some embodiments of the systems and methods described herein, the non-transitory storage medium is a component of a digital processing device that is a component of a system or is utilized in a method. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Typically the systems and methods described herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages. The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Typically, the systems and methods described herein include and/or utilize one or more databases. In view of the disclosure provided herein, those of skill in the art will recognize that many databases are suitable for storage and retrieval of baseline datasets, files, file systems, objects, systems of objects, as well as data structures and other types of information described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Figure 19:
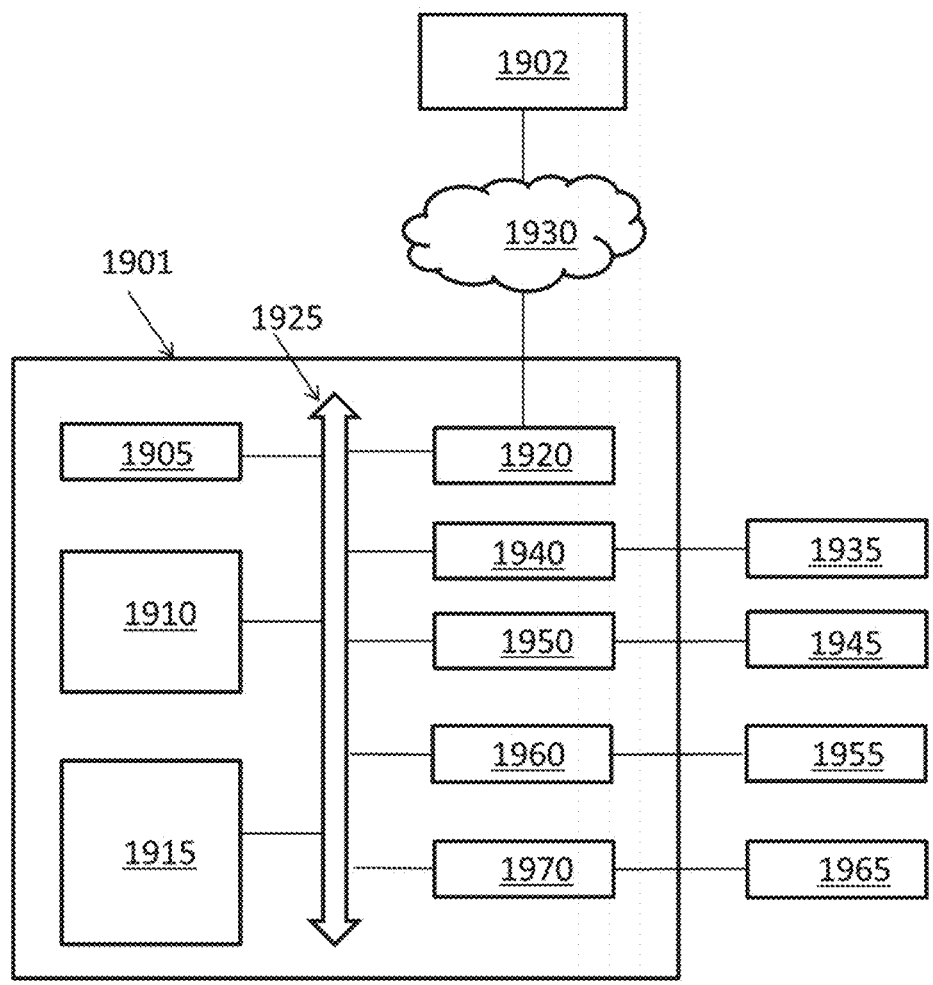
FIG. 19 shows an exemplary embodiment of a digital processing device.

FIG. 19 shows an exemplary embodiment of a system as described herein comprising a digital processing device 1901. The digital processing device 1901 includes a software application configured to analyze a population of individuals to generate reference interval(s) for identifying a healthy or unhealthy status of an individual. The digital processing device 1901 may include a central processing unit (CPU, also "processor" and "computer processor" herein) 1905, which can be a single core or multi-core processor, or a plurality of processors for parallel processing. The digital processing device 1901 also includes either memory or a memory location 1910 (e.g., random-access memory, read-only memory, flash memory), electronic storage unit 1915 (e.g., hard disk), communication interface 1919 (e.g., network adapter, network interface) for communicating with one or more other systems, and peripheral devices, such as cache. The peripheral devices can include storage device(s) or storage medium 1965 which communicate with the rest of the device via a storage interface 1970. The memory 1910, storage unit 1915, interface 1919 and peripheral devices are configured to communicate with the CPU 1905 through a communication bus 1925, such as a motherboard. The digital processing device 1901 can be operatively coupled to a computer network ("network") 1930 with the aid of the communication interface 1919. The network 1930 can comprise the Internet. The network 1930 can be a telecommunication and/or data network.

The digital processing device 1901 includes input device(s) 1945 to receive information from a user, the input device(s) in communication with other elements of the device via an input interface 1950. The digital processing device 1901 can include output device(s) 1955 that communicates to other elements of the device via an output interface 1960.

The CPU 1905 is configured to execute machine-readable instructions embodied in a software application or module. The instructions may be stored in a memory location, such as the memory 1910. The memory 1910 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 110 can also include a basic input/output system (BIOS), including basic routines that help to transfer information between elements within the digital processing device, such as during device start-up, may be stored in the memory 1910.

The storage unit 1915 can be configured to store files, such as health or risk parameter data, e.g., individual health or risk parameter values, health or risk parameter value maps, and value groups. The storage unit 1915 can also be used to store operating system, application programs, and the like. Optionally, storage unit 1915 may be removably interfaced with the digital processing device (e.g., via an external port connector (not shown)) and/or via a storage unit interface. Software may reside, completely or partially, within a computer-readable storage medium within or outside of the storage unit 1915. In another example, software may reside, completely or partially, within processor(s) 1905.

Information and data can be displayed to a user through a display 1935. The display is connected to the bus 1925 via an interface 1940, and transport of data between the display other elements of the device 1901 can be controlled via the interface 1940.

Methods as described herein can be implemented by way of machine (e.g., computer processor) executable code stored on an electronic storage location of the digital processing device 1901, such as, for example, on the memory 1910 or electronic storage unit 1915. The machine executable or machine readable code can be provided in the form of a software application or software module. During use, the code can be executed by the processor 1905. In some cases, the code can be retrieved from the storage unit 1915 and stored on the memory 1910 for ready access by the processor 1905. In some situations, the electronic storage unit 1915 can be precluded, and machine-executable instructions are stored on memory 1910.

A remote device 1902 is configured to communicate with the digital processing device 1901, and may comprises any mobile computing device, non-limiting examples of which include a tablet computer, laptop computer, smartphone, or smartwatch.

Databases

Some embodiments of the systems and methods described herein are configured to generate a database containing or comprising of one or more reference intervals. A database, as described herein, is configured to function as, for example, a lookup table for healthcare providers, other medical industry professionals and/or other end users In these embodiments of the systems and methods described herein, reference intervals are presented in a database so that a user is able to, for example, identify whether a parameter of a specific individual falls within or outside of a reference interval.

Numbered Embodiments

The following embodiments recite nonlimiting permutations of combinations of features disclosed herein. Other permutations of combinations of features are also contemplated. In particular, each of these numbered embodiments is contemplated as depending from or relating to every previous or subsequent numbered embodiment, independent of their order as listed. 1. A computer implemented method for generating a database with reference intervals comprising: (a) receiving a first plurality of health or risk parameter values, a second plurality of health or risk parameter values, a population percentage, and a mortality or adverse outcome rate, wherein the first plurality of health or risk parameter values, the second plurality of health or risk parameter values, or both are measured in a population; (b) mapping, graphically in three dimensions, the first and the second health or risk parameter values with the population percentage thereby generating a population percentage map; (c) mapping, graphically in three dimensions, the first and the second health or risk parameter values with the mortality or adverse outcome rate, thereby generating a mortality or adverse outcome rate map; (d) overlaying the population percentage map onto the mortality or adverse outcome rate map thereby generating an overlap map; (e) generating the reference interval values based on the overlap map; and (f) populating the database with the reference interval values. 2. The computer implemented method of embodiment 1, comprising segregating the first plurality of health or risk parameter values into a first plurality of value groups and segregating the second plurality of health or risk parameter values into a second plurality of value groups. 3. The computer implemented method of embodiment 2, comprising determining an upper value limit and a lower value limit of each of the first plurality of value groups and each of the second plurality of value groups after generation of the overlap map. 4. The computer implemented method of embodiment 3, comprising associating, respectively, each of the first plurality of value groups with each of the second plurality of value groups thereby generating a plurality of associated groups. 5. The computer implemented method of embodiment 1, comprising determining an area of overlapping values in the overlap map where total population percentage is largest and the mortality rate or adverse outcome rate is lowest. 6. The computer implemented method of embodiment 1, wherein the reference interval comprises upper values and lower values of the area of overlapping values in the overlap map where the total population percentage is largest and the mortality or other adverse outcome rate is lowest. 7. The computer implemented method of embodiment 1, wherein the reference interval comprises a lookup table. 8. The computer implemented method of embodiment 1, wherein the first plurality of health or risk parameter values is measured data and the second plurality of health or risk parameter values is demographic data. 9. A system comprising: (a) a computing device comprising a processor; and (b) a non-transitory computer-readable storage media encoded with a computer program including instructions executable by the processor that cause the processor to: (i) receive a first plurality of health or risk parameter values, a second plurality of health or risk parameter values, a population percentage, and a mortality or adverse outcome rate, wherein the first plurality of health or risk parameter values, the second plurality of health or risk parameter values, or both are measured in a population; (ii) map, graphically in three dimensions, the first and the second health or risk parameter values with the population percentage thereby generating a population percentage map; (iii) map, graphically in three dimensions, the first and the second health or risk parameter values with the mortality or adverse outcome rate thereby generating a mortality or adverse outcome rate map; (iv) overlay, the population percentage map onto the mortality or adverse outcome rate map thereby generating an overlap map; (v) generate reference interval values based on the overlap map; and (vi) populating a database with the reference interval values, the reference interval values taking a form of a lookup table. 10. The system of embodiment 9, wherein the computer program causes the processor to segregate the first plurality of health or risk parameter values into a first plurality of value groups and segregating the second plurality of health or risk parameter values into a second plurality of value groups. 11. The system of embodiment 10, wherein upper value limits and lower value limits of each of the first plurality of value groups and each of the second plurality of value groups are determined after generation of the overlap map. 12. The system of embodiment 11, wherein the computer program causes the processor to associate, respectively, each of the first plurality of value groups with each of the second plurality of value groups thereby generating a plurality of associated groups 13. The system of embodiment 9, wherein the computer program causes the processor to determine an area of overlapping values in the overlap map where the total population percentage is largest and the mortality or other adverse outcome rate is lowest. 14. The system of embodiment 9, wherein the reference interval comprises upper values and lower values of the area of overlapping values in the overlap map where the total population percentage is largest and the mortality or other adverse outcome rate is lowest. 15. The system of embodiment 9, wherein the first plurality of health or risk parameter values is measured and the second plurality of health or risk parameter values is demographic data. 16. A computer-implemented system for analyzing a population of individuals comprising a majority of healthy individuals, including their health or risk outcomes, in order to generate one or more reference intervals of joint first and second risk parameters, the one or more reference intervals useful for identifying a healthy or an unhealthy status of an individual based on the first and second risk parameters, the system comprising: (a) a digital processing device comprising a processor, a memory, and an operating system configured to perform executable instructions; and (b) a computer program including instructions executable by the digital processing device to generate the one or more reference intervals, the computer program comprising: (i) a data ingestion module configured to import data, the data comprising long-term health parameter data comprising first risk parameter data, second risk parameter data, and mortality or adverse outcome data from the population of individuals having at least one shared demographic feature, the population comprising a majority of healthy individuals and a minority of unhealthy individuals; (ii) a grouping module configured to group the first risk parameter data into a first plurality of data groups and the second risk parameter data into a second plurality of data groups; (iii) a joining module configured to join the first plurality of data groups with the second plurality of data groups generating a plurality of joint risk parameters; (iv) a comparison module configured to compare the mortality or adverse outcome data with the plurality of joint risk parameters thereby generating joint mortality or adverse outcome data; (v) a distribution module configured to determine a distribution of the plurality of joint risk parameters; (vi) an overlap module configured to determine whether an overlap is present between the distribution of the plurality of joint risk parameters and the joint mortality or adverse outcome data; (vii) an interval generating module configured to generate the one or more reference intervals based on the overlap, wherein when the overlap is present, the distribution of the plurality of joint risk parameters is relatively high and a mortality risk represented by the joint mortality or adverse outcome data is relatively low; and (viii) a table generating module configured to generate a two dimensional lookup table comprising the one or more reference intervals, wherein the lookup table is used by a health care provider or other end user to identify the healthy or the unhealthy status of the individual. 17. The system of embodiment 16, wherein the computer program comprises at least a first application and a second application. 18. The system of embodiment 17, wherein the data ingestion module, the grouping module, the joining module, the comparison module, the distribution module, the overlap module, and the interval generating module are implemented in the first application, the second application, or both the first application and the second application. 19. The system of embodiment 16, wherein the majority of healthy individuals comprises at least 60%, at least 70%, at least 80%, or at least 90% of the population. 20. The system of embodiment 16, wherein the population of individuals has at least 2, 3, 4 or 5 shared demographic features. 21. The system of embodiment 16, wherein the shared demographic features comprise one or more of sex, age, race, or region of residence. 22. The system of embodiment 16, wherein the one or more reference intervals comprises a range of values. 23. The system of embodiment 16, wherein the computer program further comprises a data extraction module configured to extract the health parameter data and mortality or adverse outcome data for the population from the data that is ingested. 24. The system of embodiment 16, wherein the computer program further comprises a risk parameter selection module configured to allow the lookup table creator to select the first risk parameter, the second risk parameter, or both the first risk parameter and the second risk parameter. 25. The system of embodiment 16, wherein the computer program further comprises a demographic selection module configured to allow the lookup table creator to select the shared demographic feature(s). 26. The system of embodiment 16, wherein the computer program further comprises a visualization module configured to generate a 3D visualization of the distribution of the plurality of joint risk parameters and a 3D visualization of the joint mortality or adverse outcome data. 27. Non-transitory computer-readable storage media encoded with a computer program including instructions executable by a processor to analyze a population of individuals comprising a majority of healthy individuals, including their health or risk outcomes, in order to generate one or more reference intervals of joint first and second risk parameters, the one or more reference intervals useful for identifying a healthy or an unhealthy status of an individual based on the first and second risk parameters, the computer program comprising: (a) a data ingestion module configured to import data, the data comprising long-term health parameter data comprising first risk parameter data, second risk parameter data, and mortality or adverse outcome data from the population of individuals having at least one shared demographic feature, the population comprising a majority of healthy individuals and a minority of unhealthy individuals; (b) a grouping module configured to group the first risk parameter data into a first plurality of data groups and the second risk parameter data into a second plurality of data groups; (c) a joining module configured to join the first plurality of data groups with the second plurality of data groups generating a plurality of joint risk parameters; (d) a comparison module configured to compare the mortality or adverse outcome data with the plurality of joint risk parameters thereby generating joint mortality or adverse outcome data; (e) a distribution module configured to determine a distribution of the plurality of joint risk parameters; (f) an overlap module configured to determine whether an overlap is present between the distribution of the plurality of joint risk parameters and the joint mortality or adverse outcome data; (g) an interval generating module configured to generate the one or more reference intervals based on the overlap, wherein when the overlap is present, the distribution of the plurality of joint risk parameters is relatively high and a mortality risk represented by the joint mortality or adverse outcome data is relatively low; and (h) a table generating module configured to generate a two dimensional lookup table comprising the one or more reference intervals, wherein the lookup table is used by a health care provider and/or other end user to identify the healthy or the unhealthy status of the individual. 28. The storage media of embodiment 27, wherein the computer program comprises at least a first application and a second application. 29. The storage media of embodiment 28, wherein the data ingestion module, the grouping module, the joining module, the comparison module, the distribution module, the overlap module, and the interval generating module are implemented in the first application, the second application, or both the first application and the second application. 30. The storage media of embodiment 27, wherein the majority of healthy individuals comprises at least 60%, at least 70%, at least 80%, or at least 90% of the population. 31. The storage media of embodiment 27, wherein the population of individuals has at least 2, 3, 4 or 5 shared demographic features. 32. The storage media of embodiment 27, wherein the shared demographic features comprise one or more of sex, age, race, or region of residence. 33. The storage media of embodiment 27, wherein the one or more reference intervals comprises a range of values. 34. The storage media of embodiment 27, wherein the computer program further comprises a data extraction module configured to extract the health parameter data and mortality or adverse outcome data for the population from the data that is ingested. 35. The storage media of embodiment 27, wherein the computer program further comprises a risk parameter selection module configured to allow the lookup table creator to select the first risk parameter, the second risk parameter, or both the first risk parameter and the second risk parameter. 36. The storage media of embodiment 27, wherein the computer program further comprises a demographic selection module configured to allow the lookup table creator to select the shared demographic feature. 37. The storage media of embodiment 27, wherein the computer program further comprises a visualization module configured to generate a 3D visualization of the distribution of the plurality of joint risk parameters and a 3D visualization of the joint mortality or adverse outcome data. 38. A computer-implemented system for analyzing a population of individuals in order to generate one or more reference intervals of joint first and second risk parameters, the one or more reference intervals useful for identifying a status of an individual based on the first and second risk parameters, the system comprising: (a) a digital processing device comprising a processor, a memory, and an operating system configured to perform executable instructions; and (b) a computer program including instructions executable by the digital processing device to generate the one or more reference intervals, the computer program comprising: (i) a data ingestion module configured to import data, the data comprising long-term parameter data comprising first risk parameter data, second risk parameter data, and outcome data from a population of individuals having at least one shared demographic feature, the population comprising individuals having the status and individuals not having the status; (ii) a grouping module configured to group the first risk parameter data into a first plurality of data groups and the second risk parameter data into a second plurality of data groups; (iii) a joining module configured to join the first plurality of data groups with the second plurality of data groups generating the plurality of joint risk parameters; (iv) a comparison module configured to compare the outcome data with the plurality of joint risk parameters thereby generating joined outcome data; (v) an interval generating module configured to generate the one or more reference intervals; and (vi) a table generating module configured to generate a two dimensional lookup table comprising the one or more reference intervals, wherein the lookup table is used to determine the status of the individual. 39. The system of embodiment 38, wherein the computer program comprises at least a first application and a second application. 40. The system of embodiment 38, wherein the data ingestion module, the grouping module, the joining module, the comparison module, and the interval generating module are implemented in the first application, the second application, or both the first application and the second application. 41. The system of embodiment 38, wherein the individuals not having the status comprise at least 60%, at least 70%, at least 80%, or at least 90% of the population. 42. The system of embodiment 38, wherein the population of individuals has at least 2, 3, 4 or 5 shared demographic features. 43. The system of embodiment 38, wherein the shared demographic features comprise one or more of sex, age, race, or region of residence. 44. The system of embodiment 38, wherein the outcome data comprises one or more of mortality data, adverse outcome data, risk data, or diagnostic data. 45. The system of embodiment 38, wherein the one or more reference intervals comprises a range of values. 46. The system of embodiment 38, wherein the computer program further comprises a data extraction module configured to extract the parameter data and outcome data for the population from the data that is ingested. 47. The system of embodiment 38, wherein the computer program further comprises a risk parameter selection module configured to allow the lookup table creator to select the first risk parameter, the second risk parameter, or both the first risk parameter and the second risk parameter. 48. The system of embodiment 38, wherein the computer program further comprises a demographic selection module configured to allow the lookup table creator to select the shared demographic feature. 49. The system of embodiment 38, wherein the computer program further comprises a distribution module configured to determine a distribution of the plurality of joint risk parameters. 50. The system of embodiment 49, wherein the computer program further comprises a visualization module configured to generate a 3D visualization of the distribution of the plurality of joint risk parameters and a 3D visualization of the joined outcome data. 51. The system of embodiment 50, wherein the computer program further comprises an overlap module configured to determine a region of overlap between the 3D visualization of the distribution of the plurality of joint risk parameters and the 3D visualization of the joined outcome data. 52. The system of embodiment 51, wherein the region of overlap comprises a value or a range of values wherein both the distribution of the plurality of joint risk parameters is relatively high and an outcome risk represented by the joined outcome data is relatively low. 53. The system of embodiment 52, wherein the one or more reference intervals is based on the region of overlap. 54. Non-transitory computer-readable storage media encoded with a computer program including instructions executable by a processor to analyze a population of individuals in order to generate one or more reference intervals of joint first and second risk parameters, the one or more reference intervals useful for identifying a status of an individual based on the first and second risk parameters, the computer program comprising: (a) a data ingestion module configured to import data, the data comprising long-term parameter data comprising first risk parameter data, second risk parameter data, and outcome data from a population of individuals having at least one shared demographic feature, the population comprising individuals having the status and individuals not having the status; (b) a grouping module configured to group the first risk parameter data into a first plurality of data groups and the second risk parameter data into a second plurality of data groups; (c) a joining module configured to join the first plurality of data groups with the second plurality of data groups generating the plurality of joint risk parameters; (d) a comparison module configured to compare the outcome data with the plurality of joint risk parameters thereby generating joined outcome data; and (e) an interval generating module configured to generate the one or more reference intervals; and (f) a table generating module configured to generate a two dimensional lookup table comprising the one or more reference intervals, wherein the lookup table is used to determine the status of the individual. 55. The storage media of embodiment 54, wherein the computer program comprises at least a first application and a second application. 56. The storage media of embodiment 55, wherein the data ingestion module, the grouping module, the joining module, the comparison module, and the interval generating module are implemented in the first application, the second application, or both the first application and the second application. 57. The storage media of embodiment 54, wherein the individuals not having the status comprise at least 60%, at least 70%, at least 80%, or at least 90% of the population. 58. The storage media of embodiment 54, wherein the population of individuals has at least 2, 3, 4 or 5 shared demographic features. 59. The storage media of embodiment 54, wherein the shared demographic features comprise one or more of sex, age, race, or region of residence. 60. The storage media of embodiment 54, wherein the outcome data comprises one or more of mortality data, adverse outcome data, risk data, or diagnostic data. 61. The storage media of embodiment 54, wherein the one or more reference intervals comprises a range of values. 62. The storage media of embodiment 54, wherein the computer program further comprises a data extraction module configured to extract the parameter data and outcome data for the population from the data that is ingested. 63. The storage media of embodiment 54, wherein the computer program further comprises a risk parameter selection module configured to allow the lookup table creator to select the first risk parameter, the second risk parameter, or both the first risk parameter and the second risk parameter. 64. The storage media of embodiment 54, wherein the computer program further comprises a demographic selection module configured to allow the lookup table creator to select the shared demographic feature. 65. The storage media of embodiment 54, wherein the computer program further comprises a distribution module configured to determine a distribution of the plurality of joint risk parameters. 66. The storage media of embodiment 65, wherein the computer program further comprises a visualization module configured to generate a 3D visualization of the distribution of the plurality of joint risk parameters and a 3D visualization of the joined outcome data. 67. The storage media of embodiment 66, wherein the computer program further comprises an overlap module configured to determine a region of overlap between the 3D visualization of the distribution of the plurality of joint risk parameters and the 3D visualization of the joined outcome data. 68. The storage media of embodiment 67, wherein the region of overlap comprises a value or a range of values wherein both the distribution of the plurality of joint risk parameters is relatively high and an outcome risk represented by the joined outcome data is relatively low. 69. The storage media of embodiment 68, wherein the one or more reference intervals is based on the region of overlap. 70. A computer implemented method for generating a database with reference intervals comprising: (a) receiving a first plurality of parameter values, a second plurality of parameter values, a population percentage, and an adverse outcome rate, wherein the first plurality of parameter values, the second plurality of parameter values, or both are measured in a population; (b) mapping, graphically in three dimensions, the first and the second parameter values with the population percentage thereby generating a population percentage map; (c) mapping, graphically in three dimensions, the first and the second parameter values with the adverse outcome rate, thereby generating an adverse outcome rate map; (d) overlaying the population percentage map onto the adverse outcome rate map thereby generating an overlap map; (e) generating the reference interval values based on the overlap map; and (f) populating the database with the reference interval values. 71. The computer implemented method of embodiment 70, comprising segregating the first plurality of parameter values into a first plurality of value groups and segregating the second plurality of parameter values into a second plurality of value groups. 72. The computer implemented method of embodiment 71, comprising determining an upper value limit and a lower value limit of each of the first plurality of value groups and each of the second plurality of value groups after generating the overlap map. 73. The computer implemented method of embodiment 72, comprising associating, respectively, each of the first plurality of value groups with each of the second plurality of value groups thereby generating a plurality of associated groups. 74. The computer implemented method of embodiment 70, comprising determining an area of overlapping values in the overlap map where total population percentage is largest and the adverse outcome rate is lowest. 75. The computer implemented method of embodiment 70, wherein the reference interval comprises upper values and lower values of the area of overlapping values in the overlap map where total population percentage is largest and the adverse outcome rate is lowest. 76. The computer implemented method of embodiment 70, wherein the reference interval comprises a lookup table. 77. The computer implemented method of embodiment 70, wherein the first plurality of parameter values is measured or sensed and the second plurality of parameter values is demographic data. 78. A system comprising: (a) a computing device comprising a processor; and (b) a non-transitory computer-readable storage media encoded with a computer program including instructions executable by the processor that cause the processor to: (i) receive a first plurality of parameter values, a second plurality of parameter values, a population percentage, and an adverse outcome rate, wherein the first plurality of parameter values, the second plurality of parameter values, or both are measured in the population; (ii) map, graphically in three dimensions, the first and the second values with the population percentage thereby generating a population percentage map; (iii) map, graphically in three dimensions, the first and the second parameter values with the adverse outcome rate thereby generating an adverse outcome rate map; (iv) overlay, the population percentage map onto the adverse outcome rate map thereby generating an overlap map; (v) generate reference interval values based on the overlap map; and (vi) populate a database with the reference interval values, the reference interval values taking a form of a lookup table. 79. The system of embodiment 78, wherein the computer program causes the processor to segregate the first plurality of parameter values into a first plurality of value groups and segregating the second plurality of parameter values into a second plurality of value groups. 80. The system of embodiment 79, wherein upper value limits and lower value limits of each of the first plurality of value groups and each of the second plurality of value groups are determined after generation of the overlap map. 81. The system of embodiment 80, wherein the computer program causes the processor to associate, respectively, each of the first plurality of value groups with each of the second plurality of value groups thereby generating a plurality of associated groups. 82. The system of embodiment 81, wherein the computer program causes the processor to determine an area of overlapping values in the overlap map where total population percentage is largest and the mortality or other adverse outcome rate is lowest. 83. The system of embodiment 82, wherein the reference interval comprises upper values and lower values of the area of overlapping values in the overlap map where total population percentage is largest and the mortality or other adverse outcome rate is lowest. 84. The system of embodiment 83, wherein the first plurality of parameter values is measured or sensed and the second plurality of parameter values is demographic data. 85. Non-transitory computer-readable storage media encoded with a computer program including instructions executable by a processor to generate one or more reference intervals useful for identifying a status of an individual based on the first and second risk parameters, the computer program comprising: (i) a software module receiving a first plurality of parameter values, a second plurality of parameter values, a population percentage, and an adverse outcome rate, wherein the first plurality of parameter values, the second plurality of parameter values, or both are measured in the population; (ii) a software module mapping, graphically in three dimensions, the first and the second values with the population percentage thereby generating a population percentage map; (iii) a software module mapping, graphically in three dimensions, the first and the second parameter values with the adverse outcome rate thereby generating an adverse outcome rate map; (iv) a software module overlaying the population percentage map onto the adverse outcome rate map, thereby generating an overlap map; (v) a software module generating reference interval values based on the overlap map; and (vi) a software module populating a database with the reference interval values, the reference interval values taking a form of a lookup table. 86. The media of embodiment 85, wherein the computer program causes the processor to segregate the first plurality of parameter values into a first plurality of value groups and segregating the second plurality of parameter values into a second plurality of value groups. 87. The media of embodiment 86, wherein upper value limits and lower value limits of each of the first plurality of value groups and each of the second plurality of value groups are determined after generation of the overlap map. 88. The media of embodiment 87, wherein the computer program causes the processor to associate, respectively, each of the first plurality of value groups with each of the second plurality of value groups thereby generating a plurality of associated groups. 89. The media of embodiment 88, wherein the computer program causes the processor to determine an area of overlapping values in the overlap map where total population percentage is largest and the mortality or other adverse outcome rate is lowest. 90. The media of embodiment 89, wherein the reference interval comprises upper values and lower values of the area of overlapping values in the overlap map where total population percentage is largest and the mortality or other adverse outcome rate is lowest. 91. The media of embodiment 90, wherein the first plurality of parameter values is measured or sensed and the second plurality of parameter values is demographic data. 92. A computer-implemented method for facilitating analysis of a population, comprising: (a) receiving a first plurality parameter values, a second plurality of parameter values, a population percentage, wherein the first plurality of parameter values, the second plurality of values, or both are measured in the population; and (b) mapping, graphically in three dimensions, the first and the second parameter values with the population percentage thereby generating a population percentage map for facilitating analysis of the population. 93. The computer implemented method of embodiment 92, wherein the first or the second parameter values are non-health care related parameter values. 94. The computer implemented method of embodiment 92, wherein the first or the second parameter values are health care related parameter values. 95. The computer implemented method of embodiment 92, wherein the first plurality of parameter values is measured or sensed and the second plurality of parameter values is demographic data. 96. The computer implemented method of embodiment 92, wherein the population is of non-living or living objects. 97. The computer implemented method of embodiment 92, comprising segregating the first plurality of parameter values into a first plurality of value groups and segregating the second plurality of parameter values into a second plurality of value groups. 98. A computer-implemented system for facilitating analysis of a population, the system comprising: (a) a digital processing device comprising a processor, a memory, and an operating system configured to perform executable instructions; and (b) a computer program including instructions executable by the digital processing device to generate the one or more reference intervals, the computer program comprising: (i) a software module receiving a first plurality parameter values, a second plurality of parameter values, a population percentage, wherein the first plurality of parameter values, the second plurality of values, or both are measured in the population; and (ii) a software module mapping, graphically in three dimensions, the first and the second parameter values with the population percentage thereby generating a population percentage map for facilitating analysis of the population. 99. The system of embodiment 98, wherein the first or the second parameter values are non-health care related parameter values. 100. The system of embodiment 98, wherein the first or the second parameter values are health care related parameter values. 101. The system of embodiment 98, wherein the first plurality of parameter values is measured or sensed and the second plurality of parameter values is demographic data. 102. The system of embodiment 98, wherein the population is of non-living or living objects. 103. The system of embodiment 98, comprising segregating the first plurality of parameter values into a first plurality of value groups and segregating the second plurality of parameter values into a second plurality of value groups. 104. Non-transitory computer-readable storage media encoded with a computer program including instructions executable by a processor to facilitate analysis of a population, the computer program comprising: (a) a software module receiving a first plurality parameter values, a second plurality of parameter values, a population percentage, wherein the first plurality of parameter values, the second plurality of values, or both are measured in the population; and (b) a software module mapping, graphically in three dimensions, the first and the second parameter values with the population percentage thereby generating a population percentage map for facilitating analysis of the population. 105. The system of embodiment 104, wherein the first or the second parameter values are non-health care related parameter values. 106. The system of embodiment 104, wherein the first or the second parameter values are health care related parameter values. 107. The system of embodiment 104, wherein the first plurality of parameter values is measured or sensed and the second plurality of parameter values is demographic data. 108. The system of embodiment 104, wherein the population is of non-living or living objects. 109. The system of embodiment 104, comprising segregating the first plurality of parameter values into a first plurality of value groups and segregating the second plurality of parameter values into a second plurality of value groups.

EXAMPLES

The following illustrative examples are representative of embodiments of the software applications, systems, and methods described herein and are not meant to be limiting in any way.

Example 1. Reference Intervals Generation for Women 20-59 Using TC, HDL and TC/HDL Ratio To generate reference interval(s) using the methods and systems disclosed herein, a population of life insurance applicants tested between 1989 and 2005 and followed to 2010 are divided by sex and age into four different groups, i.e., female 20 to 59 years old (a total number of 2,557,709 subjects), male 20 to 59 years old (a total number of 3,765,817 subjects), female 60 to 89 years old (a total number of 253,310 subjects), and male 60 to 89 years old (a total number of 412,141). Each of the four different groups includes a majority of healthy individuals and a minority of unhealthy individuals. Data from the population comprising long-term health parameter data, such as total cholesterol (TC) level, HDL level, TC/HDL ratio, vital status/mortality data are imported for each subject except missing data from less than 0.001% of the total population of subjects. Each of the health parameters is separated into multiple non-overlapping groups. For example, HDL data is separated into multiple groups in the first column as shown in Table 1 below with the corresponding non-overlapping range shown in the second column of Table 1.

TABLE 1

| HDL (mg/dL) | |
|---|---|
| Label | Value Range |
| 5 | > 0 & < 5 |
| 10 | >= 5 & > 10 |
| 15 | >= 10 & > 15 |
| 20 | >= 15 & < 20 |
| 25 | >= 20 & < 25 |
| 30 | >= 25 & < 30 |
| 35 | >= 30 & < 35 |
| 40 | >= 35 & < 40 |
| 45 | >= 40 & < 45 |
| 50 | >= 45 & < 50 |
| 55 | >= 50 & < 55 |
| 60 | >= 55 & < 60 |
| 65 | >= 60 & < 65 |
| 70 | >= 65 & < 70 |
| 75 | >= 70 & < 75 |
| 80 | >= 75 & < 80 |
| 85 | >= 80 & < 85 |
| 90 | >= 85 & < 90 |
| 95 | >= 90 & < 95 |
| 100 | >= 95 & < 100 |
| 105 | >= 100 & < 105 |
| 110 | >= 105 & < 110 |
| 115 | >= 110 & < 115 |
| 120 | >= 115 & < 120 |
| 120+ | >= 120 |

As another example, TC/HDL ratio data is separated into a different number of groups in the first column as shown in Table 2 below with the corresponding range shown in the second column.

TABLE 2

TC/HDL Ratio

| Label | Value Range |
|---|---|
| .5 | > 0 & < .5 |
| 1.5 | >= 1 & < 1.5 |
| 2 | >= 1.5 & < 2 |
| 2.5 | >= 2 & < 2.5 |
| 3 | >= 2.5 & < 3 |
| 3.5 | >= 3 & < 3.5 |
| 4 | >= 3.5 & < 4 |
| 4.5 | >= 4 & < 4.5 |
| 5 | >= 4.5 & < 5 |
| 5.5 | >= 5 & < 5.5 |
| 6 | >= 5.5 & < 6 |
| 6.5 | >= 6 & < 6.5 |
| 7 | >= 6.5 & < 7 |
| 7.5 | >= 7 & < 7.5 |
| 8 | >= 7.5 & < 8 |
| 8.5 | >= 8 & < 8.5 |
| 9 | >= 8.5 & < 9 |
| 9.5 | >= 9 & < 9.5 |
| 10 | >= 9.5 & < 10 |
| 10+ | >= 10 |

Each group from the data groups for one health parameter, e.g., HDL, is joined with every group from the data groups for another health parameter, e.g., TC level or TC/HDL ratio, thereby generating a plurality of joint health parameters as two dimensional lookup/data tables in Tables 3A-3B (HDL and TC), and 5 (HDL and TC/HDL ratio). For each joint health parameter, the number of individuals for each joint health parameter or in each joined parameter group is counted and percentage of population in each joint group can be obtained. The percentage of population for each of the joint health parameters are shown in Tables 3A-3B. The joint mortality data, e.g., death count, across all values of each of the parameter of the joint parameters are obtained and shown as two dimensional data tables as in Tables 4A-4B (HDL and TC), and 6 (HDL and TC/HDL ratio). The joint death counts can be further processed to derive mortality rates by dividing the number of deaths in each joint parameter group by the total number of individuals in that corresponding group. When the total number of individuals is 0 in a joint parameter group, the mortality rate is not applicable for that particular group. The data in one of the four age/sex groups, i.e. Female, 20-59 years old, can be graphed with the two parameters on x and y axes and the population percentage on z axis as shown in FIGS. 3 and 11. Mortality rate data is graphed with the two parameters on the x and y axis and the mortality rate on the z axis as shown in FIGS. 8 and 16. Overlap between the distribution of the plurality of joint parameters and the joint mortality data is determined by comparing a set of population percentage criteria against a set of mortality rate criteria to determine in which joint parameter groups the highest percentages of population match the lowest mortality rates, this produces a lookup table as shown in FIG. 1. The joint groups with value 1 can be considered as overlaps, thus inside the reference interval. Depending on the customized need for determining the reference interval, groups with value 1 and 2, or 1, 2, and 3 can also be considered as inside the reference interval. The joint groups with value 4 can be considered as non-overlapping and thus outside the reference interval. As an example, the overlap between regions 301 and 1101, and the overlap between regions 801 and 1601 can be visually identified. A reference interval is generated based on the determined overlap, wherein the reference interval(s) are used by a health care provider and/or other end user to identify the healthy or the unhealthy status of the individual, the individual included or outside the population used in the generation of the reference interval using the systems and methods herein.

TABLE 3A

% of population - HDL x TC

| | | \multicolumn{9}{c}{Cholesterol group} |
|---|---|---|---|---|---|---|---|---|---|---|
| | | 10 | 20 | 30 | 40 | 50 | 60 | 70 | 80 | 90 |
| HDL | 5 | | | | | | | | | |
| | 10 | | | | 0.00% | | | | | |
| | 15 | | | | | | | | | 0.00% |
| | 20 | | | | | 0.00% | 0.00% | 0.00% | 0.00% | 0.00% |
| | 25 | | | 0.00% | | | 0.00% | 0.00% | 0.00% | 0.00% |
| | 30 | | | | | | 0.00% | 0.00% | 0.00% | 0.00% |
| | 35 | | | | | | 0.00% | 0.00% | 0.00% | 0.00% |
| | 40 | | | | 0.00% | | 0.00% | 0.00% | 0.00% | 0.00% |
| | 45 | | | | 0.00% | 0.00% | | 0.00% | 0.00% | 0.00% |
| | 50 | 0.00% | | | | 0.00% | 0.00% | 0.00% | 0.00% | 0.00% |
| | 55 | | | | 0.00% | 0.00% | | | 0.00% | 0.00% |
| | 60 | | | | | | 0.00% | 0.00% | 0.00% | 0.00% |
| | 65 | | | | | | | 0.00% | | 0.00% |
| | 70 | 0.00% | | | | | | 0.00% | 0.00% | 0.00% |
| | 75 | | | 0.00% | | | | 0.00% | | |
| | 80 | | | | | | 0.00% | | 0.00% | |
| | 85 | | | | | | | | 0.00% | |
| | 90 | | | | | | | | | |
| | 95 | | | | | | | | | |
| | 100 | | | | | | | | | |
| | 105 | | | | | | | | | |
| | 110 | | | | | | | | | |
| | 115 | | | | | | | | | |
| | 120 | | | | | | | | | |
| | 120+ | | | | | | | | | |
| Total | | .0 | .0 | .0 | .0 | .0 | .0 | .0 | .0 | |

TABLE 3A-continued

|  |  | Cholesterol group | | | | | | | | |
|---|---|---|---|---|---|---|---|---|---|---|
|  |  | 100 | 110 | 120 | 130 | 140 | 150 | 160 | 170 | 180 |
| HDL | 5 |  |  |  |  | 0.00% |  | 0.00% | 0.00% | 0.00% |
|  | 10 |  |  | 0.00% |  |  |  | 0.00% | 0.00% | 0.00% |
|  | 15 | 0.00% | 0.00% | 0.00% | 0.00% | 0.00% | 0.00% | 0.00% | 0.00% | 0.00% |
|  | 20 | 0.00% | 0.00% | 0.00% | 0.00% | 0.00% | 0.00% | 0.00% | 0.00% | 0.00% |
|  | 25 | 0.00% | 0.00% | 0.00% | 0.01% | 0.01% | 0.01% | 0.01% | 0.01% | 0.01% |
|  | 30 | 0.00% | 0.01% | 0.01% | 0.02% | 0.03% | 0.04% | 0.05% | 0.05% | 0.05% |
|  | 35 | 0.01% | 0.02% | 0.04% | 0.07% | 0.10% | 0.14% | 0.17% | 0.20% | 0.21% |
|  | 40 | 0.01% | 0.03% | 0.08% | 0.15% | 0.24% | 0.33% | 0.41% | 0.46% | 0.49% |
|  | 45 | 0.01% | 0.04% | 0.10% | 0.23% | 0.40% | 0.59% | 0.76% | 0.87% | 0.90% |
|  | 50 | 0.01% | 0.03% | 0.09% | 0.26% | 0.50% | 0.78% | 1.05% | 1.25% | 1.33% |
|  | 55 | 0.00% | 0.02% | 0.07% | 0.22% | 0.47% | 0.81% | 1.18% | 1.45% | 1.58% |
|  | 60 | 0.00% | 0.01% | 0.04% | 0.15% | 0.35% | 0.70% | 1.09% | 1.42% | 1.59% |
|  | 65 | 0.00% | 0.01% | 0.02% | 0.08% | 0.22% | 0.50% | 0.83% | 1.18% | 1.38% |
|  | 70 | 0.00% | 0.00% | 0.01% | 0.04% | 0.12% | 0.29% | 0.56% | 0.84% | 1.07% |
|  | 75 | 0.00% | 0.00% | 0.00% | 0.02% | 0.06% | 0.15% | 0.32% | 0.53% | 0.74% |
|  | 80 | 0.00% | 0.00% | 0.00% | 0.01% | 0.03% | 0.07% | 0.17% | 0.32% | 0.46% |
|  | 85 | 0.00% | 0.00% | 0.00% | 0.00% | 0.01% | 0.03% | 0.09% | 0.17% | 0.27% |
|  | 90 |  | 0.00% | 0.00% | 0.00% | 0.01% | 0.02% | 0.04% | 0.09% | 0.15% |
|  | 95 |  | 0.00% | 0.00% | 0.00% | 0.00% | 0.01% | 0.02% | 0.04% | 0.08% |
|  | 100 |  |  | 0.00% | 0.00% | 0.00% | 0.00% | 0.01% | 0.02% | 0.04% |
|  | 105 |  |  |  | 0.00% | 0.00% | 0.00% | 0.00% | 0.01% | 0.02% |
|  | 110 |  |  | 0.00% | 0.00% | 0.00% | 0.00% | 0.00% | 0.00% | 0.01% |
|  | 115 |  |  | 0.00% | 0.00% | 0.00% | 0.00% | 0.00% | 0.00% | 0.00% |
|  | 120 |  |  |  |  | 0.00% | 0.00% | 0.00% | 0.00% | 0.00% |
|  | 120+ |  |  |  | 0.00% |  | 0.00% | 0.00% | 0.00% | 0.00% |
| Total |  | .0 | .0 | .0 | .0 | .0 | .0 | .1 | .1 | .1 |

TABLE 3B

| % of population-HDL x TC | | | | | | | | | | | |
|---|---|---|---|---|---|---|---|---|---|---|---|
|  |  | Cholesterol group | | | | | | | | | |
|  |  | 190 | 200 | 210 | 220 | 230 | 240 | 250 | 260 | 270 | 280 |
| HDL | 5 |  |  |  |  |  |  |  |  |  |  |
|  | 10 | 0.00% |  | 0.00% | 0.00% | 0.00% | 0.00% |  |  | 0.00% |  |
|  | 15 | 0.00% | 0.00% | 0.00% | 0.00% | 0.00% | 0.00% | 0.00% |  | 0.00% | 0.00% |
|  | 20 | 0.00% | 0.00% | 0.00% | 0.00% | 0.00% | 0.00% | 0.00% | 0.00% | 0.00% | 0.00% |
|  | 25 | 0.01% | 0.01% | 0.01% | 0.01% | 0.01% | 0.00% | 0.00% | 0.00% | 0.00% | 0.00% |
|  | 30 | 0.06% | 0.05% | 0.05% | 0.04% | 0.03% | 0.03% | 0.02% | 0.01% | 0.01% | 0.01% |
|  | 35 | 0.20% | 0.19% | 0.17% | 0.15% | 0.12% | 0.09% | 0.07% | 0.05% | 0.04% | 0.02% |
|  | 40 | 0.48% | 0.46% | 0.40% | 0.33% | 0.26% | 0.21% | 0.16% | 0.11% | 0.08% | 0.05% |
|  | 45 | 0.89% | 0.82% | 0.71% | 0.58% | 0.48% | 0.36% | 0.27% | 0.19% | 0.13% | 0.09% |
|  | 50 | 1.28% | 1.18% | 1.02% | 0.84% | 0.67% | 0.51% | 0.38% | 0.27% | 0.19% | 0.13% |
|  | 55 | 1.54% | 1.45% | 1.24% | 1.02% | 0.81% | 0.62% | 0.45% | 0.33% | 0.22% | 0.15% |
|  | 60 | 1.61% | 1.50% | 1.30% | 1.08% | 0.85% | 0.65% | 0.48% | 0.34% | 0.24% | 0.17% |
|  | 65 | 1.45% | 1.39% | 1.23% | 1.02% | 0.81% | 0.63% | 0.46% | 0.33% | 0.23% | 0.15% |
|  | 70 | 1.17% | 1.15% | 1.04% | 0.88% | 0.71% | 0.55% | 0.39% | 0.29% | 0.20% | 0.14% |
|  | 75 | 0.85% | 0.89% | 0.82% | 0.71% | 0.57% | 0.44% | 0.34% | 0.24% | 0.18% | 0.12% |
|  | 80 | 0.57% | 0.63% | 0.59% | 0.54% | 0.45% | 0.36% | 0.27% | 0.19% | 0.14% | 0.10% |
|  | 85 | 0.36% | 0.41% | 0.42% | 0.39% | 0.33% | 0.27% | 0.20% | 0.15% | 0.12% | 0.08% |
|  | 90 | 0.21% | 0.26% | 0.27% | 0.26% | 0.23% | 0.19% | 0.19% | 0.11% | 0.08% | 0.06% |
|  | 95 | 0.12% | 0.15% | 0.17% | 0.18% | 0.15% | 0.14% | 0.14% | 0.08% | 0.06% | 0.05% |
|  | 100 | 0.07% | 0.09% | 0.11% | 0.11% | 0.11% | 0.09% | 0.09% | 0.06% | 0.05% | 0.03% |
|  | 105 | 0.03% | 0.04% | 0.05% | 0.06% | 0.06% | 0.05% | 0.05% | 0.03% | 0.03% | 0.02% |
|  | 110 | 0.01% | 0.02% | 0.03% | 0.04% | 0.03% | 0.03% | 0.03% | 0.02% | 0.02% | 0.01% |
|  | 115 | 0.01% | 0.01% | 0.02% | 0.02% | 0.02% | 0.02% | 0.02% | 0.02% | 0.01% | 0.01% |
|  | 120 | 0.00% | 0.01% | 0.01% | 0.01% | 0.02% | 0.02% | 0.02% | 0.01% | 0.01% | 0.01% |
|  | 120+ | 0.00% | 0.00% | 0.01% | 0.01% | 0.01% | 0.01% | 0.01% | 0.01% | 0.01% | 0.01% |
| Total |  | .1 | .1 | .1 | .1 | .1 | .1 | .0 | .0 | .0 | .0 |

| % of population-HDL x TC | | | | | | | | | | |
|---|---|---|---|---|---|---|---|---|---|---|
|  |  | Cholesterol group | | | | | | | | |
|  |  | 290 | 300 | 310 | 320 | 330 | 340 | 350 | 350+ | Total |
| HDL | 5 |  |  |  |  |  |  |  |  | .0 |
|  | 10 |  | 0.00% | 0.00% |  |  |  |  |  | .0 |
|  | 15 |  |  |  | 0.00% |  |  |  | 0.00% | .0 |
|  | 20 | 0.00% | 0.00% | 0.00% | 0.00% | 0.00% | 0.00% | 0.00% | 0.00% | .0 |

TABLE 3B-continued

| | | | | | | | | | |
|---|---|---|---|---|---|---|---|---|---|
| 25 | 0.00% | 0.00% | 0.00% | 0.00% | 0.00% | 0.00% | 0.00% | 0.00% | .0 |
| 30 | 0.01% | 0.00% | 0.00% | 0.00% | 0.00% | 0.00% | 0.00% | 0.00% | .0 |
| 35 | 0.02% | 0.01% | 0.01% | 0.00% | 0.00% | 0.00% | 0.00% | 0.01% | .0 |
| 40 | 0.04% | 0.03% | 0.01% | 0.01% | 0.01% | 0.00% | 0.00% | 0.01% | .1 |
| 45 | 0.06% | 0.05% | 0.02% | 0.02% | 0.01% | 0.01% | 0.01% | 0.01% | .1 |
| 50 | 0.09% | 0.06% | 0.03% | 0.03% | 0.02% | 0.01% | 0.01% | 0.02% | .1 |
| 55 | 0.10% | 0.08% | 0.04% | 0.03% | 0.02% | 0.02% | 0.01% | 0.02% | .1 |
| 60 | 0.11% | 0.08% | 0.04% | 0.03% | 0.02% | 0.02% | 0.01% | 0.02% | .1 |
| 65 | 0.11% | 0.08% | 0.04% | 0.03% | 0.02% | 0.01% | 0.01% | 0.02% | .1 |
| 70 | 0.09% | 0.07% | 0.03% | 0.03% | 0.02% | 0.01% | 0.01% | 0.02% | .1 |
| 75 | 0.08% | 0.06% | 0.03% | 0.03% | 0.02% | 0.01% | 0.01% | 0.02% | .1 |
| 80 | 0.07% | 0.05% | 0.02% | 0.02% | 0.01% | 0.01% | 0.01% | 0.02% | .1 |
| 85 | 0.05% | 0.04% | 0.02% | 0.02% | 0.01% | 0.01% | 0.01% | 0.01% | .0 |
| 90 | 0.04% | 0.03% | 0.01% | 0.01% | 0.01% | 0.00% | 0.00% | 0.01% | .0 |
| 95 | 0.03% | 0.02% | 0.01% | 0.01% | 0.01% | 0.00% | 0.00% | 0.01% | .0 |
| 100 | 0.02% | 0.01% | 0.01% | 0.01% | 0.01% | 0.00% | 0.00% | 0.01% | .0 |
| 105 | 0.01% | 0.01% | 0.01% | 0.00% | 0.00% | 0.00% | 0.00% | 0.00% | .0 |
| 110 | 0.01% | 0.01% | 0.00% | 0.00% | 0.00% | 0.00% | 0.00% | 0.00% | .0 |
| 115 | 0.01% | 0.01% | 0.00% | 0.00% | 0.00% | 0.00% | 0.00% | 0.00% | .0 |
| 120 | 0.01% | 0.00% | 0.00% | 0.00% | 0.00% | 0.00% | 0.00% | 0.00% | .0 |
| 120+ | 0.01% | 0.00% | 0.00% | 0.00% | 0.00% | 0.00% | 0.00% | 0.00% | .0 |
| Total | .0 | .0 | .0 | .0 | .0 | .0 | .0 | .0 | 1.0 |

TABLE 4A

Number of deaths-HDL x TC

| | | Cholesterol group | | | | | | | | | | | | | | | | |
|---|---|---|---|---|---|---|---|---|---|---|---|---|---|---|---|---|---|---|
| | | 10 | 20 | 30 | 40 | 50 | 60 | 70 | 80 | 90 | 100 | 110 | 120 | 130 | 140 | 150 | 160 | 170 | 180 |
| HDL group | 5 | 0 | 0 | 0 | 0 | 0 | 0 | 0 | 0 | 0 | 0 | 0 | 0 | 0 | 0 | 0 | 0 | 0 | 0 |
| | 10 | 0 | 0 | 0 | 0 | 0 | 0 | 0 | 0 | 0 | 0 | 0 | 0 | 0 | 0 | 0 | 0 | 0 | 0 |
| | 15 | 0 | 0 | 0 | 0 | 0 | 0 | 0 | 0 | 1 | 0 | 0 | 0 | 0 | 0 | 1 | 0 | 0 | 0 |
| | 20 | 0 | 0 | 0 | 0 | 0 | 1 | 0 | 0 | 1 | 1 | 0 | 2 | 3 | 1 | 1 | 1 | 3 | 3 |
| | 25 | 0 | 0 | 0 | 0 | 0 | 0 | 0 | 1 | 0 | 2 | 3 | 4 | 4 | 3 | 4 | 5 | 13 | 7 |
| | 30 | 0 | 0 | 0 | 0 | 0 | 0 | 0 | 2 | 1 | 3 | 6 | 9 | 14 | 17 | 20 | 18 | 27 | 36 |
| | 35 | 0 | 0 | 0 | 0 | 0 | 1 | 0 | 0 | 4 | 5 | 7 | 18 | 24 | 37 | 41 | 50 | 68 | 76 |
| | 40 | 0 | 0 | 0 | 0 | 0 | 0 | 0 | 1 | 2 | 4 | 8 | 15 | 31 | 57 | 68 | 86 | 132 | 123 |
| | 45 | 0 | 0 | 0 | 0 | 0 | 0 | 0 | 0 | 1 | 4 | 10 | 15 | 41 | 65 | 116 | 156 | 189 | 234 |
| | 50 | 0 | 0 | 0 | 0 | 0 | 0 | 0 | 0 | 2 | 4 | 11 | 16 | 34 | 76 | 117 | 176 | 235 | 272 |
| | 55 | 0 | 0 | 0 | 0 | 0 | 0 | 0 | 0 | 0 | 0 | 7 | 12 | 21 | 68 | 107 | 194 | 241 | 279 |
| | 60 | 0 | 0 | 0 | 0 | 0 | 0 | 0 | 0 | 1 | 4 | 7 | 23 | 47 | 95 | 164 | 213 | 278 | |
| | 65 | 0 | 0 | 0 | 0 | 0 | 0 | 0 | 0 | 0 | 2 | 2 | 5 | 40 | 68 | 120 | 162 | 247 | |
| | 70 | 0 | 0 | 0 | 0 | 0 | 0 | 0 | 0 | 0 | 0 | 1 | 5 | 15 | 48 | 67 | 129 | 162 | |
| | 75 | 0 | 0 | 0 | 0 | 0 | 0 | 0 | 0 | 0 | 0 | 1 | 2 | 6 | 14 | 19 | 53 | 78 | 121 |
| | 80 | 0 | 0 | 0 | 0 | 0 | 0 | 0 | 0 | 0 | 0 | 0 | 1 | 5 | 4 | 15 | 33 | 74 | 71 |
| | 85 | 0 | 0 | 0 | 0 | 0 | 0 | 0 | 0 | 0 | 0 | 0 | 0 | 0 | 3 | 7 | 12 | 32 | 43 |
| | 90 | 0 | 0 | 0 | 0 | 0 | 0 | 0 | 0 | 0 | 0 | 0 | 0 | 0 | 0 | 1 | 10 | 19 | 28 |
| | 95 | 0 | 0 | 0 | 0 | 0 | 0 | 0 | 0 | 0 | 0 | 0 | 1 | 2 | 4 | 8 | 11 | 19 | |
| | 100 | 0 | 0 | 0 | 0 | 0 | 0 | 0 | 0 | 0 | 0 | 0 | 0 | 0 | 2 | 3 | 2 | 12 | |
| | 105 | 0 | 0 | 0 | 0 | 0 | 0 | 0 | 0 | 0 | 0 | 0 | 0 | 1 | 0 | 0 | 0 | 1 | 5 |
| | 110 | 0 | 0 | 0 | 0 | 0 | 0 | 0 | 0 | 0 | 0 | 0 | 0 | 0 | 0 | 0 | 0 | 1 | 0 |
| | 115 | 0 | 0 | 0 | 0 | 0 | 0 | 0 | 0 | 0 | 0 | 0 | 0 | 0 | 1 | 0 | 0 | 1 | 0 |
| | 120 | 0 | 0 | 0 | 0 | 0 | 0 | 0 | 0 | 0 | 0 | 0 | 0 | 0 | 0 | 0 | 0 | 0 | 1 |
| | 120+ | 0 | 0 | 0 | 0 | 0 | 0 | 0 | 0 | 0 | 0 | 0 | 0 | 0 | 0 | 0 | 0 | 1 | 0 |
| Total | | 0 | 0 | 0 | 0 | 0 | 2 | 0 | 4 | 12 | 25 | 59 | 104 | 218 | 450 | 733 | 1157 | 1632 | 2019 |

TABLE 4B

Number of deaths-HDL x TC

| | | Cholesterol group | | | | | | | | | | | | | | | | | | |
|---|---|---|---|---|---|---|---|---|---|---|---|---|---|---|---|---|---|---|---|---|
| | | 190 | 200 | 210 | 220 | 230 | 240 | 250 | 260 | 270 | 280 | 290 | 300 | 310 | 320 | 330 | 340 | 350 | 350+ | Total |
| HDL group | 5 | 0 | 0 | 0 | 0 | 0 | 0 | 0 | 0 | 0 | 0 | 0 | 0 | 0 | 0 | 0 | 0 | 0 | 0 | 0 |
| | 10 | 0 | 0 | 0 | 0 | 0 | 0 | 0 | 0 | 0 | 0 | 0 | 0 | 0 | 0 | 0 | 0 | 0 | 0 | 0 |
| | 15 | 0 | 0 | 0 | 0 | 0 | 0 | 0 | 0 | 0 | 0 | 0 | 0 | 0 | 0 | 0 | 0 | 0 | 0 | 2 |
| | 20 | 0 | 2 | 2 | 3 | 5 | 2 | 3 | 0 | 2 | 0 | 1 | 0 | 0 | 1 | 0 | 1 | 1 | 2 | 42 |
| | 25 | 13 | 3 | 9 | 6 | 4 | 7 | 6 | 3 | 2 | 2 | 0 | 3 | 4 | 0 | 0 | 2 | 0 | 3 | 112 |
| | 30 | 48 | 47 | 42 | 28 | 20 | 27 | 28 | 24 | 16 | 7 | 6 | 6 | 2 | 4 | 4 | 3 | 1 | 9 | 473 |
| | 35 | 95 | 85 | 86 | 83 | 81 | 76 | 63 | 36 | 25 | 18 | 16 | 7 | 18 | 4 | 3 | 4 | 3 | 17 | 1037 |
| | 40 | 180 | 165 | 162 | 131 | 140 | 119 | 91 | 77 | 74 | 39 | 30 | 25 | 18 | 9 | 12 | 11 | 4 | 15 | 1819 |
| | 45 | 226 | 249 | 238 | 227 | 216 | 165 | 180 | 102 | 72 | 66 | 42 | 36 | 28 | 17 | 22 | 22 | 11 | 28 | 2740 |
| | 50 | 327 | 290 | 314 | 233 | 233 | 175 | 160 | 145 | 104 | 62 | 56 | 39 | 39 | 18 | 19 | 13 | 10 | 23 | 3205 |
| | 55 | 295 | 346 | 322 | 276 | 232 | 208 | 186 | 148 | 101 | 67 | 62 | 42 | 26 | 20 | 17 | 14 | 8 | 23 | 3294 |
| | 60 | 295 | 324 | 264 | 279 | 242 | 205 | 145 | 161 | 96 | 82 | 61 | 40 | 31 | 14 | 5 | 5 | 10 | 15 | 3103 |
| | 65 | 238 | 261 | 264 | 254 | 221 | 190 | 148 | 121 | 81 | 62 | 48 | 37 | 28 | 14 | 12 | 7 | 7 | 18 | 2653 |
| | 70 | 182 | 202 | 211 | 179 | 178 | 164 | 120 | 98 | 74 | 60 | 37 | 22 | 23 | 18 | 10 | 8 | 4 | 7 | 2001 |
| | 75 | 138 | 171 | 162 | 167 | 128 | 115 | 107 | 67 | 48 | 43 | 29 | 20 | 12 | 7 | 3 | 8 | 3 | 10 | 1622 |
| | 80 | 111 | 110 | 106 | 117 | 94 | 97 | 85 | 89 | 61 | 39 | 23 | 15 | 9 | 9 | 8 | 4 | 4 | 11 | 1165 |
| | 85 | 65 | 82 | 77 | 101 | 83 | 72 | 62 | 63 | 34 | 30 | 14 | 11 | 11 | 5 | 5 | 3 | 1 | 7 | 813 |
| | 90 | 49 | 89 | 58 | 63 | 81 | 58 | 37 | 31 | 32 | 16 | 18 | 5 | 8 | 3 | 7 | 2 | 4 | 8 | 591 |
| | 95 | 19 | 31 | 45 | 61 | 44 | 45 | 27 | 29 | 19 | 13 | 11 | 10 | 5 | 5 | 1 | 3 | 1 | 5 | 409 |
| | 100 | 12 | 21 | 28 | 38 | 23 | 33 | 23 | 18 | 16 | 14 | 8 | 5 | 7 | 2 | 3 | 3 | 0 | 3 | 273 |
| | 105 | 7 | 13 | 13 | 20 | 15 | 20 | 13 | 15 | 10 | 3 | 8 | 1 | 1 | 1 | 1 | 1 | 1 | 3 | 163 |
| | 110 | 1 | 6 | 4 | 11 | 8 | 13 | 6 | 2 | 1 | 4 | 4 | 3 | 1 | 2 | 0 | 1 | 0 | 0 | 68 |
| | 115 | 0 | 4 | 4 | 5 | 3 | 6 | 10 | 4 | 3 | 2 | 5 | 0 | 1 | 0 | 1 | 1 | 1 | 3 | 65 |
| | 120 | 1 | 1 | 4 | 4 | 4 | 6 | 6 | 3 | 3 | 1 | 1 | 0 | 2 | 0 | 0 | 1 | 0 | 2 | 40 |
| | 120+ | 2 | 4 | 2 | 6 | 7 | 10 | 3 | 9 | 8 | 8 | 8 | 9 | 8 | 3 | 2 | 1 | 1 | 2 | 85 |
| Total | | 2305 | 2475 | 2404 | 2265 | 2062 | 1793 | 1458 | 1213 | 865 | 826 | 474 | 340 | 265 | 154 | 136 | 115 | 72 | 213 | 26860 |

TABLE 5

% of population-HDL x TC/HDL ratio

| | | TC/HDL ratio group | | | | | | | | | | |
|---|---|---|---|---|---|---|---|---|---|---|---|---|
| | | .5 | 1 | 1.5 | 2 | 2.5 | 3 | 3.5 | 4 | 4.5 | 5 | 5.5 |
| HDL group | 5 | | | | | | | | | | | |
| | 10 | | | | | | | | 0.00% | | | |
| | 15 | | | | | | | | | | | |
| | 20 | | | | | | 0.00% | 0.00% | 0.00% | 0.00% | 0.00% | 0.00% |
| | 25 | | | 0.00% | | 0.00% | 0.00% | 0.00% | 0.00% | 0.00% | 0.00% | 0.00% |
| | 30 | | | | | 0.00% | 0.00% | 0.00% | 0.01% | 0.02% | 0.03% | 0.05% |
| | 35 | | | | 0.00% | 0.00% | 0.01% | 0.04% | 0.10% | 0.19% | 0.27% | 0.33% |
| | 40 | | 0.00% | | 0.00% | 0.01% | 0.05% | 0.24% | 0.53% | 0.81% | 0.88% | 0.83% |
| | 45 | | 0.00% | 0.00% | 0.00% | 0.03% | 0.26% | 0.94% | 1.64% | 1.89% | 1.57% | 1.09% |
| | 50 | 0.00% | 0.00% | 0.00% | 0.01% | 0.11% | 0.87% | 2.38% | 3.01% | 2.58% | 1.61% | 0.85% |
| | 55 | | 0.00% | 0.00% | 0.01% | 0.32% | 1.97% | 3.88% | 3.61% | 2.33% | 1.12% | 0.46% |
| | 60 | | 0.00% | 0.00% | 0.03% | 0.69% | 3.20% | 4.49% | 3.10% | 1.53% | 0.57% | 0.19% |
| | 65 | | 0.00% | 0.00% | 0.05% | 1.16% | 3.86% | 3.94% | 2.09% | 0.80% | 0.25% | 0.07% |
| | 70 | 0.00% | 0.00% | 0.00% | 0.09% | 1.55% | 3.70% | 2.81% | 1.13% | 0.35% | 0.09% | 0.03% |
| | 75 | 0.00% | 0.00% | 0.00% | 0.13% | 1.69% | 2.98% | 1.69% | 2.98% | 1.69% | 0.56% | 0.14% |
| | 80 | | 0.00% | 0.00% | 0.16% | 1.62% | 2.07% | 0.93% | 0.25% | 0.05% | 0.01% | 0.00% |
| | 85 | | 0.00% | 0.00% | 0.19% | 1.36% | 1.32% | 0.47% | 0.11% | 0.02% | 0.00% | 0.00% |
| | 90 | | | 0.00% | 0.20% | 1.04% | 0.75% | 0.22% | 0.04% | 0.01% | 0.00% | 0.00% |
| | 95 | | | 0.00% | 0.19% | 0.73% | 0.42% | 0.10% | 0.02% | 0.00% | 0.00% | 0.00% |
| | 100 | | | 0.00% | 0.17% | 0.50% | 0.21% | 0.04% | 0.01% | 0.00% | 0.00% | 0.00% |
| | 105 | | | 0.00% | 0.12% | 0.26% | 0.09% | 0.01% | 0.00% | 0.00% | 0.00% | 0.00% |
| | 110 | | | 0.00% | 0.09% | 0.15% | 0.04% | 0.01% | 0.00% | 0.00% | | |
| | 115 | | | 0.00% | 0.07% | 0.09% | 0.02% | 0.00% | 0.00% | 0.00% | | 0.00% |
| | 120 | | | 0.00% | 0.06% | 0.06% | 0.01% | 0.00% | 0.00% | 0.00% | 0.00% | |
| | 120+ | | 0.00% | 0.00% | 0.06% | 0.04% | 0.01% | 0.00% | 0.00% | | | |
| Total | | .0 | .0 | .0 | .0 | .1 | .2 | .2 | .2 | .1 | .1 | .0 |

TABLE 5-continued

| % of population-HDL x TC/HDL ratio | | | | | | | | | | | |
|---|---|---|---|---|---|---|---|---|---|---|---|
| | TC/HDL ratio group | | | | | | | | | | |
| | 6 | 6.5 | 7 | 7.5 | 8 | 8.5 | 9 | 9.5 | 10 | 10+ | Total |
| HDL group 5 | | | | | | | | | | 0.00% | .0 |
| 10 | | | | | | | | | | 0.00% | .0 |
| 15 | | | | 0.00% | | | 0.00% | 0.00% | 0.00% | 0.00% | .0 |
| 20 | 0.00% | 0.00% | 0.00% | 0.00% | 0.00% | 0.00% | 0.00% | 0.00% | 0.00% | 0.00% | .0 |
| 25 | 0.01% | 0.01% | 0.01% | 0.01% | 0.01% | 0.01% | 0.01% | 0.01% | 0.01% | 0.03% | .0 |
| 30 | 0.06% | 0.07% | 0.08% | 0.07% | 0.06% | 0.05% | 0.03% | 0.02% | 0.01% | 0.03% | .0 |
| 35 | 0.33% | 0.28% | 0.22% | 0.15% | 0.09% | 0.06% | 0.03% | 0.02% | 0.01% | 0.01% | .0 |
| 40 | 0.61% | 0.41% | 0.24% | 0.13% | 0.06% | 0.03% | 0.01% | 0.01% | 0.00% | 0.01% | .0 |
| 45 | 0.62% | 0.31% | 0.14% | 0.06% | 0.03% | 0.01% | 0.01% | 0.00% | 0.00% | 0.00% | .1 |
| 50 | 0.37% | 0.16% | 0.06% | 0.03% | 0.01% | 0.00% | 0.00% | 0.00% | 0.00% | 0.00% | .1 |
| 55 | 0.16% | 0.06% | 0.02% | 0.01% | 0.00% | 0.00% | 0.00% | 0.00% | 0.00% | 0.00% | .1 |
| 60 | 0.06% | 0.02% | 0.01% | 0.00% | 0.00% | 0.00% | 0.00% | 0.00% | | 0.00% | .1 |
| 65 | 0.02% | 0.01% | 0.00% | 0.00% | 0.00% | 0.00% | 0.00% | | | 0.00% | .1 |
| 70 | 0.01% | 0.00% | 0.00% | 0.00% | 0.00% | 0.00% | 0.00% | 0.00% | | | .1 |
| 75 | 0.03% | 0.01% | 0.00% | 0.00% | 0.00% | | | | | 0.00% | .1 |
| 80 | 0.00% | 0.00% | 0.00% | 0.00% | | | | | 0.00% | | .1 |
| 85 | 0.00% | 0.00% | | | 0.00% | | | | | | .0 |
| 90 | 0.00% | 0.00% | | | | | | | | | .0 |
| 95 | 0.00% | | | | | | | | | | .0 |
| 100 | | | | | | | | | | | .0 |
| 105 | 0.00% | | 0.00% | | | | | | | | .0 |
| 110 | | | | | | | | | | | .0 |
| 115 | | | | | | | | | | | .0 |
| 120 | | | | | | | | | | | .0 |
| 120+ | | | | | | | | | | | .0 |
| Total | .0 | .0 | .0 | .0 | .0 | .0 | .0 | .0 | .0 | .0 | 1.0 |

TABLE 6

| Number of deaths-HDL x TC/HDL ratio | | | | | | | | | | | |
|---|---|---|---|---|---|---|---|---|---|---|---|
| | TC/HDL ratio group | | | | | | | | | | |
| | .5 | 1 | 1.5 | 2 | 2.5 | 3 | 3.5 | 4 | 4.5 | 5 | 5.5 |
| HDL 5 | 0 | 0 | 0 | 0 | 0 | 0 | 0 | 0 | 0 | 0 | 0 |
| 10 | 0 | 0 | 0 | 0 | 0 | 0 | 0 | 0 | 0 | 0 | 0 |
| 15 | 0 | 0 | 0 | 0 | 0 | 0 | 0 | 0 | 0 | 0 | 0 |
| 20 | 0 | 0 | 0 | 0 | 0 | 0 | 0 | 1 | 0 | 1 | 0 |
| 25 | 0 | 0 | 0 | 0 | 0 | 0 | 1 | 0 | 2 | 5 | 6 |
| 30 | 0 | 0 | 0 | 0 | 1 | 2 | 3 | 6 | 15 | 14 | 35 |
| 35 | 0 | 0 | 0 | 1 | 0 | 6 | 14 | 36 | 61 | 92 | 106 |
| 40 | 0 | 0 | 0 | 1 | 2 | 13 | 52 | 119 | 189 | 260 | 302 |
| 45 | 0 | 0 | 0 | 1 | 7 | 50 | 160 | 350 | 485 | 513 | 438 |
| 50 | 0 | 0 | 0 | 3 | 23 | 130 | 387 | 669 | 694 | 522 | 366 |
| 55 | 0 | 0 | 0 | 2 | 45 | 285 | 652 | 825 | 681 | 424 | 199 |
| 60 | 0 | 0 | 0 | 8 | 98 | 481 | 829 | 762 | 509 | 264 | 98 |
| 65 | 0 | 0 | 1 | 5 | 166 | 614 | 810 | 586 | 286 | 122 | 36 |
| 70 | 0 | 0 | 0 | 11 | 226 | 598 | 620 | 346 | 136 | 49 | 9 |
| 75 | 0 | 0 | 1 | 26 | 271 | 547 | 428 | 174 | 51 | 16 | 7 |
| 80 | 0 | 0 | 1 | 34 | 307 | 402 | 298 | 88 | 23 | 10 | 0 |
| 85 | 0 | 0 | 0 | 32 | 253 | 323 | 157 | 34 | 11 | 2 | 1 |
| 90 | 0 | 0 | 0 | 44 | 230 | 219 | 71 | 21 | 5 | 1 | 0 |
| 95 | 0 | 0 | 3 | 46 | 185 | 126 | 39 | 6 | 4 | 0 | 0 |
| 100 | 0 | 0 | 2 | 34 | 143 | 73 | 17 | 2 | 1 | 1 | 0 |
| 105 | 0 | 0 | 1 | 27 | 85 | 32 | 5 | 2 | 0 | 0 | 0 |
| 110 | 0 | 0 | 0 | 15 | 39 | 13 | 1 | 0 | 0 | 0 | 0 |
| 115 | 0 | 0 | 2 | 15 | 26 | 7 | 4 | 1 | 0 | 0 | 0 |

TABLE 6-continued

| | | | | | | | | | | | |
|---|---|---|---|---|---|---|---|---|---|---|---|
| 120 | 0 | 0 | 0 | 17 | 21 | 5 | 1 | 0 | 1 | 0 | 0 |
| 120+ | 0 | 0 | 4 | 46 | 27 | 6 | 2 | 0 | 0 | 0 | 0 |
| Total | 0 | 0 | 15 | 368 | 2155 | 3932 | 4551 | 4028 | 3154 | 2296 | 1603 |

Number of deaths-HDL x TC/HDL ratio

TC/HDL ratio group

| | | 6 | 6.5 | 7 | 7.5 | 8 | 8.5 | 9 | 9.5 | 10 | 10+ | Total |
|---|---|---|---|---|---|---|---|---|---|---|---|---|
| HDL | 5 | 0 | 0 | 0 | 0 | 0 | 0 | 0 | 0 | 0 | 0 | 0 |
| | 10 | 0 | 0 | 0 | 0 | 0 | 0 | 0 | 0 | 0 | 0 | 0 |
| | 15 | 0 | 0 | 0 | 1 | 0 | 0 | 0 | 0 | 0 | 1 | 2 |
| | 20 | 0 | 2 | 1 | 2 | 3 | 0 | 0 | 2 | 2 | 28 | 42 |
| | 25 | 4 | 3 | 6 | 11 | 10 | 4 | 14 | 10 | 3 | 33 | 112 |
| | 30 | 28 | 46 | 58 | 64 | 37 | 43 | 33 | 28 | 20 | 40 | 473 |
| | 35 | 143 | 137 | 143 | 96 | 82 | 46 | 20 | 18 | 8 | 28 | 1037 |
| | 40 | 267 | 222 | 155 | 117 | 51 | 25 | 19 | 11 | 6 | 8 | 1819 |
| | 45 | 312 | 186 | 91 | 61 | 41 | 19 | 14 | 5 | 2 | 5 | 2740 |
| | 50 | 210 | 100 | 50 | 28 | 12 | 5 | 2 | 2 | 0 | 2 | 3205 |
| | 55 | 99 | 47 | 16 | 5 | 6 | 5 | 1 | 1 | 0 | 1 | 3294 |
| | 60 | 28 | 13 | 8 | 2 | 1 | 1 | 1 | 0 | 0 | 0 | 3103 |
| | 65 | 18 | 3 | 4 | 2 | 0 | 0 | 0 | 0 | 0 | 0 | 2653 |
| | 70 | 5 | 0 | 0 | 0 | 0 | 0 | 0 | 1 | 0 | 0 | 2001 |
| | 75 | 1 | 0 | 0 | 0 | 0 | 0 | 0 | 0 | 0 | 0 | 1522 |
| | 80 | 1 | 0 | 1 | 0 | 0 | 0 | 0 | 0 | 0 | 0 | 1165 |
| | 85 | 0 | 0 | 0 | 0 | 0 | 0 | 0 | 0 | 0 | 0 | 813 |
| | 90 | 0 | 0 | 0 | 0 | 0 | 0 | 0 | 0 | 0 | 0 | 591 |
| | 95 | 0 | 0 | 0 | 0 | 0 | 0 | 0 | 0 | 0 | 0 | 409 |
| | 100 | 0 | 0 | 0 | 0 | 0 | 0 | 0 | 0 | 0 | 0 | 273 |
| | 105 | 1 | 0 | 0 | 0 | 0 | 0 | 0 | 0 | 0 | 0 | 153 |
| | 110 | 0 | 0 | 0 | 0 | 0 | 0 | 0 | 0 | 0 | 0 | 68 |
| | 115 | 0 | 0 | 0 | 0 | 0 | 0 | 0 | 0 | 0 | 0 | 55 |
| | 120 | 0 | 0 | 0 | 0 | 0 | 0 | 0 | 0 | 0 | 0 | 45 |
| | 120+ | 0 | 0 | 0 | 0 | 0 | 0 | 0 | 0 | 0 | 0 | 85 |
| Total | | 1117 | 759 | 533 | 389 | 243 | 148 | 104 | 78 | 41 | 146 | 25660 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented system for generating a searchable database comprising a multi-dimensional lookup table for input classification, the system comprising:
   (a) a computing device comprising a processor, a memory, and an operating system configured to perform executable instructions; and
   (b) instructions executable by the computing device, wherein the system is operative to:
      (i) extract data from a population of data records using the computing device;
      (ii) import the data using the computing device, the data comprising first parameter data, second parameter data, and outcome data from the population of data records;
      (iii) group the first parameter data into a first plurality of data groups and the second parameter data into a second plurality of data groups using the computing device;
      (iv) join the first plurality of data groups with the second plurality of data groups thereby generating a plurality of joint parameters using the computing device;
      (v) compare the outcome data with the plurality of joint parameters thereby generating joint outcome data using the computing device, wherein the computing device determines an area of overlapping values in the overlap map including where total population percentage is largest and the outcome rate is lowest;
      (vi) determine a distribution of the plurality of joint parameters using the computing device;
      (vii) determine one or more areas of overlap between the distribution of the plurality of joint parameters and the joint outcome data using the computing device;
      (viii) generate one or more overlap intervals based on the one or more areas of overlap using the computing device; and
      (ix) generate a multi-dimensional lookup table comprising the one or more overlap intervals using the computing device, wherein the multi-dimensional lookup table is embedded within a searchable database accessed through a portal, wherein the portal is configured to receive input parameter values and generate an output comprising a classification of the input parameter values based on a comparison of the input parameter values with the one or more overlap intervals of the multi-dimensional lookup table.

2. The system of claim 1, wherein the system is operative to detect whether the one or more areas of overlap is present between the distribution of the plurality of joint parameters and the joint outcome data using the computing device.

3. The system of claim 1, wherein the system is further operative to interface with a distributed network of computing devices and provide the portal through the distributed network of computing devices.

4. The system of claim 1, wherein the system is further operative to generate a 3D visualization of the distribution of the plurality of joint parameters and a 3D visualization of the joint or outcome data using the computing system.

5. The system of claim 4, wherein the system is further operative to send instructions to an output device to print or create a physical representation of the 3D visualization of the distribution of the plurality of joint parameters and/or the 3D visualization of the joint or outcome data using the computing system.

6. The system of claim 5, wherein the physical representation is a paper printout, a poster, or a 3D printed map or model.

7. The system of claim 1, wherein the system is further operative to send instructions to an output device to print or create a physical representation of the multi-dimensional lookup table.

8. The system of claim 7, wherein the physical representation is a paper printout, a poster, or a 3D printed map or model.

9. A computer-implemented system for processing parameter data in order to generate one or more reference intervals, the system comprising:
   (a) a computing device comprising a processor, a memory, and an operating system configured to perform executable instructions; and
   (b) executable instructions that cause the system to:
      (i) receive a first plurality of parameter values, a second plurality of parameter values, a population percentage, and an outcome rate using the computing device, wherein the first plurality of parameter values, the second plurality of parameter values, or both are measured in a population;
      (ii) map, in three dimensions, the first and the second parameter values with the population percentage using the computing device, thereby generating a population percentage map;
      (iii) map, in three dimensions, the first and the second parameter values with the outcome rate using the computing device, thereby generating an outcome rate map;
      (iv) compare the population percentage map with the outcome rate map thereby generating an overlap map using the computing device;
      (v) generate the one or more reference intervals based on the overlap map using the computing device; and
      (vi) generate a multi-dimensional lookup table comprising the one or more reference intervals using the computing device, wherein the multi-dimensional lookup table is embedded within a searchable database.

10. The system of claim 9, wherein the system is further caused to segregate the first plurality of parameter values into a first plurality of value groups and segregate the second plurality of parameter values into a second plurality of value groups using the computing device.

11. The system of claim 10, wherein the system is further caused to determine an upper value limit and a lower value limit of each of the first plurality of value groups and each of the second plurality of value groups using the computing device after the overlap map is generated.

12. The system of claim 11, wherein the system is further caused to associate, respectively, each of the first plurality of value groups with each of the second plurality of value groups using the computing device, thereby generating a plurality of associated groups.

13. The system of claim 9, wherein the one or more reference intervals comprises upper values and lower values of the area of overlapping values in the overlap map where total population percentage is largest and the outcome rate is lowest.

14. A computer implemented method for processing parameter and population data to generate a searchable database with reference intervals, comprising:
   (i) receiving a first plurality of parameter values, a second plurality of parameter values, a population percentage, and an outcome rate using a computing device, wherein the first plurality of parameter values, the second plurality of parameter values, or both are measured in a population;
   (ii) mapping, graphically in at least three dimensions, the first and the second parameter values with the population percentage using the computing device, thereby generating a population percentage map;
   (iii) mapping, graphically in at least three dimensions, the first and the second parameter values with the outcome rate using the computing device, thereby generating an outcome rate map;
   (iv) comparing the population percentage map with the outcome rate map using the computing device, thereby generating an overlap map;
   (v) generating reference interval values based on the overlap map using the computing device; and
   (vi) populating the database with a multi-dimensional lookup table comprising the reference interval values using the computing device, wherein the multi-dimensional lookup table is embedded within a searchable database accessed through a portal, wherein the portal is configured to receive input parameter values and generate an output comprising a classification of the input parameter values based on a comparison of the input parameter values with the reference interval values of the multi-dimensional lookup table.

15. The computer implemented method of claim 14, comprising segregating the first plurality of parameter values into a first plurality of value groups and segregating the second plurality of parameter values into a second plurality of value groups using the computing device.

16. The computer implemented method of claim 14, comprising determining an area of overlapping values in the overlap map where total population percentage is largest and the outcome rate is lowest using the computing device.

17. The computer implemented method of claim 16, wherein the reference interval values comprise upper values and lower values of the area of overlapping values in the overlap map where total population percentage is largest and the outcome rate is lowest.

18. The computer implemented method of claim 14, further comprising sending instructions to an output device using the computing device to print or create a physical representation of the multi-dimensional lookup table comprising the reference intervals.

19. The computer implemented method of claim 18, wherein the physical representation is a paper printout, a poster, or a 3D printed map or model.

* * * * *